(12) United States Patent
Seddon et al.

(10) Patent No.: US 12,426,884 B2
(45) Date of Patent: Sep. 30, 2025

(54) SYSTEMS, DEVICES, AND METHODS FOR FORMING ANASTOMOSES

(71) Applicant: G.I. Windows, Inc., Westwood, MA (US)

(72) Inventors: Dane Seddon, Boston, MA (US); Peter Lukin, Norfolk, MA (US); Jonathan B. O'Keefe, North Attleborough, MA (US); Amos Cruz, Wrentham, MA (US); Jeffrey C. Cerier, Franklin, MA (US); Keith D. Boudreau, North Andover, MA (US); Taylor Bensel, Foxborough, MA (US); David A. Rezac, Hopkinton, MA (US)

(73) Assignee: G.I. Windows, Inc., Westwood, MA (US)

( * ) Notice: Subject to any disclaimer, the term of this patent is extended or adjusted under 35 U.S.C. 154(b) by 0 days.

(21) Appl. No.: 18/236,194

(22) Filed: Aug. 21, 2023

(65) Prior Publication Data

US 2023/0389924 A1    Dec. 7, 2023

Related U.S. Application Data

(63) Continuation of application No. 17/108,840, filed on Dec. 1, 2020, now Pat. No. 11,751,877, which is a
(Continued)

(51) Int. Cl.
*A61B 17/11* (2006.01)
*A61B 17/00* (2006.01)

(52) U.S. Cl.
CPC . *A61B 17/1114* (2013.01); *A61B 2017/00876* (2013.01); *A61B 2017/1132* (2013.01)

(58) Field of Classification Search
CPC .. A61B 2017/1132; A61B 2017/00876; A61B 17/1114; A61B 17/11
See application file for complete search history.

(56) References Cited

U.S. PATENT DOCUMENTS

| 4,197,840 A | 4/1980 | Beck et al. |
| 4,538,130 A | 8/1985 | Gluckstern et al. |

(Continued)

FOREIGN PATENT DOCUMENTS

| CN | 105011985 A | 11/2015 |
| CN | 205379345 U | 7/2016 |

(Continued)

OTHER PUBLICATIONS

Author Unknown, "An Innovative Implant for the Creation of Anastomosis," PLIO, retrieved from the internet at: https://pliosurgical.com/, Jan. 19, 2024 (13 pages).

(Continued)

*Primary Examiner* — Brooke Labranche
*Assistant Examiner* — Christina C Lauer
(74) *Attorney, Agent, or Firm* — Nutter McClennen & Fish LLP

(57) ABSTRACT

The invention provides systems, devices, and methods for the delivery, deployment, and positioning of magnetic compression devices at a desired site so as to improve the accuracy of anastomoses creation between tissues, organs, or the like.

20 Claims, 53 Drawing Sheets

Related U.S. Application Data continuation-in-part of application No. PCT/US2019/035202, filed on Jun. 3, 2019.

(60) Provisional application No. 62/809,354, filed on Feb. 22, 2019, provisional application No. 62/798,809, filed on Jan. 30, 2019, provisional application No. 62/679,810, filed on Jun. 2, 2018.

(56) References Cited

U.S. PATENT DOCUMENTS

| | | |
|---|---|---|
| 5,300,910 A | 4/1994 | Unkelbach et al. |
| 5,320,629 A | 6/1994 | Noda et al. |
| 5,381,784 A | 1/1995 | Adair |
| 5,431,670 A | 7/1995 | Holmes |
| 5,595,562 A | 1/1997 | Grier |
| 5,690,656 A | 11/1997 | Cope et al. |
| 6,129,668 A | 10/2000 | Haynor et al. |
| 6,132,458 A | 10/2000 | Staehle et al. |
| 6,190,303 B1 | 2/2001 | Glenn et al. |
| 6,273,895 B1 | 8/2001 | Pinchuk et al. |
| 6,352,543 B1 | 3/2002 | Cole |
| 6,371,964 B1 | 4/2002 | Vargas et al. |
| 6,478,210 B2 | 11/2002 | Adams et al. |
| 6,537,284 B1 | 3/2003 | Inoue |
| 6,632,229 B1 | 10/2003 | Yamanouchi et al. |
| 6,652,540 B1 | 11/2003 | Cole et al. |
| 6,699,263 B2 | 3/2004 | Cope |
| 6,719,768 B1 | 4/2004 | Cole et al. |
| 6,802,847 B1 | 10/2004 | Carson et al. |
| 6,827,718 B2 | 12/2004 | Hutchins et al. |
| 6,932,827 B2 | 8/2005 | Cole |
| 7,282,057 B2 | 10/2007 | Surti et al. |
| 7,618,427 B2 | 11/2009 | Oritz et al. |
| 7,641,638 B2 | 1/2010 | Waxman et al. |
| 7,760,059 B2 | 7/2010 | Higuchi |
| 7,909,837 B2 | 3/2011 | Crews et al. |
| 8,043,290 B2 | 10/2011 | Harrison et al. |
| 8,118,821 B2 | 2/2012 | Mouw |
| 8,142,454 B2 | 3/2012 | Harrison et al. |
| 8,262,680 B2 | 9/2012 | Swain et al. |
| 8,439,915 B2 | 5/2013 | Harrison et al. |
| 8,506,516 B2 | 8/2013 | Kassab et al. |
| 8,518,062 B2 | 8/2013 | Cole et al. |
| 8,556,919 B2 | 10/2013 | Aguirre et al. |
| 8,603,121 B2 | 12/2013 | Surti et al. |
| 8,623,036 B2 | 1/2014 | Harrison et al. |
| 8,679,139 B2 | 3/2014 | Aguirre et al. |
| 8,685,046 B2 | 4/2014 | Viola |
| 8,728,105 B2 | 5/2014 | Aguirre |
| 8,794,243 B2 | 8/2014 | Deem et al. |
| 8,828,031 B2 | 9/2014 | Fox et al. |
| 8,828,032 B2 | 9/2014 | McWeeney et al. |
| 8,845,663 B2 | 9/2014 | Chmura |
| 8,864,781 B2 | 10/2014 | Surti et al. |
| 8,870,899 B2 | 10/2014 | Beisel et al. |
| 8,915,915 B2 | 12/2014 | Harrison et al. |
| 9,168,041 B2 | 10/2015 | Zaritsky et al. |
| 9,226,753 B2 | 1/2016 | Surti et al. |
| 9,320,524 B2 | 4/2016 | Gagner et al. |
| 9,421,015 B2 | 8/2016 | Gagner et al. |
| 9,456,820 B2 | 10/2016 | Gagner et al. |
| 9,492,173 B2 | 11/2016 | McWeeney et al. |
| 9,539,010 B2 | 1/2017 | Gagner et al. |
| 9,763,664 B2 | 9/2017 | Beisel et al. |
| 9,801,635 B2 | 10/2017 | Gagner et al. |
| 9,877,724 B2 | 1/2018 | Gagner et al. |
| 9,943,335 B2 | 4/2018 | Gittard et al. |
| 10,039,550 B2 | 8/2018 | Altman |
| 10,159,487 B2 | 12/2018 | Gagner et al. |
| 10,182,821 B2 | 1/2019 | Lukin et al. |
| 10,285,703 B2 | 5/2019 | Viola |
| 10,342,544 B2 | 7/2019 | Bakos et al. |
| 10,376,400 B2 | 8/2019 | McGuckin, Jr. |
| 10,448,954 B2 | 10/2019 | McWeeney et al. |
| 10,517,600 B2 | 12/2019 | Beisel et al. |
| 10,555,735 B2 | 2/2020 | Bakos et al. |
| 10,568,630 B2 | 2/2020 | Hernandez et al. |
| 10,595,869 B2 | 3/2020 | Beisel et al. |
| 10,624,643 B2 | 4/2020 | Hunt et al. |
| 10,624,644 B2 | 4/2020 | Bakos et al. |
| 10,631,865 B2 | 4/2020 | Bakos et al. |
| 10,667,817 B2 | 6/2020 | Gagner et al. |
| 10,682,143 B2 | 6/2020 | Hernandez et al. |
| 10,779,831 B2 | 9/2020 | Lukin et al. |
| 10,813,642 B2 | 10/2020 | Beisel et al. |
| 10,952,732 B2 | 3/2021 | Binmoeller et al. |
| 11,039,838 B2 | 6/2021 | Binmoeller et al. |
| 11,311,298 B2 | 4/2022 | Gagner et al. |
| 11,432,873 B2 | 9/2022 | Brown et al. |
| 2002/0055674 A1 | 5/2002 | Ben-Haim et al. |
| 2002/0143347 A1 | 10/2002 | Cole et al. |
| 2003/0149422 A1 | 8/2003 | Muller |
| 2003/0176767 A1 | 9/2003 | Long et al. |
| 2004/0034377 A1 | 2/2004 | Sharkawy et al. |
| 2004/0059280 A1 | 3/2004 | Makower et al. |
| 2005/0020958 A1 | 1/2005 | Paolini et al. |
| 2005/0080439 A1 | 4/2005 | Carson et al. |
| 2005/0256503 A1 | 11/2005 | Hall |
| 2005/0277966 A1 | 12/2005 | Ewers et al. |
| 2005/0283235 A1 | 12/2005 | Kugler et al. |
| 2006/0036267 A1 | 2/2006 | Saadat et al. |
| 2006/0271107 A1 | 11/2006 | Harrison et al. |
| 2006/0282106 A1 | 12/2006 | Cole et al. |
| 2007/0106312 A1 | 5/2007 | Vargas et al. |
| 2007/0276378 A1 | 11/2007 | Harrison et al. |
| 2008/0051626 A1 | 2/2008 | Sato et al. |
| 2008/0086192 A1 | 4/2008 | WasDyke et al. |
| 2008/0114384 A1 | 5/2008 | Chang et al. |
| 2008/0183272 A1 | 7/2008 | Wood et al. |
| 2008/0200933 A1 | 8/2008 | Bakos et al. |
| 2008/0200934 A1 | 8/2008 | Fox |
| 2008/0208105 A1 | 8/2008 | Zelickson et al. |
| 2008/0208224 A1 | 8/2008 | Surti et al. |
| 2008/0243225 A1 | 10/2008 | Satasiya et al. |
| 2008/0262523 A1 | 10/2008 | Makower et al. |
| 2009/0048618 A1 | 2/2009 | Harrison et al. |
| 2009/0062824 A1 | 3/2009 | Berg et al. |
| 2009/0125042 A1 | 5/2009 | Mouw |
| 2009/0227828 A1 | 9/2009 | Swain et al. |
| 2010/0010508 A1 | 1/2010 | Takahashi et al. |
| 2010/0010610 A1 | 1/2010 | Grevious |
| 2010/0036399 A1 | 2/2010 | Viola |
| 2010/0056861 A1 | 3/2010 | Spivey |
| 2010/0099947 A1 | 4/2010 | Sato et al. |
| 2010/0179510 A1 | 7/2010 | Fox et al. |
| 2011/0009886 A1 | 1/2011 | Gagner et al. |
| 2011/0009895 A1* | 1/2011 | Gertner ............ A61B 17/0487 606/191 |
| 2011/0098731 A1 | 4/2011 | Whitbrook et al. |
| 2011/0118765 A1 | 5/2011 | Aguirre |
| 2011/0144560 A1 | 6/2011 | Gagner et al. |
| 2011/0160751 A1 | 6/2011 | Granja Filho |
| 2011/0160752 A1 | 6/2011 | Aguirre |
| 2011/0295055 A1 | 12/2011 | Albrecht et al. |
| 2011/0295285 A1* | 12/2011 | McWeeney ......... A61B 17/1114 606/153 |
| 2012/0022572 A1 | 1/2012 | Braun et al. |
| 2012/0197062 A1 | 8/2012 | Requarth |
| 2012/0238796 A1 | 9/2012 | Conlon |
| 2012/0259350 A1 | 10/2012 | Gagner et al. |
| 2012/0330330 A1 | 12/2012 | Gagner et al. |
| 2013/0138126 A1 | 5/2013 | Gagner et al. |
| 2013/0150873 A1 | 6/2013 | Gagner et al. |
| 2013/0253548 A1 | 9/2013 | Harrison et al. |
| 2013/0253550 A1 | 9/2013 | Beisel et al. |
| 2013/0325042 A1 | 12/2013 | Fabian et al. |
| 2014/0018824 A1 | 1/2014 | Julian et al. |
| 2014/0019468 A1 | 1/2014 | Federoff et al. |
| 2014/0066709 A1 | 3/2014 | Mirza et al. |
| 2014/0188246 A1 | 7/2014 | Aronson et al. |
| 2014/0194689 A1 | 7/2014 | Carrillo, Jr. et al. |
| 2014/0236064 A1 | 8/2014 | Binmoeller et al. |
| 2014/0243592 A1 | 8/2014 | Kato et al. |

(56) References Cited

U.S. PATENT DOCUMENTS

| | | |
|---|---|---|
| 2014/0277342 A1 | 9/2014 | Roeder et al. |
| 2014/0303657 A1 | 10/2014 | Kim et al. |
| 2014/0309669 A1 | 10/2014 | Fabian et al. |
| 2014/0309670 A1 | 10/2014 | Bakos et al. |
| 2014/0343583 A1 | 11/2014 | McWeeney et al. |
| 2014/0379065 A1 | 12/2014 | Johnson et al. |
| 2015/0057687 A1 | 2/2015 | Gittard et al. |
| 2015/0164508 A1 | 6/2015 | Hernandez et al. |
| 2015/0182224 A1 | 7/2015 | Altman |
| 2016/0022266 A1* | 1/2016 | Lukin ............... A61B 17/1114 606/154 |
| 2016/0235442 A1 | 8/2016 | Palese et al. |
| 2016/0262761 A1 | 9/2016 | Beisel et al. |
| 2016/0287257 A1 | 10/2016 | Fabian et al. |
| 2016/0324523 A1 | 11/2016 | Lukin et al. |
| 2016/0367236 A1 | 12/2016 | Leeflang et al. |
| 2016/0374683 A1 | 12/2016 | Gagner et al. |
| 2017/0035425 A1 | 2/2017 | Fegelman et al. |
| 2017/0265866 A1 | 9/2017 | Ryou et al. |
| 2018/0028186 A1 | 2/2018 | Yamanouchi |
| 2018/0028187 A1 | 2/2018 | Gagner et al. |
| 2018/0193061 A1 | 7/2018 | Gittard et al. |
| 2018/0214149 A1 | 8/2018 | Hunt et al. |
| 2018/0214150 A1 | 8/2018 | Bakos et al. |
| 2018/0214152 A1 | 8/2018 | Bakos et al. |
| 2018/0263625 A1 | 9/2018 | Lukin et al. |
| 2018/0296218 A1 | 10/2018 | Binmoeller et al. |
| 2018/0361127 A1 | 12/2018 | Gray et al. |
| 2019/0133587 A1 | 5/2019 | Gagner et al. |
| 2019/0133678 A1 | 5/2019 | Pate et al. |
| 2019/0183507 A1 | 6/2019 | Baillargeon |
| 2019/0216460 A1 | 7/2019 | Kopelman |
| 2019/0261998 A1 | 8/2019 | Altman et al. |
| 2019/0274687 A1 | 9/2019 | Wang et al. |
| 2019/0328392 A1 | 10/2019 | Sharma |
| 2020/0008834 A1 | 1/2020 | Cauche et al. |
| 2020/0129283 A1 | 4/2020 | Swensgard et al. |
| 2020/0138438 A1 | 5/2020 | Harrison et al. |
| 2020/0170776 A1 | 6/2020 | Folan |
| 2020/0187947 A1 | 6/2020 | Hernandez et al. |
| 2020/0222049 A1 | 7/2020 | McWeeney et al. |
| 2020/0229968 A1 | 7/2020 | Galloway |
| 2020/0246009 A1 | 8/2020 | Gagner et al. |
| 2020/0323530 A1 | 10/2020 | Sharma |
| 2021/0100554 A1 | 4/2021 | Seddon et al. |
| 2021/0161532 A1 | 6/2021 | Beisel et al. |
| 2021/0169485 A1 | 6/2021 | Beisel et al. |
| 2021/0169486 A1 | 6/2021 | Gagner et al. |
| 2021/0244414 A1 | 8/2021 | Lukin et al. |
| 2022/0087678 A1 | 3/2022 | Gagner et al. |
| 2022/0104956 A1 | 4/2022 | Pham et al. |
| 2022/0257252 A1 | 8/2022 | Todd et al. |
| 2023/0165585 A1 | 6/2023 | McWeeney et al. |
| 2023/0172608 A1 | 6/2023 | Lukin et al. |
| 2023/0190269 A1 | 6/2023 | Tinkham et al. |
| 2023/0255624 A1 | 8/2023 | Wallace et al. |
| 2023/0389923 A1 | 12/2023 | Tinkham et al. |
| 2024/0041460 A1 | 2/2024 | Seddon |
| 2024/0041461 A1 | 2/2024 | Tinkham et al. |
| 2024/0065694 A1 | 2/2024 | Seddon |
| 2024/0074751 A1 | 3/2024 | Tinkham et al. |
| 2024/0074755 A1 | 3/2024 | Mann et al. |
| 2024/0074759 A1 | 3/2024 | Sugar et al. |

FOREIGN PATENT DOCUMENTS

| | | |
|---|---|---|
| DE | 3011742 A1 | 10/1981 |
| EP | 1894514 A2 | 3/2008 |
| EP | 1493391 B1 | 12/2009 |
| EP | 2207488 B1 | 9/2012 |
| EP | 2538852 A1 | 1/2013 |
| EP | 3267905 A1 | 1/2018 |
| EP | 2260752 B1 | 3/2018 |
| EP | 3573542 A1 | 12/2019 |
| EP | 3487418 A4 | 4/2020 |
| EP | 4115949 A1 | 1/2023 |
| JP | 2003530916 A | 10/2003 |
| JP | 2006271832 A | 10/2006 |
| JP | 2008508939 A | 3/2008 |
| JP | 2011500159 A | 1/2011 |
| JP | 2015139592 A | 8/2015 |
| JP | 2017/521223 A | 8/2017 |
| JP | 202198077 A | 7/2021 |
| KR | 20150102567 A | 9/2015 |
| RU | 2018266 C1 | 8/1994 |
| SU | 1708313 A1 | 1/1992 |
| SU | 1725851 A1 | 4/1992 |
| WO | 01/087398 A2 | 11/2001 |
| WO | 01/93920 A2 | 12/2001 |
| WO | 2009048954 A1 | 4/2009 |
| WO | 2011085006 A2 | 7/2011 |
| WO | 2011/103400 A1 | 8/2011 |
| WO | 2013009886 A1 | 1/2013 |
| WO | 2013/176993 A1 | 11/2013 |
| WO | 2014055193 A1 | 4/2014 |
| WO | 2016082481 A1 | 6/2016 |
| WO | 2016/145414 A1 | 9/2016 |
| WO | 2018022180 A1 | 2/2018 |
| WO | 2018/138632 A1 | 8/2018 |
| WO | 2019077218 A1 | 4/2019 |
| WO | 2019232526 A1 | 12/2019 |
| WO | 2019232527 A1 | 12/2019 |
| WO | 2020/196336 A1 | 10/2020 |
| WO | 2021/203910 A1 | 10/2021 |
| WO | 2021/207821 A1 | 10/2021 |
| WO | 2022/061117 A1 | 3/2022 |
| WO | 2022/132351 A1 | 6/2022 |
| WO | 2022/171349 A1 | 8/2022 |

OTHER PUBLICATIONS

European Patent Office, Communication pursuant to Article 94(3) EPC for Application No. 19810895.3, dated Feb. 13, 2023 (3 pages).

Extended European Search Report, European Patent Office, Application No. 19810895.3, dated Feb. 7, 2022, 10 pages.

Gagner, M., "Duodeno-Ileal Anastomosis with Self-Assembling Magnets: Initial Concepts and Basis of This Operation", Obesity Surgery 32, 932-933 (2022).

International Search Report and Written Opinion issued for Application No. PCT/US2016/031547 dated Oct. 18, 2016, 18 pages.

International Search Report and Written Opinion of the International Searching Authority, Application No. PCT/US2019035202, mailed Aug. 8, 2019, 6 pages.

International Search Report and Written Opinion of the International Searching Authority, Application No. PCT/US2022/25343, mailed Jul. 18, 2022, 14 pages.

International Search Report and Written Opinion of the International Searching Authority, Application No. PCT/US2022/25353, mailed Jun. 30, 2022, 12 pages.

International Search Report and Written Opinion of the International Searching Authority, for Application No. PCT/US2011/020229, with a date of mailing of Jun. 21, 2013, 6 pages.

International Search Report and Written Opinion of the International Searching Authority, for Application No. PCT/US2013/041641, dated Oct. 18, 2013, 4 pages.

International Search Report and Written Opinion of the International Searching Authority, for Application No. PCT/US2015/041498 dated Nov. 17, 2015.

International Search Report and Written Opinion of the International Searching Authority, for Application PCT/2023/031863, dated Jan. 22, 2024, 8 pages.

International Search Report and Written Opinion of the International Searching Authority, for Application PCT/US2016/022209, dated May 30, 2016.

International Search Report and Written Opinion of the International Searching Authority, for Application PCT/US2023/031861, dated Feb. 2, 2024, 9 pages.

International Search Report and Written Opinion of the International Searching Authority, for Application PCT/US2023/035976, dated Feb. 2, 2024, 11 pages.

(56) References Cited

OTHER PUBLICATIONS

International Search Report and Written Opinion of the International Searching Authority, for Application PCT/US22/25338, dated Aug. 19, 2022, 14 pages.
International Search Report and Written Opinion of the International Searching Authority, for Application PCT/US23/29416, dated Dec. 7, 2023, 9 pages.
International Search Report and Written Opinion of the International Searching Authority, for Application PCT/US23/29432, dated Nov. 14, 2023, 7 pages.
Invitation to Pay Additional Fees and, Where Applicable, Protest Fee, from the International Search Authority, Application No. PCT/US2022/025338, mailed Jun. 23, 2022, 2 pages.
Invitation to Pay Additional Fees and, Where Applicable, Protest Fee, from the International Search Authority, Application No. PCT/US2022/025370, mailed Jun. 24, 2022, 3 pages.
Jamshidi, et al., "Magnamosis: magnetic compression anastomosis with comparison to suture and staple techniques," Journal of Pediatric Surgery, vol. 4, Issue 1, pp. 222-228. Jan. 20, 2009 (Jan. 20, 2009). [Retrieved on Dec. 5, 2023]. Retrieved from the Internet: <URL: https://dotorg/10.1016/j.jpedsurg.2008.10.044>. entire document.
Japanese Office Action for Japanese Patent Application No. 2021-034336 dated Dec. 17, 2021, 3 pages.
Japanese Office Action, Notice of Reasons for Refusal, Japanese Patent Application No. 2020-567134 dated Feb. 21, 2023.
Japanese Penultimate Office Action for Japanese Patent Application No. 2021-034336 dated Aug. 1, 2022, 9 pages.
Japanese Search Report, Japanese Application No. 2020-567134, dated Feb. 13, 2023, 28 pages.
Supplementary Partial European Search Report for Application No. EP 13793804.9 dated Jan. 15, 2016, 9 pages.

\* cited by examiner

STEP 1: DEVICE ENTERS GALL BLADDER USING MONOPOLAR ENERGY

STEP 2: REMOVE SHEATH

STEP 3: SHEATH FULLY REMOVED

STEP 4: INFLATE BALLOON

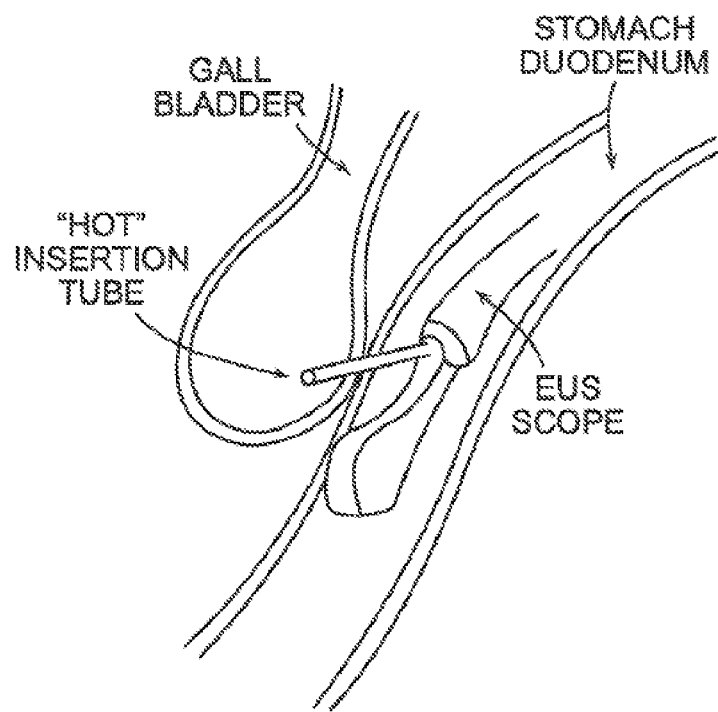
FIG. 20A
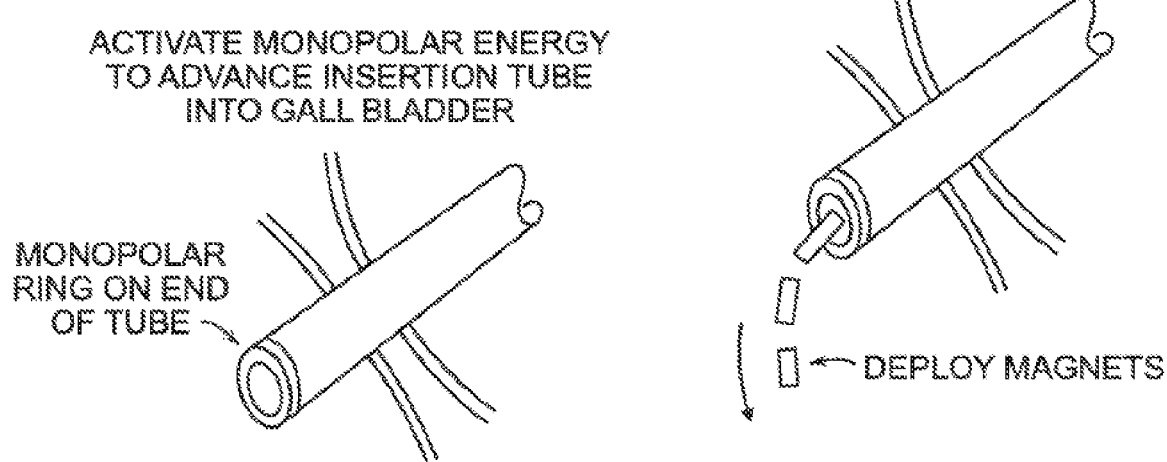
FIG. 20B
FIG. 20C

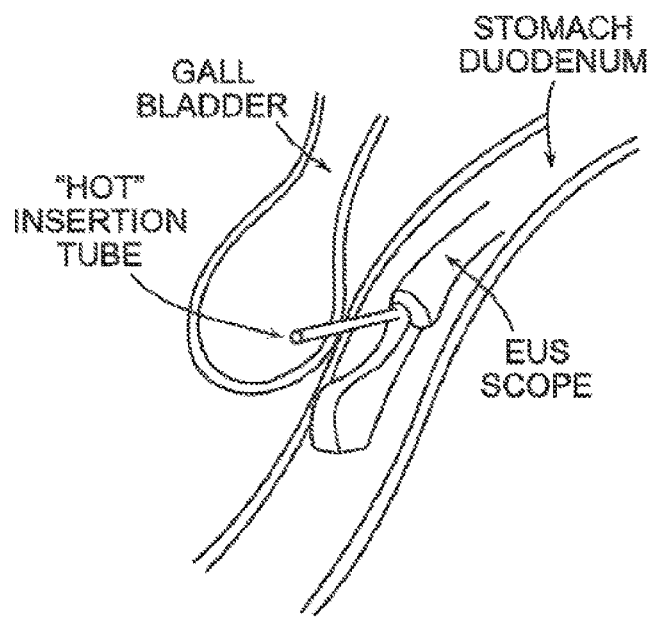
FIG. 21A
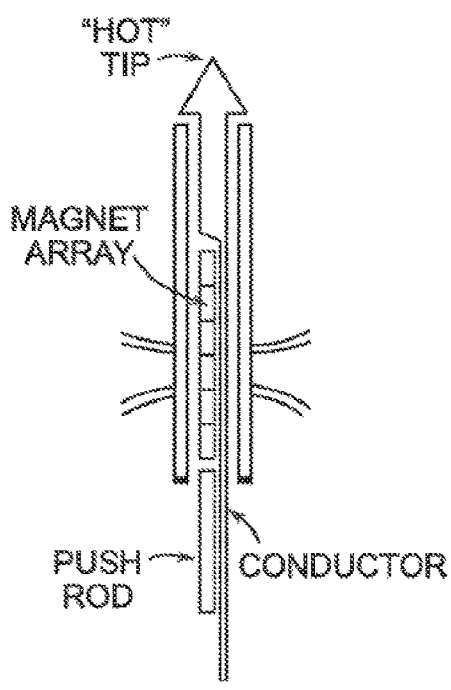
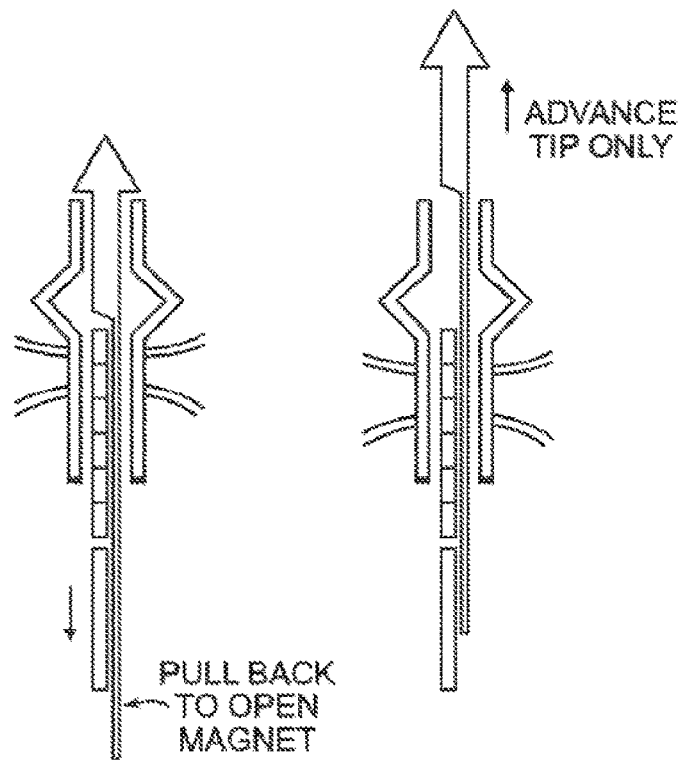
FIG. 21B  FIG. 21C  FIG. 21D

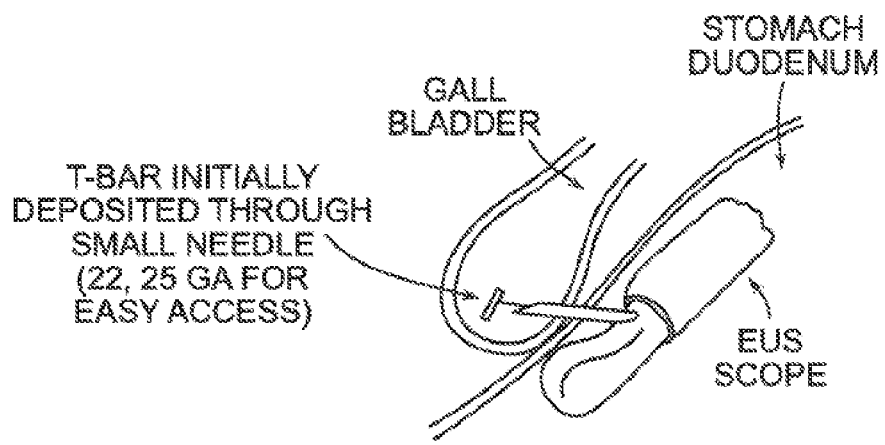
FIG. 25A
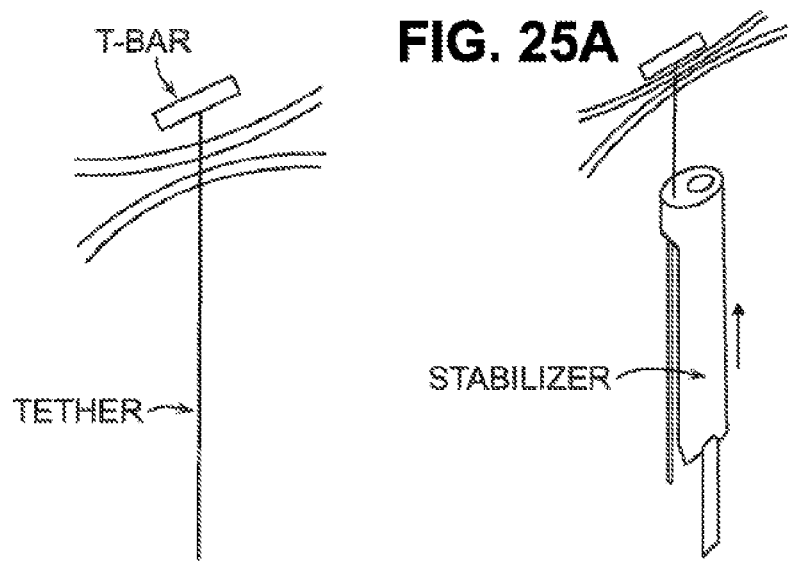
FIG. 25B     FIG. 25C

RING CAN BE FREE SPINNING & ROTATES WHEN MAGNET IS PUSHED OUT... OR RING COULD BE ACTIVELY ROTATED TO PULL MAGNET OUT

FIG. 45     Flexible Endoscopes General Diameter Guide for Endoscopy Brushes

| SCOPE TYPE | INSERTION TUBE OUTER DIAMETER | WORKING LENGTH | INSTRUMENT CHANNEL INTERNAL DIAMETER | HEALTHMARK ENDO BRUSHES | ENDOBRUSH DIAMETER RANGE | OLYMPUS COLOR GUIDE |
|---|---|---|---|---|---|---|
| ADULTS | | | | | | |
| GASTROSCOPE | 9.0 mm - 11.4 mm | 1030 mm - 1050 mm | 2.8mm - 3.8mm | CC-250, CC-374 | 2.6 - 3.2 mm, 3.7 - 4.3 mm | |
| DUODENSCOPE | 10.8 mm - 12.5 mm | 1235 mm - 1250 mm | 3.2mm - 4.2mm | CC-250, CC-374 | 2.6 - 3.2 mm, 3.7 - 4.3 mm | |
| COLONOSCOPE | 12.9 mm - 13.7 mm | 1330 mm - 1680 mm | 3.7mm - 4.2mm | CC-374 | 3.7 - 4.3 mm | |
| SIGMOIDOSCOPE | 12.8 mm - 13.2 mm | 700 mm - 730 mm | 3.7mm - 4.2mm | CC-374 | 3.7 - 4.3 mm | |
| ENTEROSCOPE | 10.5 mm - 11.7 mm | 2200 mm - 2500 mm | 2.8mm - 3.8mm | CC-250, CC-374 | 2.6 - 3.2 mm, 3.7 - 4.3 mm | |
| BRONCHOSCOPE | 5.7 mm - 6.0 mm | 550 mm - 800 mm | 2.0mm - 2.8mm | CC-172, CC-250 | 1.7 - 2.2 mm, 2.6 - 3.2 mm | |
| URETEROSCOPE | 2.8 mm - 3.3 mm | 670 mm - 700 mm | 1.2mm | CC-172 | 1.7 - 2.2 mm | |
| CYSTOSCOPE | 5.4 mm - 5.5 mm | 380 mm | 2.2mm - 2.4mm | CC-172, CC-250 | 1.7 - 2.2 mm, 2.6 - 3.2 mm | |
| RHINO-LARYNGOSCOPE | 2.6 mm - 4.9 mm | 300 mm - 365 mm | N/A-2.0 | CC-172 | 1.7 - 2.2 mm | |
| LAPARO-THORACOSCOPE | 7.0 mm | 270 mm | 2.8 mm | CC-250 | 2.6 - 3.2 mm | |
| MOBILE AIRWAY SCOPE | 4.1 mm - 5.2 mm | 800 mm | 1.5 mm - 2.6 mm | CC-172, CC-250 | 1.7 - 2.2 mm, 2.6 - 3.2 mm | |
| CHOLEDOCHOSCOPE | 2.8 mm - 5.2 mm | 380 mm - 700 mm | 1.2 mm - 2.2 mm | CC-110, CC-172 | 1.2 mm, 1.7 - 2.2 mm | white |
| PEDIATRICS | | | | | | |
| GASTROSCOPE | 5.9 mm - 6.0 mm | 1030 mm - 1050 mm | 2.0 mm | CC-172 | 1.7 - 2.2 mm | |
| COLONOSCOPE | 11.5 mm - 11.6 mm | 1680 mm - 1700 mm | 3.2 mm - 3.8 mm | CC-250, CC-374 | 2.6-3.2 mm, 3.7 - 4.3 mm | |
| BRONCHOSCOPE | 4.4 mm - 5.1 mm | 600 mm | 2.0 mm | CC-172 | 1.7 - 2.2 mm | |

SYSTEMS, DEVICES, AND METHODS FOR FORMING ANASTOMOSES

CROSS-REFERENCE TO RELATED APPLICATIONS

This patent application is a continuation of, and therefore claims priority from, U.S. patent application Ser. No. 17/108,840 entitled SYSTEMS, DEVICES, AND METHODS FOR FORMING ANASTOMOSES filed Dec. 1, 2020, which is a continuation-in-part of, and therefore claims priority from, International Patent Application No. PCT/US2019/035202 having an International Filing Date of Jun. 3, 2019, which claims the benefit of, and priority to, U.S. Provisional Application Ser. No. 62/679,810, filed Jun. 2, 2018, U.S. Provisional Application Ser. No. 62/798,809, filed Jan. 30, 2019, and U.S. Provisional Application Ser. No. 62/809,354, filed Feb. 22, 2019, the contents of each of which are hereby incorporated by reference herein in their entireties.

FIELD OF THE INVENTION

The invention relates to deployable magnetic compression devices, and, more particularly, to systems, devices, and methods for the delivery, deployment, and positioning of magnetic compression devices at a desired site so as to improve the accuracy of anastomoses creation between tissues, organs, or the like.

BACKGROUND

Bypasses of the gastroenterological (GI), cardiovascular, or urological systems are typically formed by cutting holes in tissues at two locations and joining the holes with sutures or staples. A bypass is typically placed to route fluids (e.g., blood, nutrients) between healthier portions of the system, while bypassing diseases or malfunctioning tissues. The procedure is typically invasive, and subjects a patient to risks such as bleeding, infection, pain, and adverse reaction to anesthesia. Additionally, a bypass created with sutures or staples can be complicated by post-operative leaks and adhesions. Leaks may result in infection or sepsis, while adhesions can result in complications such as bowel strangulation and obstruction. While traditional bypass procedures can be completed with an endoscope, laparoscope, or robot, it can be time consuming to join the holes cut into the tissues. Furthermore, such procedures require specialized expertise and equipment that is not available at many surgical facilities.

As an alternative to sutures or staples, surgeons can use mechanical couplings or magnets to create a compressive anastomosis between tissues. For example, compressive couplings or paired magnets can be delivered to tissues to be joined. Because of the strong compression, the tissue trapped between the couplings or magnets is cut off from its blood supply. Under these conditions, the tissue becomes necrotic and degenerates, and at the same time, new tissue grows around points of compression, e.g., on the edges of the coupling. With time, the coupling can be removed, leaving a healed anastomosis between the tissues.

Nonetheless, the difficulty of placing the magnets or couplings limits the locations that compressive anastomosis can be used. In most cases, the magnets or couplings have to be delivered as two separate assemblies, requiring either an open surgical field or a bulky delivery device. For example, existing magnetic compression devices are limited to structures small enough to be deployed with a delivery conduit e.g., an endoscopic instrument channel or laparoscopic port. When these smaller structures are used, the formed anastomosis is small and suffers from short-term patency. Furthermore, placement of the magnets or couplings can be imprecise, which can lead to anastomosis formation in locations that is undesirable or inaccurate.

Thus, there still remains a clinical need for reliable devices and minimally-invasive procedures that facilitate compression anastomosis formation between tissues in the human body.

SUMMARY

The present invention provides improved devices and techniques for minimally-invasive formation of anastomoses within the body, e.g., the gastrointestinal tract. Such devices and techniques facilitate faster and less-expensive treatments for chronic diseases such as obesity and diabetes. Such techniques also reduce the time and pain associated with palliative treatments for diseases such as cancers, such as stomach or colon cancer.

More specifically, the invention provides various systems, devices, and methods for the delivery, deployment, and positioning of magnetic compression devices at a desired site so as to improve the accuracy of anastomoses creation between tissues, organs, or the like. The systems, devices, and methods of the present invention include, but are not limited to, various access devices for accessing a hollow body of the patient, such as a gall bladder, and securing positioning of the access device for the subsequent placement of one of a pair of magnetic anastomosis compression devices. The systems, devices, and methods of the present invention further include various delivery devices for delivering at least one of the pair of magnetic anastomosis compression devices to the target site, wherein, in some instances, a delivery device consistent with the present disclosure may assist in the deployment of at least one of the pair of magnetic anastomosis compression devices and subsequent securing to the target site and/or coupling the pair of magnetic anastomosis compression devices to one another. The systems, devices, and methods of the present invention include various embodiments of magnetic anastomosis compression devices and various designs for transitioning from a compact delivery configuration to a larger deployed configuration, generally by way of self-assembling design.

For example, in one aspect, the invention provides a system including a delivery device for introducing and delivering, via a minimally-invasive technique, a pair of magnetic assemblies between adjacent organs to bridge walls of tissue of each organ together to thereby form a passage therebetween (i.e., an anastomosis). The delivery device is particularly useful in delivering the pair of magnetic assemblies to a target site within the gastrointestinal tract to thereby form anastomosis between gastric and gall bladder walls to provide adequate drainage from the gallbladder when blockage is occurring (due to disease or other health-related issues).

In particular, in the embodiments described herein, the system generally includes a single scope, such as an endoscope, laparoscope, catheter, trocar, or other access device, through which a delivery device is advanced to a target site for delivering and positioning a pair of magnetic assemblies for subsequent formation of anastomosis at the target site. In particular, the delivery device comprises an elongate hollow body, such as a catheter, shaped and/or sized to fit within the scope. The delivery device includes a working channel in which a pair of magnetic assemblies is loaded. The delivery device further includes a distal end configured to pierce, or otherwise penetrate, through tissue. For example, the distal end may have a sharp tip for piercing tissue and/or may utilize energy to penetrate through tissue (i.e., a hot tip). The body of the delivery device further includes a slot or opening adjacent to the distal tip. The slot is shaped and/or sized to receive the magnetic assemblies therethrough, such that the magnetic assemblies pass through the working channel and exit the delivery device via the slot. The delivery device further includes a placement member, generally in the form of a wire or the like, that is releasably coupled to one or both of the magnetic assemblies and provide a means of deploying the magnetic assemblies from the distal end of the delivery device via the slot.

During a procedure, a surgeon or other trained medical professional may advance a scope (e.g., endoscope) within a hollow body of the patient and position the scope at a desired anatomical location for formation of the anastomosis based on either a visual depiction of the location of the target site as provided by an imaging modality providing a medical imaging procedure (e.g., ultrasound (US), wavelength detection, X-ray-based imaging, illumination, computed tomography (CT), radiography, and fluoroscopy, or a combination thereof). The surgeon may advance the distal tip of the delivery device through adjacent walls of a pair of organs (i.e., through a wall of the duodenum and a wall of the common bile duct). Upon advancing distal end, including the slot, into the first organ (i.e., common bile duct), the surgeon may utilize the placement member to manually deliver and deploy a first magnetic assembly into the first organ via the slot. It should be noted that each magnetic assembly comprises a pair of magnetic segments generally arranged in a linear alignment with one another (e.g., aligned in an end-to-end fashion) and coupled together via a flexible exoskeleton element, wherein the segments are spaced apart via a central portion of the exoskeleton. The exoskeleton may be made from a resilient material that will retain its shape after deformation, such as a polymer or metal alloy. As such, deployment of the first magnetic assembly results in the pair of magnetic segments to exit the slot on opposite respective sides of the body of the delivery device while the central portion of the exoskeleton remains within the slot. In other words, the slot extends entirely through the body of the delivery device, from one side to the other.

At this point, the surgeon need only pull back upon the delivery device until the first magnetic assembly engages the tissue of the first organ and the majority of the slot is positioned within the second organ. The surgeon is able to then deliver and deploy the second magnetic assembly into the second organ (i.e., the duodenum). The second magnetic assembly deploys in a similar fashion as the first magnetic assembly, in that magnetic segments of the second magnetic assembly exit the slot on opposite respective sides of the body of the delivery device while a central portion of an exoskeleton remains within the slot. In turn, the first and second magnetic assemblies are substantially aligned with one another and, due to attractive magnetic forces, the first and second magnetic assemblies will couple to one another. The distal end of the delivery device is comprised of two halves that, when in a default state, form a relatively uniform tip shape. However, the distal end comprises a deformable material (i.e., shape memory material), such that, upon application of sufficient force, the two halves will split apart. As such, once both the first and second magnetic assemblies have been delivered and are effectively coupled to one another (but are still retained within the slot), the surgeon need only pull back on the delivery device which then causes the magnets to make contact with the distal tip and force the two halves of the distal tip to split apart, allowing the distal end of the delivery device to be withdrawn from the target site while the pair of magnetic assemblies remain in place. The pair of magnetic assemblies compress the walls of each respective organ therebetween, subsequently forming an anastomosis between the organs (i.e., anastomosis between the duodenum and the common bile duct).

As such, upon deployment, each magnetic assembly has a width and a length generally corresponding to a width of a respective segment and a length that is approximately twice the length of each segment. As a result, the pair of magnetic assemblies, when coupled to one another, generally form a substantially linear package and the resulting anastomosis formed may generally be rectangular in shape, but may naturally form a round or oval shape. The resulting anastomosis may have a 1:1 aspect ratio relative to the dimensions of the magnetic assemblies. However, the present invention allows for larger aspect ratios (i.e., a larger anastomosis to form relative to the dimensions of the magnetic assemblies). In particular, prior art systems and methods that include the use of magnets for creating anastomosis are generally limited based on the dimensions of the working channel of the scope or catheter used for delivering such magnets, which, in turn, limits the resulting size of the anastomosis. However, the magnetic assembly design of the present invention overcomes such limitations. For example, the design of the magnetic assembly of the present invention, notably the coupling of multiple magnetic segments to one another via an exoskeleton, allow for any number of segments to be included in a single assembly, and thus the resulting anastomosis has a greater size relative to the dimensions of the working channel of the scope. For example, in some embodiments, the resulting anastomosis may include an aspect ratio in the range of 2:1 to 10:1 or greater.

Accordingly, the delivery device of the present disclosure produces a low-profile linear anastomosis that would allow certain complications, particularly those associated with blockage of the common bile duct, to be mitigated. In particular, patients experiencing a blockage of the common bile duct often undergo some sort of procedure to either remove the blockage or allow procedure is a sphincterotomy, or some sort of draining stent placement procedure. There are procedures which present decompression of the bile duct in a traditional way, but are not possible in a minimally noninvasive manner. Such procedures include, for example, a sphincterotomy, which is not possible due to inability to cannulate the common bile duct, inability to account for anatomical alterations, particularly when during heavily diseased states. Utilizing the magnetic closure force profile of the present invention would allow minimal bleeding and create a semi-permanent slit profile. This slit profile would help to resist "sump syndrome" and help to create a drainage point which would remain effectively infection free.

BRIEF DESCRIPTION OF THE DRAWINGS

Features and advantages of the claimed subject matter will be apparent from the following detailed description of embodiments consistent therewith, which description should be considered with reference to the accompanying drawings.

FIG. 9 illustrates the use of monopolar energy for piercing and accessing the gallbladder.

FIG. 10 illustrates the use of a fine aspiration needle (FNA) for piercing and accessing the gallbladder.

FIG. 11 illustrates the use of a corkscrew-type needle for piercing and accessing the gallbladder.

FIG. 12 illustrates the use of a guidewire passed through the bile duct.

FIG. 14 illustrates a T-bar member. FIG. 15 illustrates a nitinol coil (e.g., "pig tail"). FIG. 16 illustrates a balloon member of a catheter. FIG. 17 illustrates a malecot catheter.

FIGS. 20A, 20B, and 20C illustrate a method of accessing the gallbladder, via endoscopic ultrasound guided access and utilizing a hot insertion tube emitting monopolar energy, and subsequently delivering a magnetic anastomosis device within the gallbladder via the hot tube.

FIGS. 21A, 21B, 21C, 21D, and 21E illustrate a technique of accessing the gallbladder and delivering a pair of magnetic anastomosis devices for the formation of an anastomosis the gallbladder tissue and adjacent tissue.

FIGS. 25A, 25B, 25C, 25D, 25E illustrate a technique of accessing the gallbladder and delivering a pair of magnetic anastomosis devices for the formation of an anastomosis the gallbladder tissue and adjacent tissue (i.e., stomach or duodenum tissue).

FIG. 45 provides a listing of working channel sizes that are currently available and would be considered usable/feasible to deploy a magnetic array with a cage to produce an anastomosis.

Figure 1:
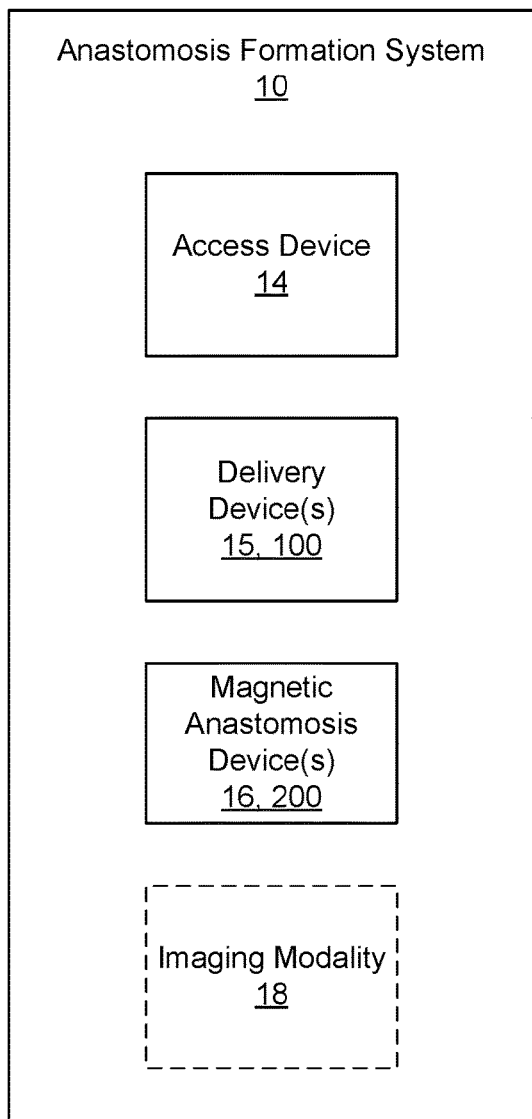
FIG. 1 is a schematic illustration of an anastomosis formation system consistent with the present disclosure.

For a thorough understanding of the present disclosure, reference should be made to the following detailed description, including the appended claims, in connection with the above-described drawings. Although the present disclosure is described in connection with exemplary embodiments, the disclosure is not intended to be limited to the specific forms set forth herein. It is understood that various omissions and substitutions of equivalents are contemplated as circumstances may suggest or render expedient.

DETAILED DESCRIPTION

The present invention provides improved devices and techniques for minimally-invasive formation of anastomoses within the body, e.g., the gastrointestinal tract. Such devices and techniques facilitate faster and less-expensive treatments for chronic diseases such as obesity and diabetes. Such techniques also reduce the time and pain associated with palliative treatments for diseases such as cancers, such as stomach or colon cancer.

The system generally includes an access device configured to be provided within a hollow body of a patient and assist in the formation of an anastomosis at a target site (a desired anatomical location) within the hollow body for formation of an anastomosis between a first portion of tissue of the hollow body at the target site and a second portion of tissue of the hollow body. The access device is configured to provide access to the first and second portions of tissue of the hollow body and further deliver and position first and second implantable magnetic anastomosis devices relative to the first and second portions of tissue or adjacent tissue for the formation of an anastomosis between tissues at the target site. The first and second implantable magnetic anastomosis devices are configured to be magnetically attracted to one another through a defined tissue area of the combined thickness of a wall of the tissues at the target site and exert compressive forces on the defined area to form the anastomosis.

The systems, devices, and methods of the present invention include, but are not limited to, various access devices for accessing a hollow body of the patient, such as a gall bladder, and securing positioning of the access device for the subsequent placement of one of a pair of magnetic anastomosis compression devices. The systems, devices, and methods of the present invention further include various delivery devices for delivering at least one of the pair of magnetic anastomosis compression devices to the target site, wherein, in some instances, a delivery device consistent with the present disclosure may assist in the deployment of at least one of the pair of magnetic anastomosis compression devices and subsequent securing to the target site and/or coupling the pair of magnetic anastomosis compression devices to one another. The systems, devices, and methods of the present invention include various embodiments of magnetic anastomosis compression devices and various designs for transitioning from a compact delivery configuration to a larger deployed configuration, generally by way of self-assembling design.

More specifically, the invention provides a system including a delivery device for introducing and delivering, via a minimally-invasive technique, a pair of magnetic assemblies between adjacent organs to bridge walls of tissue of each organ together to thereby form a passage therebetween (i.e., an anastomosis). The delivery device is particularly useful in delivering the pair of magnetic assemblies to a target site within the gastrointestinal tract to thereby form anastomosis between gastric and gall bladder walls to provide adequate drainage from the gallbladder when blockage is occurring (due to disease or other health-related issues).

Accordingly, the invention provides improved devices and techniques for minimally invasive formation of anastomoses within the body, e.g., the gastrointestinal tract. Such devices and techniques facilitate faster and less-expensive treatments for chronic diseases such as obesity and diabetes. Such techniques also reduce the time and pain associated with palliative treatments for diseases such as cancers, such as stomach or colon cancer.

FIG. 1 is a schematic illustration of an anastomosis formation system 10 for providing improved placement of magnetic anastomosis devices at a desired site so as to improve the accuracy of anastomoses creation between tissues within a patient 12. The system 10 generally includes an access device 14, a delivery device 15, 100, magnetic anastomosis devices 16, 200, and an imaging modality 18.

The access device 14 may generally include a scope, including, but not limited to, an endoscope, laparoscope, catheter, trocar, or other delivery device. For most applications described herein, the access device 14 is an endoscope, including a delivery needle configured to deliver the magnetic anastomosis devices 16, 200. Accordingly, the system 10 of the present disclosure relies on a single endoscope 14 for the delivery of the two magnetic devices 16, 200. As will be described in greater detail herein, a surgeon may advance the endoscope 14 within a hollow body of the patient 12 and position the endoscope 14 at the desired anatomical location for formation of the anastomosis based on a visual depiction of the location of the target site as provided by an imaging modality. For example, the imaging modality may include a display in which an image, or other visual depiction, is displayed to the surgeon illustrating a target site when performing a medical imaging procedure, including, but not limited to, ultrasound (US), wavelength detection, X-ray-based imaging, illumination, computed tomography (CT), radiography, and fluoroscopy, or a combination thereof. The surgeon may then rely on such a visual depiction when advancing the endoscope through the hollow body so as to position the access device 14 at a portion of tissue adjacent to the other portion of tissue at the target site, thereby ensuring the placement of the magnetic devices 16, 200 is accurate.

It should be noted that the hollow body through which the access device 14 may pass includes, but is not limited to, the stomach, gallbladder, pancreas, duodenum, small intestine, large intestine, bowel, vasculature, including veins and arteries, or the like.

Figure 2:
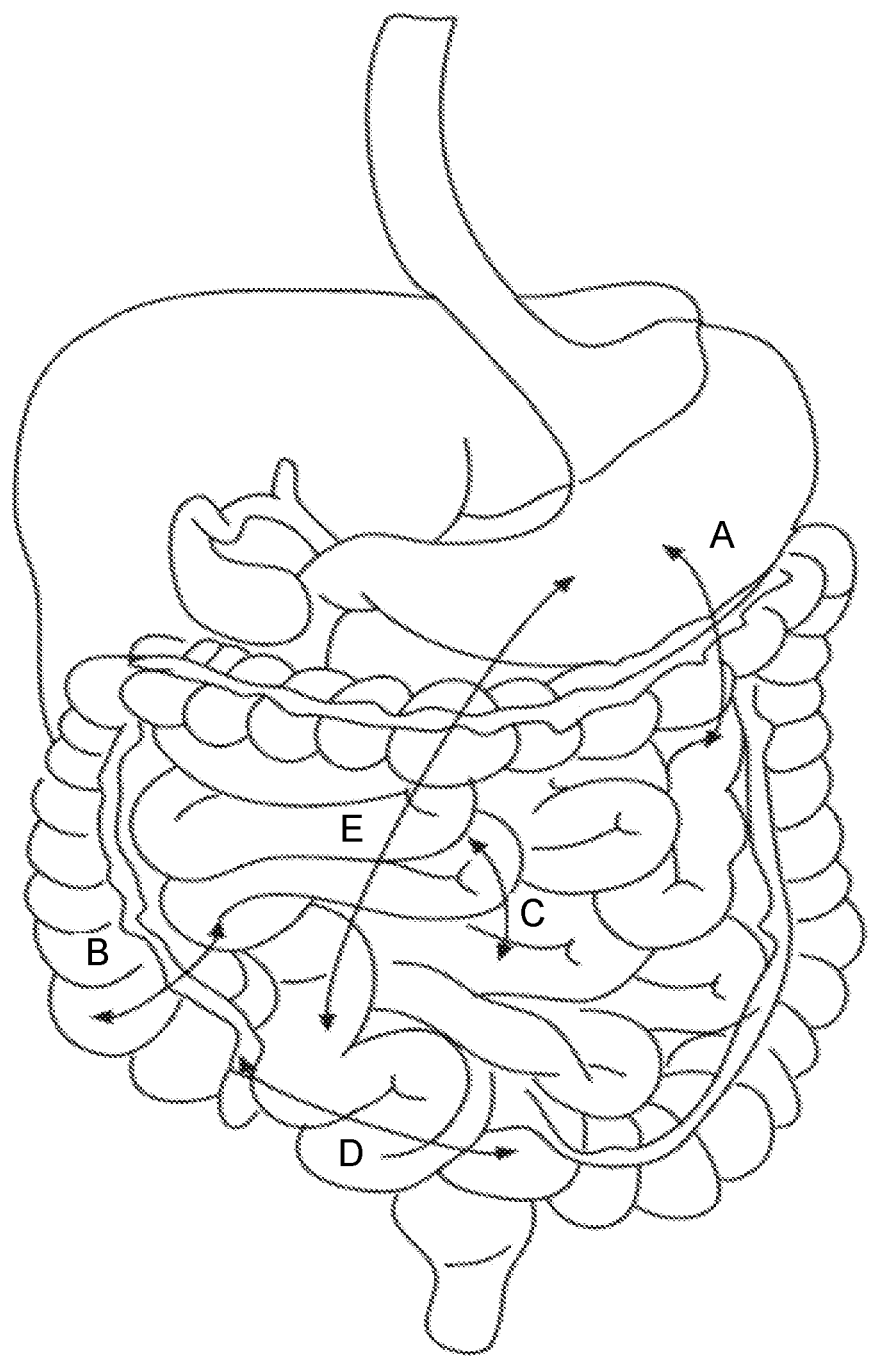
FIG. 2 shows several potential anatomical targets for anastomosis formation, where arrow A is stomach to small intestine, arrow B is small intestine to large intestine, arrow C is small intestine to small intestine, arrow D is large intestine to large intestine, and arrow E is stomach to large intestine.

In some embodiments, self-assembling magnetic devices are used to create a bypass in the gastrointestinal tract. Such bypasses can be used for the treatment of a cancerous obstruction, weight loss or bariatrics, or even treatment of diabetes and metabolic disease (i.e. metabolic surgery). FIG. 2 illustrates the variety of gastrointestinal anastomotic targets that may be addressed with the devices of the invention, such targets include stomach to small intestine (A), stomach to large intestine (E), small intestine to small intestine (C), small intestine to large intestine (B), and large intestine to large intestine (D). Accordingly, the invention provides improved devices and techniques for minimally-invasive formation of anastomoses within the body, e.g., the gastrointestinal tract. Such devices and techniques facilitate faster and less-expensive treatments for chronic diseases such as obesity and diabetes. Such techniques also reduce the time and pain associated with palliative treatments for diseases such as cancers, such as stomach or colon cancer.

For example, if the hollow body through which the access device 14 may pass is a bowel of the patient, the first portion may be a distal portion of the bowel and the second portion may be a proximal portion of the bowel. The bowel includes any segment of the alimentary canal extending from the pyloric sphincter of the stomach to the anus. In some embodiments, an anastomosis is formed to bypass diseased, mal-formed, or dysfunctional tissues. In some embodiments, an anastomosis is formed to alter the "normal" digestive process in an effort to diminish or prevent other diseases, such as diabetes, hypertension, autoimmune, or musculoskeletal disease. It should be noted that the system may be used for the formation of an anastomosis between a first portion of tissue of the hollow body at the target site and an adjacent tissue of a second hollow body (e.g., portal between the stomach and the gallbladder, the duodenum and the gallbladder, stomach to small intestine, small intestine to large intestine, stomach to large intestine, etc.).

Figure 3:
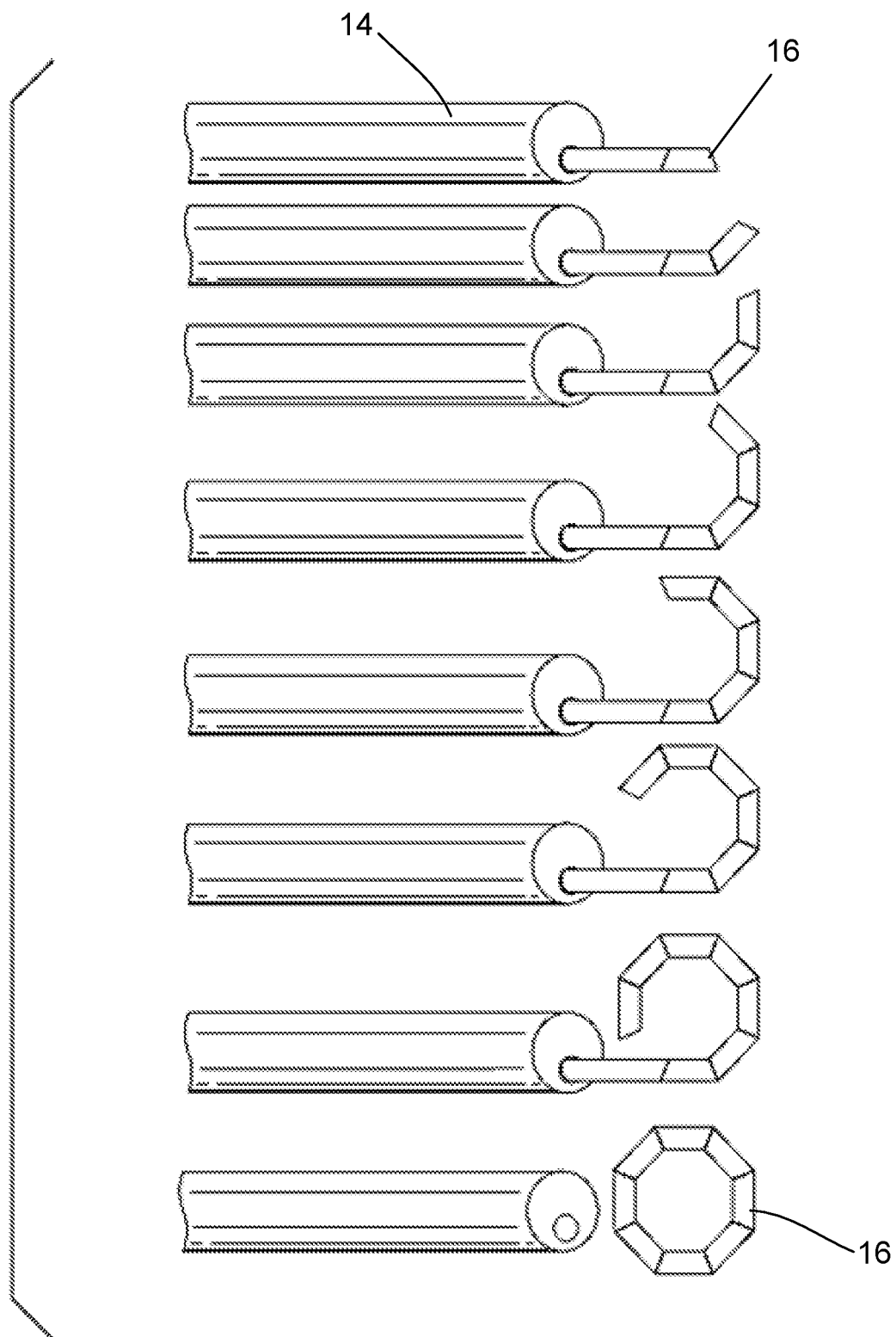
FIG. 3 shows an exemplary magnetic anastomosis device delivered through an endoscope instrument channel such that the individual magnet segments self-assemble into a larger magnetic structure—in this particular case, an octagon.

In an endoscopic procedure, the self-assembling magnetic devices can be delivered using a single endoscope 14. Deployment of a magnetic device 16 is generally illustrated in FIG. 3. As shown, exemplary magnetic anastomosis devices 16 may be delivered through an endoscope 14 such that individual magnet segments self-assemble into a larger magnetic structure—in this particular case, an octagon. When used with the techniques described herein, the devices 16 allow for the delivery of a larger magnetic structures than would otherwise be possible via a small delivery conduit, such as in a standard endoscope, if the devices were deployed as a completed assembly. Larger magnet structures, in turn, allow for the creation of larger anastomoses that are more robust, and achieve greater surgical success. For example, in some cases, resulting anastomosis may have a 1:1 aspect ratio relative to the final dimensions of the assembled magnetic devices. However, the present invention allows for larger aspect ratios (i.e., a larger anastomosis to form relative to the dimensions of the magnetic assemblies). In particular, prior art systems and methods that include the use of magnets for creating anastomosis are generally limited based on the dimensions of the working channel of the scope or catheter used for delivering such magnets, which, in turn, limits the resulting size of the anastomosis. However, the magnetic assembly design of the present invention overcomes such limitations. For example, the design of the magnetic assembly of the present invention, notably the coupling of multiple magnetic segments to one another via an exoskeleton, allow for any number of segments to be included in a single assembly, and thus the resulting anastomosis has a greater size relative to the dimensions of the working channel of the scope. For example, in some embodiments, the resulting anastomosis may include an aspect ratio in the range of 2:1 to 10:1 or greater. Such aspect ratios are described in greater detail with regard to FIGS. 44A, 44B, 44C, and 44D.

Because the magnetic devices are radiopaque and echogenic, the devices can be positioned using fluoroscopy, direct visualization (trans-illumination or tissue indentation), and ultrasound, e.g., endoscopic ultrasound. The devices 16 can also be ornamented with radiopaque paint or other markers to help identify the polarity of the devices during placement.

The magnetic anastomosis devices 16 of the invention generally comprise magnetic segments that can assume a delivery conformation and a deployed configuration. The delivery configuration is typically linear so that the device can be delivered to a tissue via a laparoscopic "keyhole" incision or with delivery via a natural pathway, e.g., via the esophagus, with an endoscope 14 or similar device. Additionally, the delivery conformation is typically somewhat flexible so that the device can be guided through various curves in the body. Once the device is delivered, the device will assume a deployed configuration of the desired shape and size by converting from the delivery configuration to the deployed configuration automatically. The self-conversion from the delivery configuration to the deployment configuration is directed by coupling structures that cause the magnetic segments to move in the desired way without intervention. Exemplary self-assembling magnetic anastomosis devices 16, such as self-closing, self-opening, and the like, are described in U.S. Pat. Nos. 8,870,898, 8,870,899, 9,763,664, and U.S. patent application Ser. No. 14/805,916, filed Jul. 22, 2015, the contents of each of which are incorporated by reference herein in their entirety.

Figure 4A:
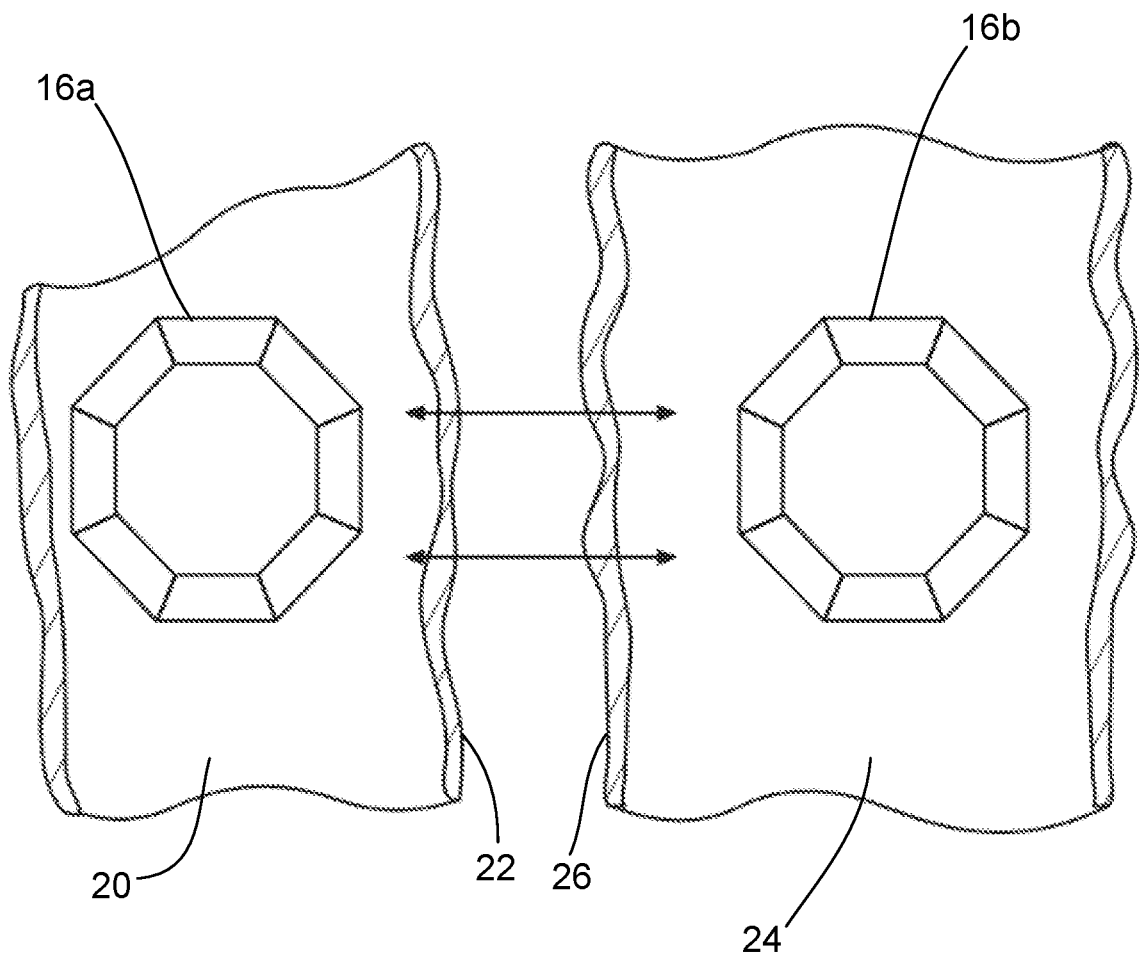
FIG. 4A depicts two magnetic anastomosis devices attracting each other through tissue. As shown, the devices each comprise eight magnetic segments, however alternate configurations are possible. Once the two devices mate, the tissue that is trapped between the devices will necrose, causing an anastomosis to form. Alternatively, the tissue bound by the devices may be perforated after the devices mate to create an immediate anastomosis.

In general, as shown in FIG. 4A, a magnetic anastomosis procedure involves placing a first and a second magnetic structures 16a, 16b adjacent to first and second portions 20, 24 of tissues 22, 26, respectively, thus causing the tissues 22 and 26 to come together. Once the two devices 16a, 16b are brought into proximity, the magnetic structures 16a, 16b mate and bring the tissues 22, 26 together. With time, an anastomosis of the size and shape of the devices 16a, 16b will form and the devices will fall away from the tissue. In particular, the tissues 22, 26 circumscribed by the devices will be allowed to necrose and degrade, providing an opening between the tissues.

Figure 4B:
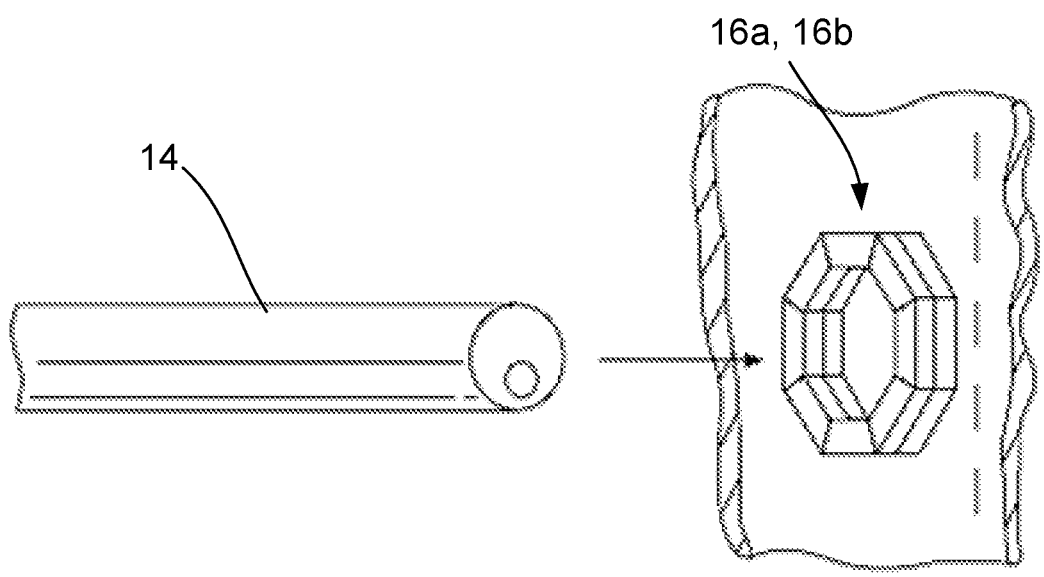
FIG. 4B shows the two magnetic anastomosis devices coupled together by magnetic attraction, capturing the intervening tissue. In some instances, the endoscope can be used to cut through the circumscribed tissue.

Alternatively, because the mated devices 16a and 16b create enough compressive force to stop the blood flow to the tissues 22, 26 trapped between the devices, a surgeon may create an anastomosis by making an incision in the tissues 22, 26 circumscribed by the devices, as shown in FIG. 4B.

In yet another embodiment, as will be described in greater detail herein, and shown in FIGS. 43A-43I, a surgeon may first cut into, or pierce, the tissues 22, 26, and then deliver a magnetic device 16a, 200a into a portion 20 of the hollow body so as to place device 16a, 200a around the incision on tissue 22. The surgeon may then place device 16b, 200b into portion 24 of the hollow body so as to deliver device 16b, 200b around the incision on tissue 26, and then allow the devices 16a, 200a and 16b, 200b to couple to one another, so that the devices 16a, 16b (200a, 200b) circumscribe the incision. As before, once the devices 16a, 16b (200a, 200b) mate, the blood flow to the incision is quickly cut off.

While the figures and structures of the disclosure are primarily concerned with annular or polygonal structures, it is to be understood that the delivery and construction techniques described herein can be used to make a variety of deployable magnetic structures. For example, self-assembling magnets can re-assemble into a polygonal structure such as a circle, ellipse, square, hexagon, octagon, decagon, or other geometric structure creating a closed loop. The devices may additionally include handles, suture loops, barbs, and protrusions, as needed to achieve the desired performance and to make delivery (and removal) easier. Yet still, in other embodiments, such as magnetic assembly 200 of FIG. 42, a magnetic assembly may comprises a pair of magnetic segments generally arranged in a linear alignment with one another (e.g., aligned in an end-to-end fashion) and coupled together via a flexible exoskeleton element. Such an embodiment will be described in greater detail herein.

Figure 5A:
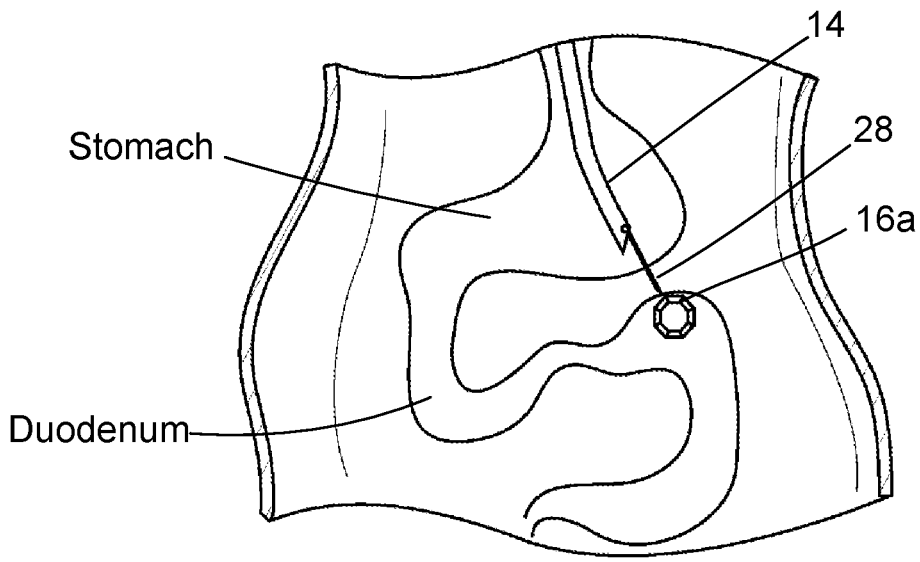
FIG. 5A shows the needle delivering a first magnetic device into a first portion of the hollow body at the target site.
Figure 5B:
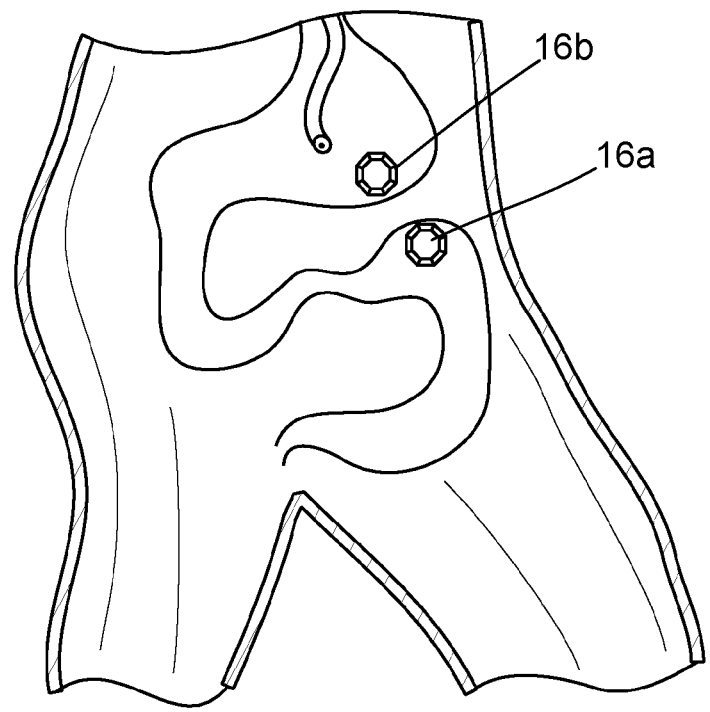
FIG. 5B shows subsequent deployment to of a second magnetic device into a second portion of the hollow body adjacent to the target site.

As previously described, the self-assembling magnetic anastomosis devices can be delivered to the target site via the access device 14. For example, as shown in FIG. 5A, the access device 14 may include a delivery needle 28 (e.g., an aspiration needle) used to deliver the first magnetic anastomosis device 16a into the lower small intestine (through the puncture), which is then followed by deployment to of a second magnetic device 16b into the upper small intestine at a location on the tissue adjacent to the target site (shown in FIG. 5B). It should be noted that the delivery can be guided with fluoroscopy or endoscopic ultrasound. Following self-assembly, these small intestine magnetic devices 16a, 16b couple to one another (e.g., magnetically attracted to one another) through a defined tissue area of the combined thickness of a wall of the tissues at the target site and exert compressive forces on the defined area to form the anastomosis.

Figure 6A:
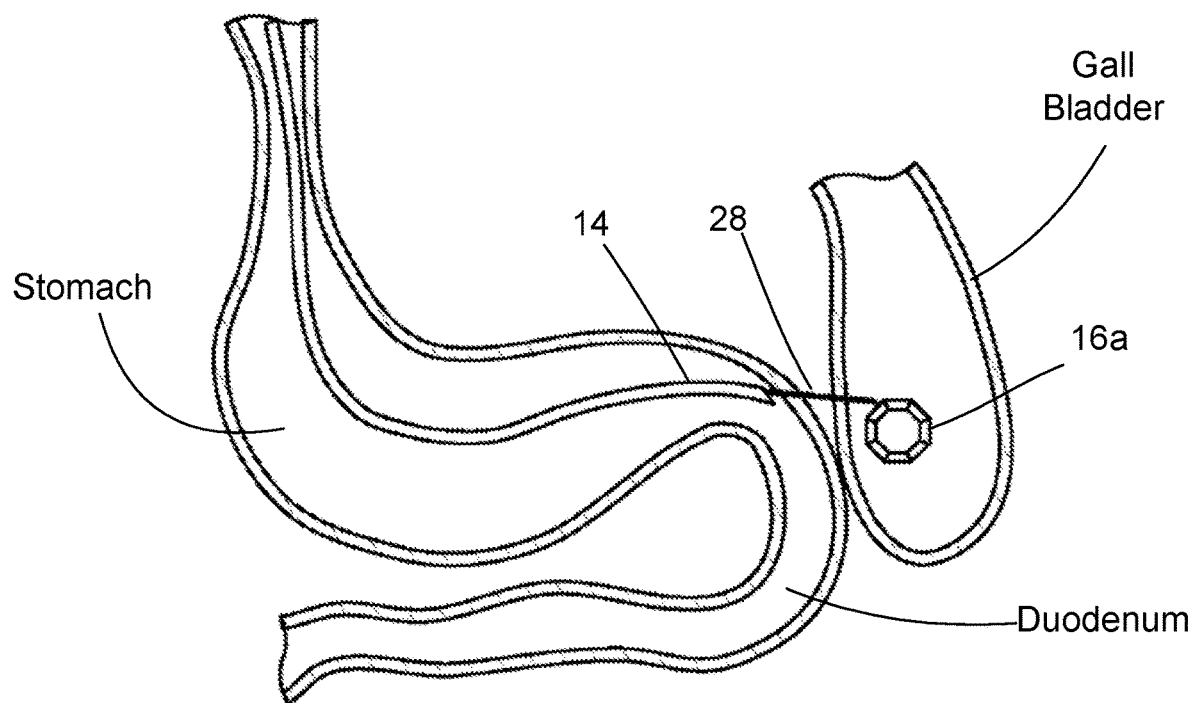
FIG. 6A shows endoscopic ultrasound guided needle delivery of a magnet assembly into the gallbladder which then couples with a second magnet assembly in the stomach or duodenum as shown in FIG. 6B.
Figure 6B:
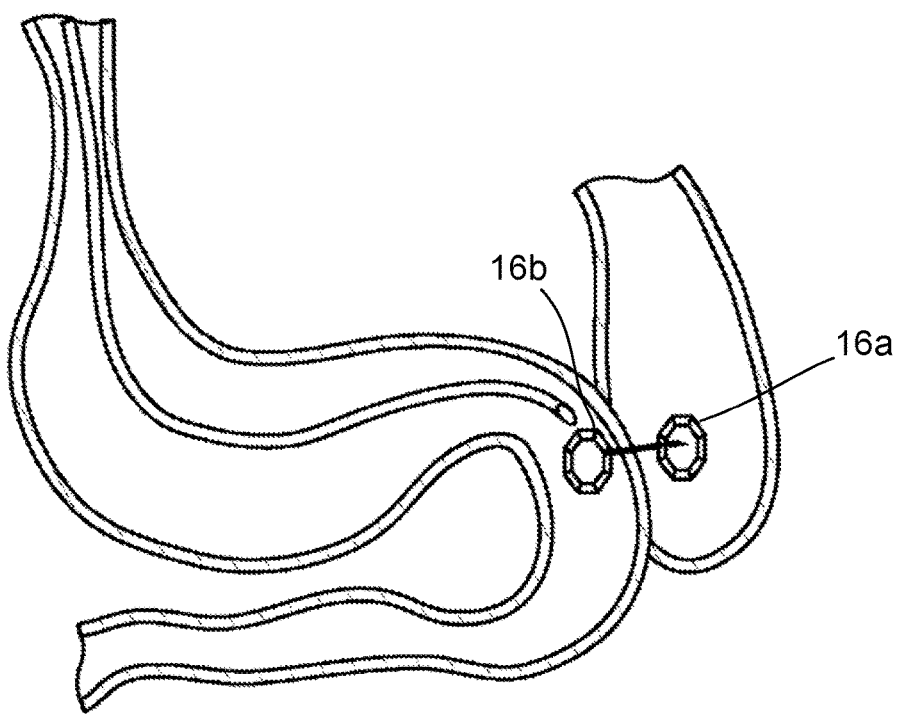

FIG. 6A shows endoscopic ultrasound guided needle delivery of a magnet assembly into the gallbladder which then couples with a second magnet assembly in the stomach or duodenum as shown in FIG. 6B. Accordingly, the described procedures may also be used with procedures that remove or block the bypassed tissues. For example, endoscopic ultrasound (EUS) can be used to facilitate guided transgastric or transduodenal access into the gallbladder for placement of a self-assembling magnetic anastomosis device. Once gallbladder access is obtained, various strategies can be employed to maintain a patent portal between the stomach and the gallbladder or the duodenum and the gallbladder. In another embodiment, gallstones can be endoscopically retrieved and fluid drained. For example, using the described methods, an anastomosis can be created between the gallbladder and the stomach. Once the gallbladder is accessed in a transgastric or transduodenal fashion, the gallstones can be removed. Furthermore, the gallbladder mucosa can be ablated using any number of modalities, including but not limited to argon plasma coagulation (APC), photodynamic therapy (PDT), sclerosant (e.g. ethanolamine or ethanol).

Figure 7:
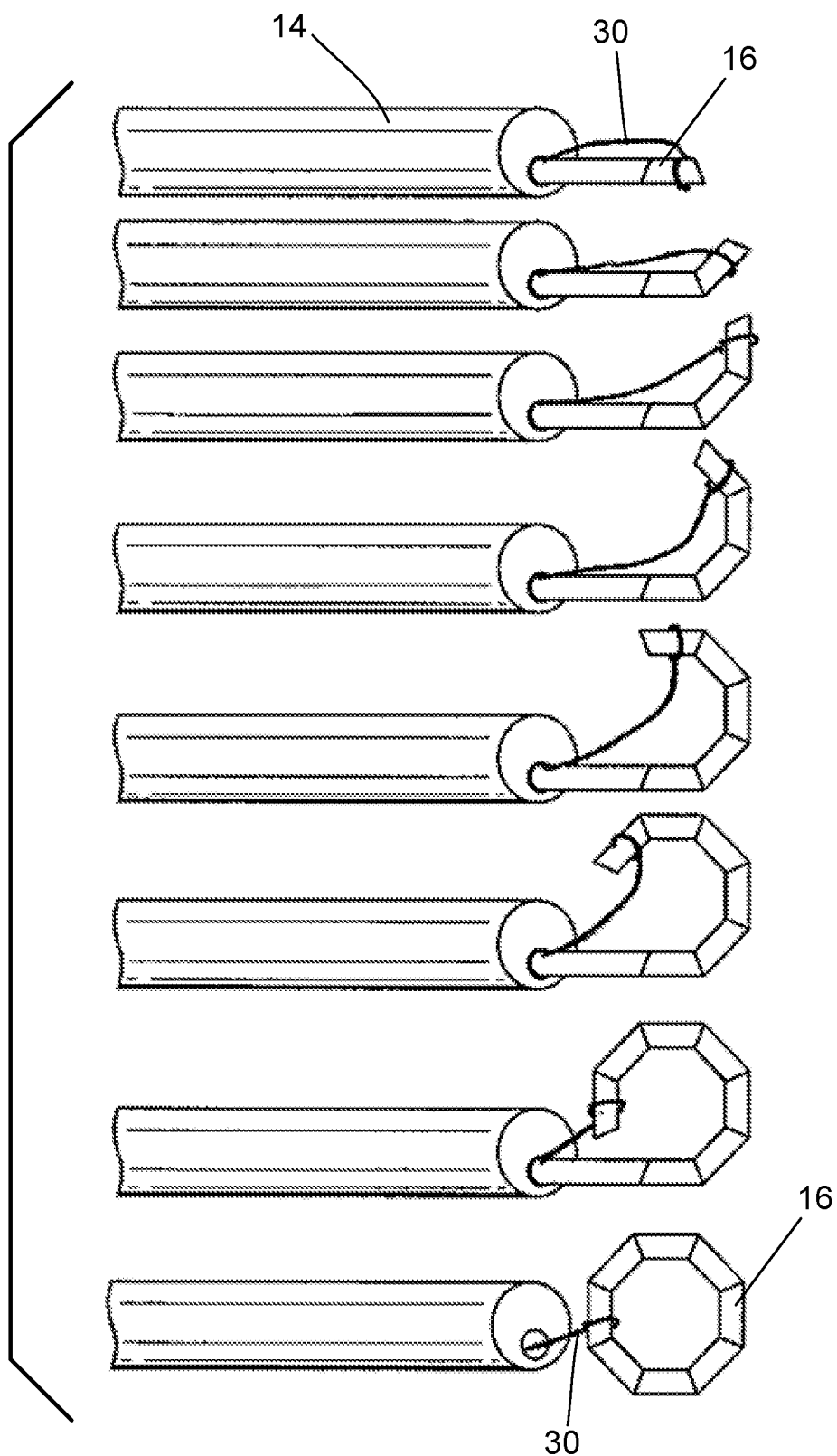
FIG. 7 illustrates a single guide element for deploying and manipulating a magnetic anastomosis device.
Figure 8A:
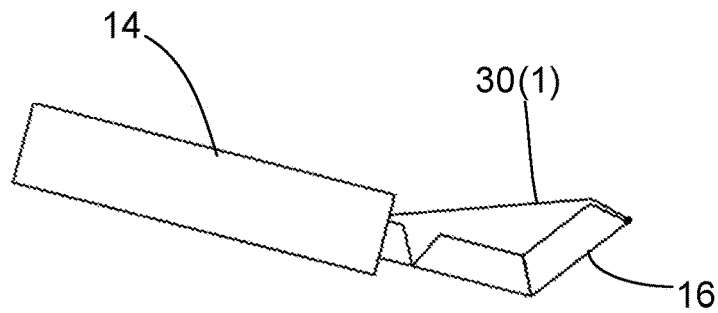
FIGS. 8A, 8B, 8C, 8D, 8E, and 8F each depict the deployment of the self-closing magnetic anastomosis device with a plurality of guide elements.
Figure 8B:
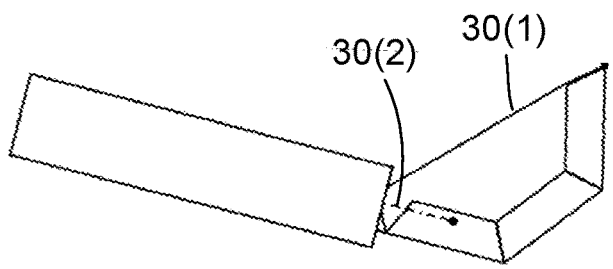
Figure 8C:
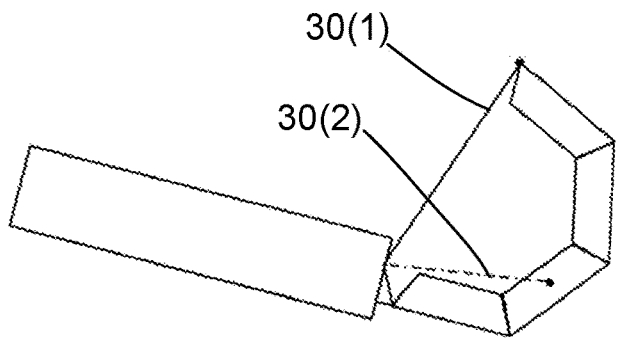
Figure 8D:
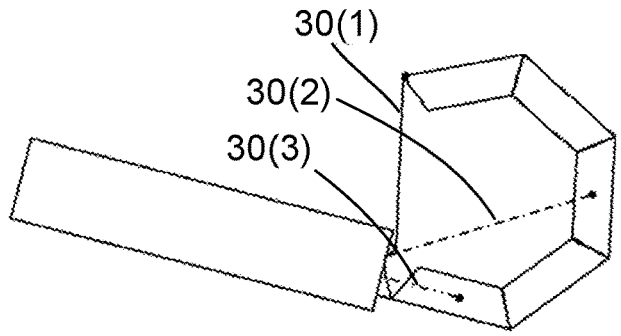
Figure 8E:
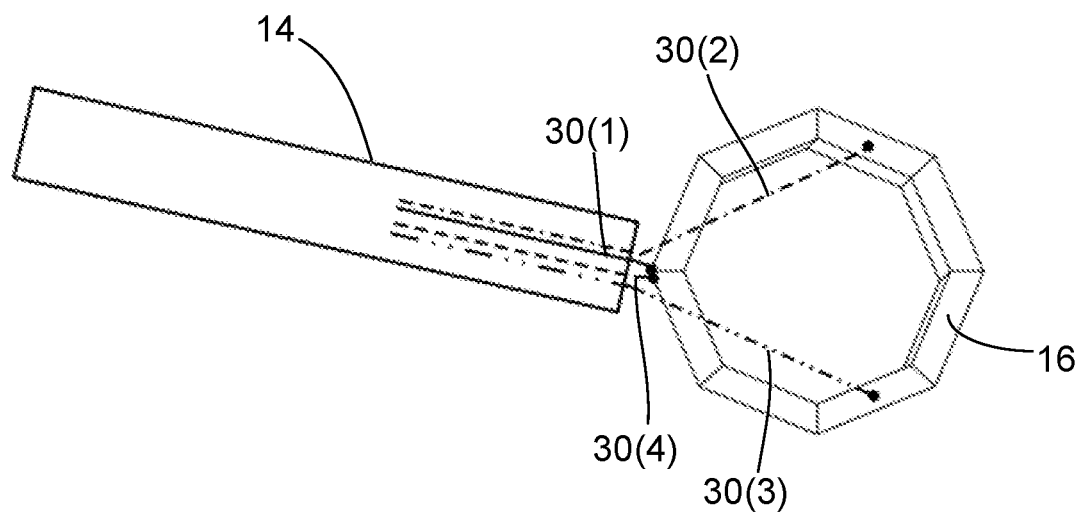
Figure 8F:
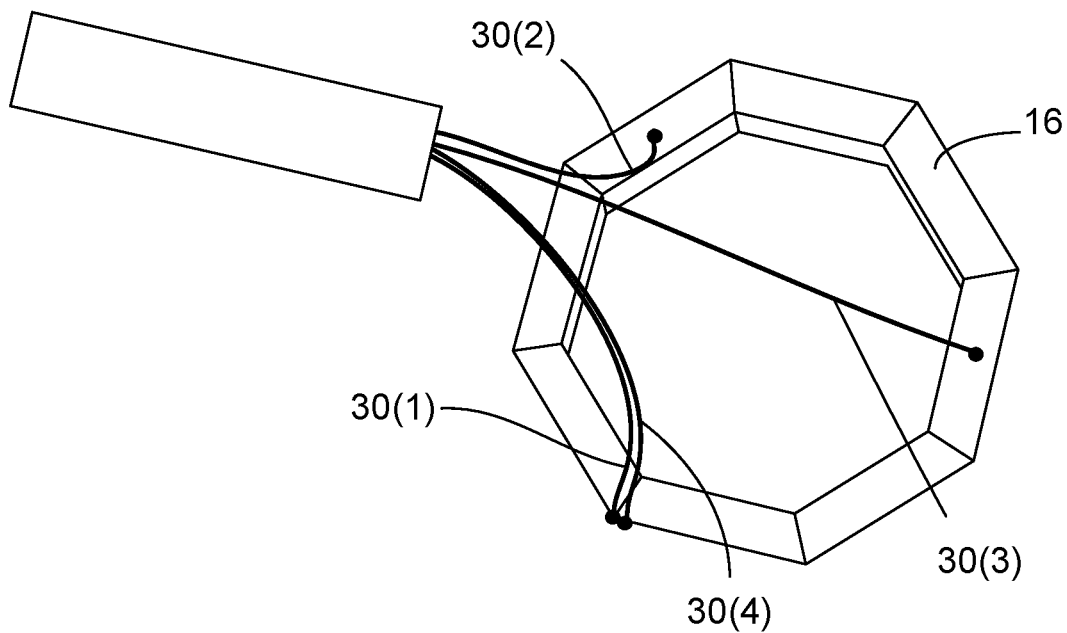

FIG. 7 illustrates a single guide element 30 for deploying and manipulating a magnetic anastomosis device 16. For example, once the self-assembling magnetic device has been delivered to a tissue, it is beneficial to be able to manipulate the location of the device 16. While the device 16 can be manipulated with conventional tools such as forceps, it is often simpler to manipulate the location of the deployed device 16 with a guide element 30, such as a suture or wire. As shown in FIGS. 7 and 8A-8F, a variety of attachment points can be used to provide control over the location and deployment of a self-assembling magnetic anastomosis device 16. For example, as shown in FIG. 7, the guide element 30 may be coupled to a single distal segment such that, upon self-assembly, the single distal segment results in an attachment point that provides translational freedom of movement. It is also notable that the configuration shown in FIG. 7 also allows a closing force to be applied to the distal-most segment. That is, in the event that one or more segments should become entangled with tissue, or otherwise prevented from self-assembling, a proximal pulling force with the guide element 30 can help the device 16 to complete self-assembly. Once self-assembly is completed, the device 16 can be positioned with the guide element 30 to be mated with another device (not shown) to form an anastomosis, as described above. While it is not shown in FIG. 7, it is envisioned that additional structures, such as a solid pusher or a guide tube can be used to deploy the device 16 in the desired location.

The guide element 30 can be fabricated from a variety of materials to achieve the desired mechanical properties and bio-compatibility. The guide element 30 may be constructed from metal, e.g., wire, e.g., stainless steel wire, or nickel alloy wire. The guide element may be constructed from natural fibers, such as cotton or an animal product. The guide element may be constructed from polymers, such as biodegradable polymers, such as polymers including repeating lactic acid, lactone, or glycolic acid units, such as polylactic acid (PLA). The guide element may also be constructed from high-tensile strength polymers, such as Tyvek™ (high density polyethylene fibers) or Kevlar™ (para-aramid fibers). In an embodiment, guide element 30 is constructed from biodegradable suture, such as VICRYL™ (polyglactin 910) suture available from Ethicon Corp., Somerville, N.J.

In some embodiments, a magnetic anastomosis device 16 may include multiple guide elements 30. For example, as shown in FIGS. 8A, 8B, 8C, 8D, 8E, and 8F, a variety of attachment points can be used to provide control over the location and deployment of a self-assembling magnetic anastomosis device 16. As shown, four guide elements 30(1)-30(4) may be coupled to four separate segments of the device 16, respectively. Each guide element may include a distal end coupled to a respective portion of the anastomosis device, and a proximal end that can be manipulated (i.e., increased or decreased tension) to thereby manipulate the positioning and orientation of the anastomosis device once it has self-assembled into the predetermined shape (i.e., a polygon). For example, as shown, guide element 30(1) is coupled to the most distal end segment, guide elements 30(2) and 30(3) are coupled to middle segments (segments between the most distal end segment and most proximal end segment), and guide element 30(4) is coupled to the most proximal end segment.

Figure 9:
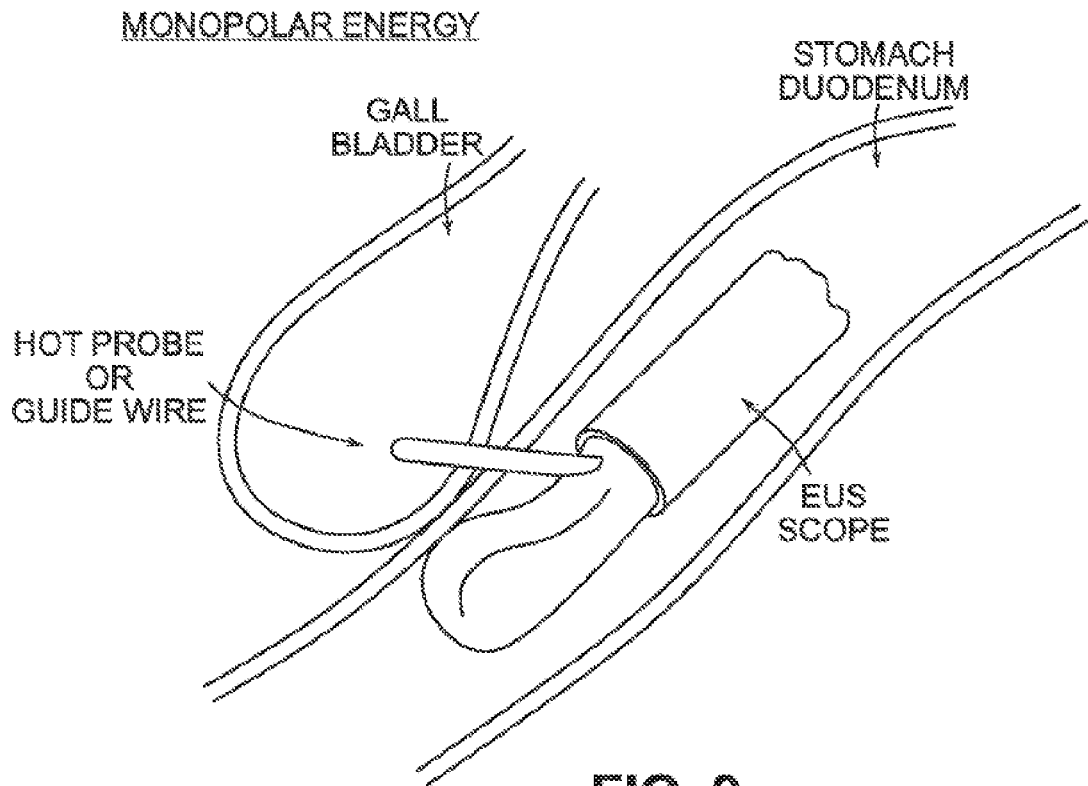
FIGS. 9, 10, 11, and 12 illustrate various methods of accessing the target site, specifically accessing a gallbladder via an endoscopic ultrasound guided procedure.
Figure 10:
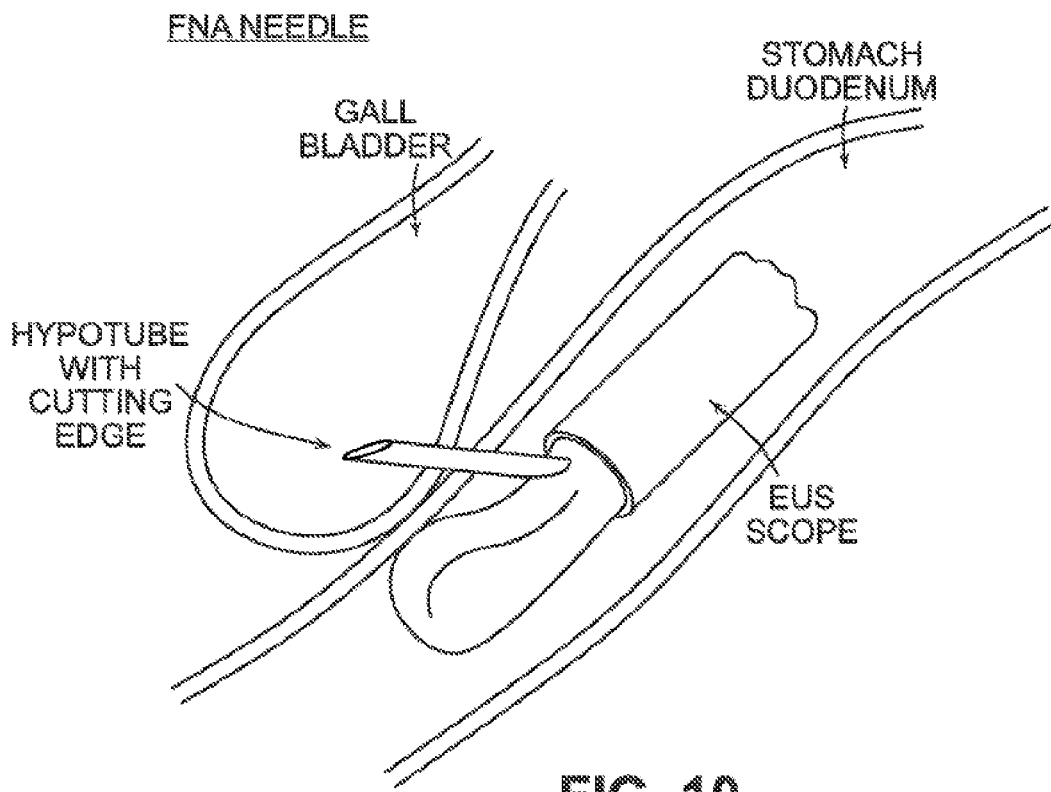
Figure 11:
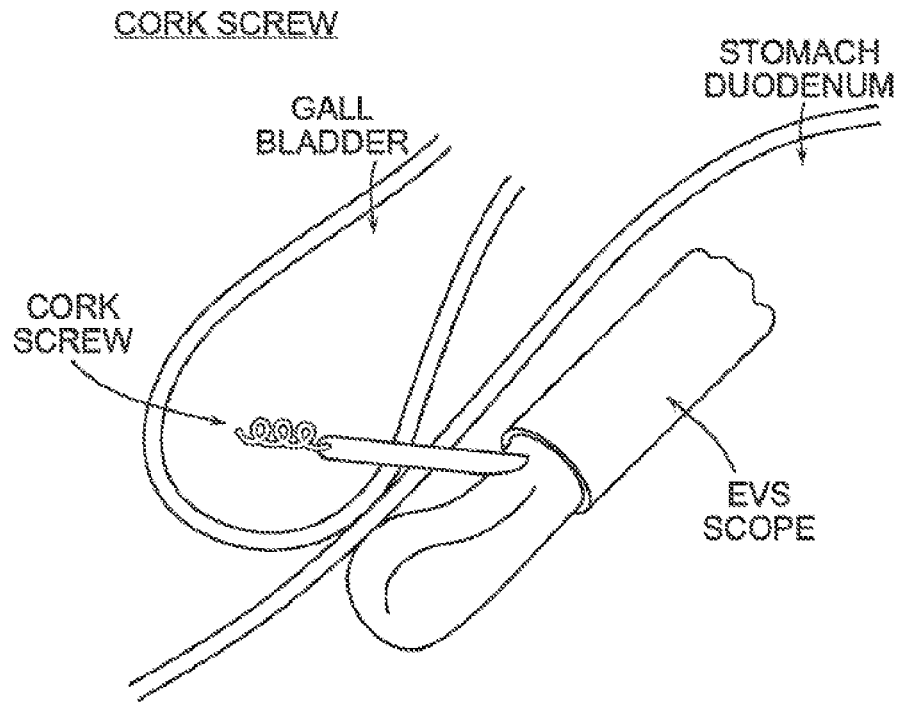
Figure 12:
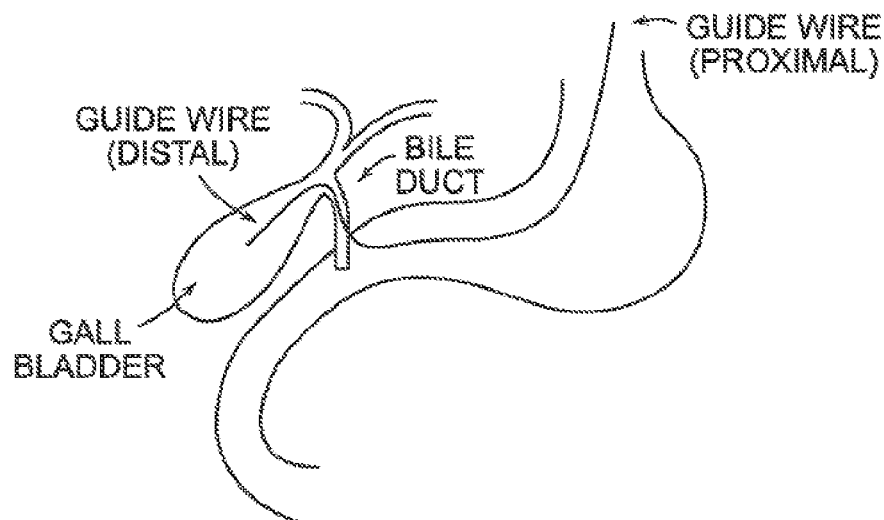

FIGS. 9-12 illustrates various methods of accessing the target site, specifically accessing a gallbladder via an endoscopic ultrasound guided procedure. FIG. 9 illustrates the use of monopolar energy for piercing and accessing the gallbladder. FIG. 10 illustrates the use of a fine aspiration needle (FNA) for piercing and accessing the gallbladder. FIG. 11 illustrates the use of a corkscrew-type needle for piercing and accessing the gallbladder. FIG. 12 illustrates the use of a guidewire passed through the bile duct.

Figure 13:
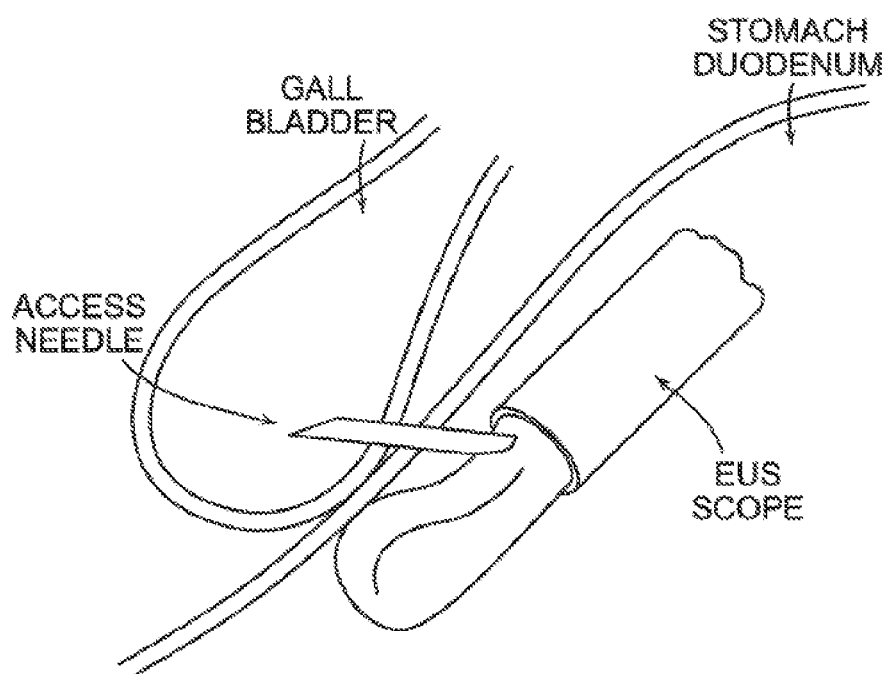
FIG. 13 shows endoscopic ultrasound guided needle piercing of the gallbladder to access the interior of the gallbladder for subsequent delivery of a magnet assembly therein.
Figure 14:
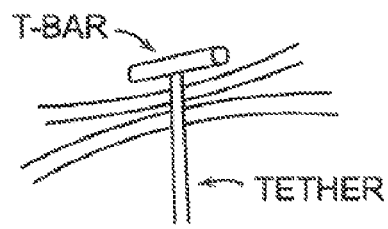
FIGS. 14, 15, 16 and 17 illustrate various devices for anchoring the access device and/or delivery device to the target site at the gallbladder.
Figure 15:
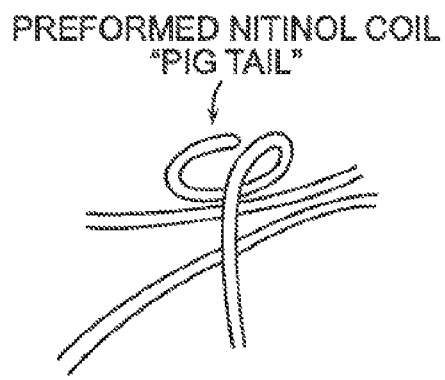
Figure 16:
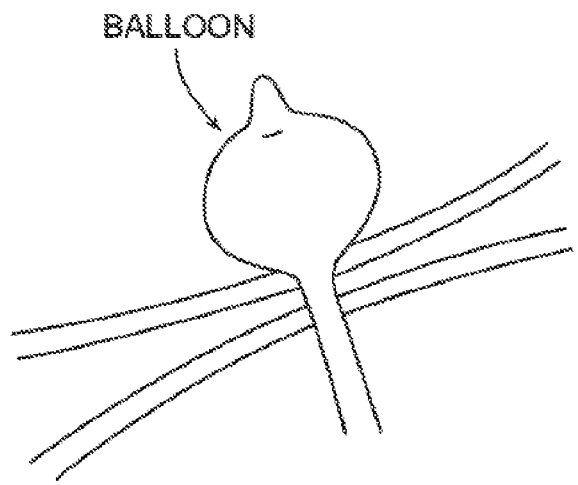
Figure 17:
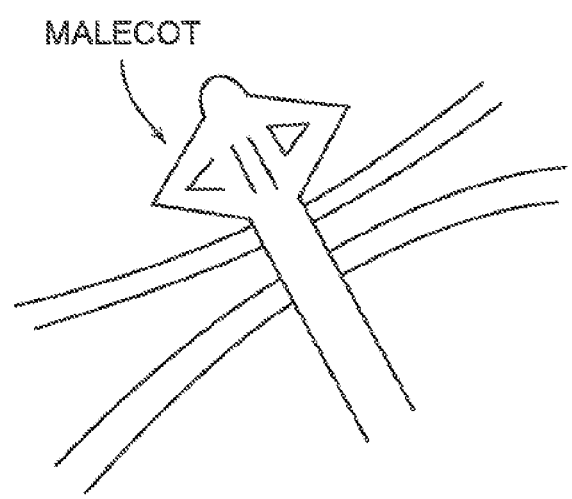
Figure 18A:
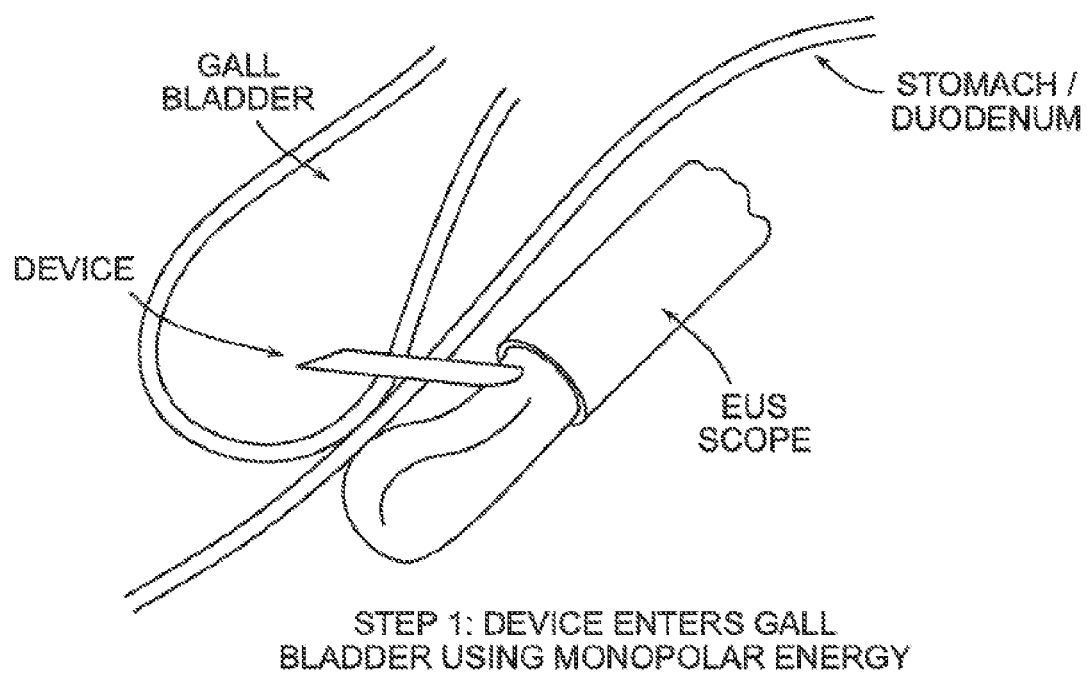
FIGS. 18A, 18B, 18C, 18D, 18E, and 18F illustrate a technique of accessing the gallbladder and delivering a pair of magnetic anastomosis devices for the formation of an anastomosis the gallbladder tissue and adjacent tissue.
Figure 18B:
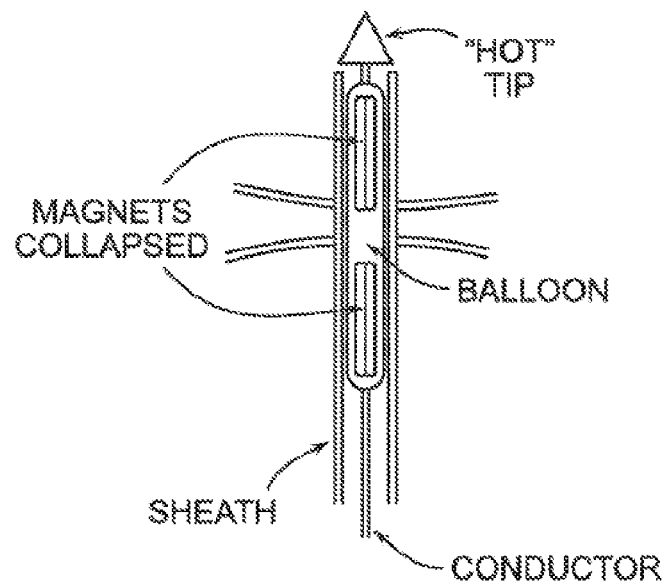
Figure 18C:
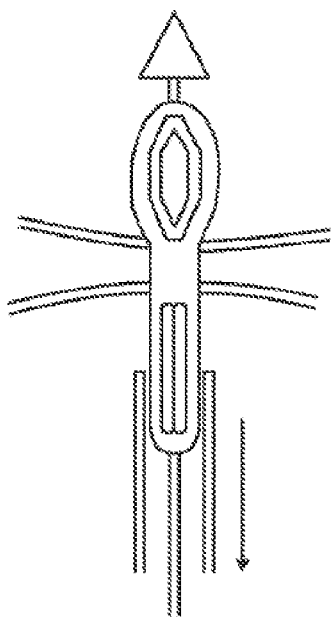
Figure 18D:
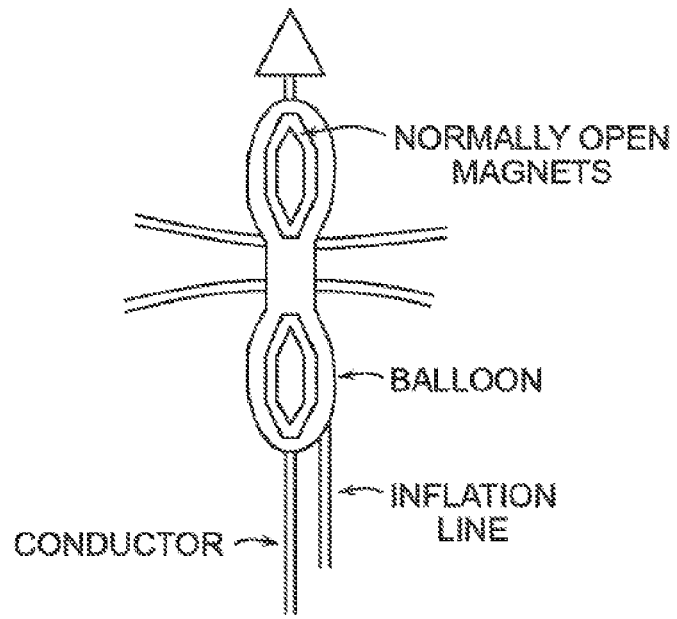
Figure 18E:
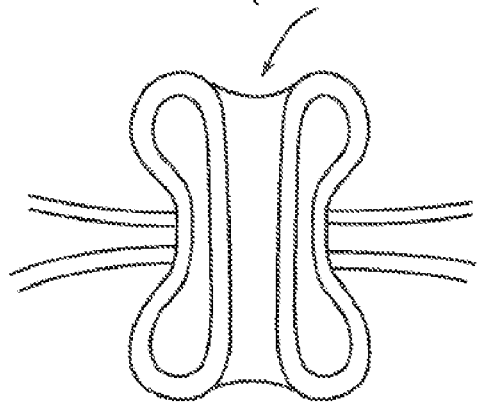
Figure 18F:
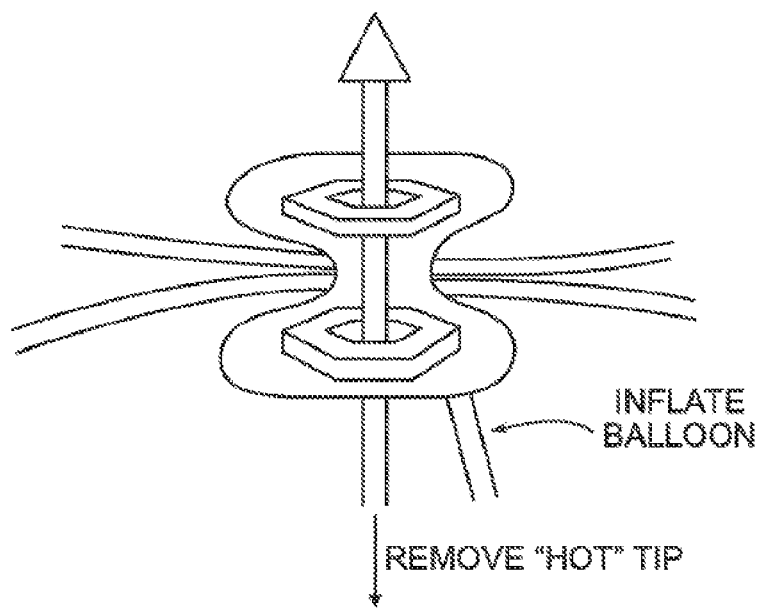

FIG. 13 shows endoscopic ultrasound guided needle piercing of the gallbladder to access the interior of the gallbladder for subsequent delivery of a magnet assembly therein. FIGS. 14, 15, 16 and 17 illustrate various devices for anchoring the access device and/or delivery device to the target site at the gallbladder. FIG. 14 illustrates a T-bar member. FIG. 15 illustrates a nitinol coil (e.g., "pig tail"). FIG. 16 illustrates a balloon member of a catheter. FIG. 17 illustrates a malecot catheter. FIGS. 18A-18F illustrate a method of accessing the gallbladder, via endoscopic ultrasound guided access and utilizing an access device emitting monopolar energy, anchoring a delivery device via the use of a balloon catheter, and subsequently delivering a pair of magnetic anastomosis devices within the balloon while the balloon is anchored within the formed enterotomy between the gallbladder tissue and adjacent tissue (i.e., stomach or duodenum tissue), thereby deploying the devices on either side of the respective tissues (i.e., first device within the gallbladder and second device within stomach or duodenum) for the formation of an anastomosis there between.

Figure 19:
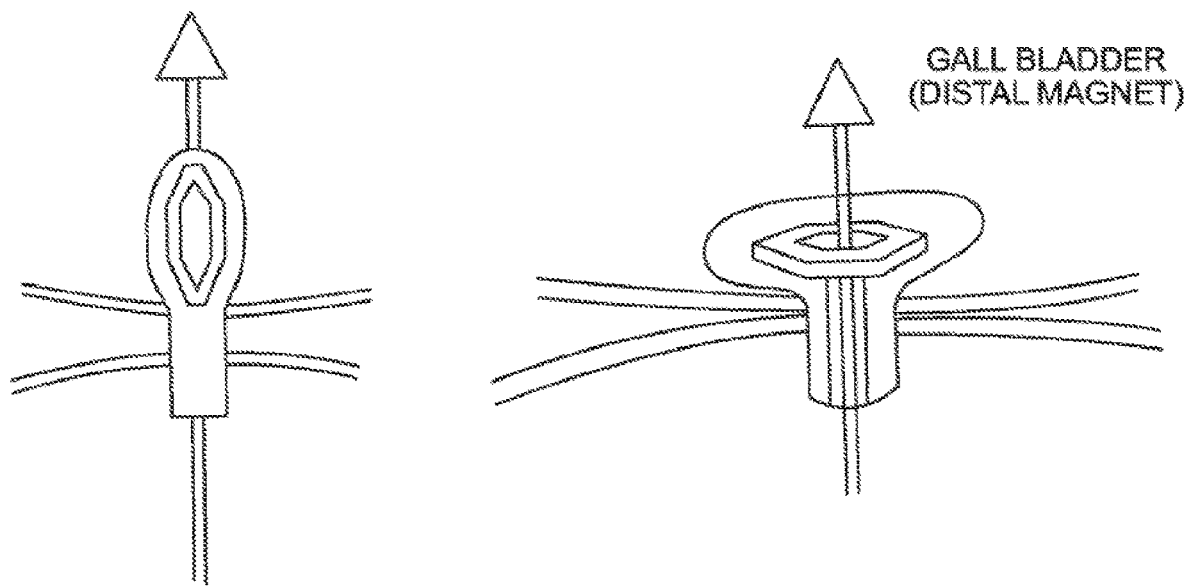
FIG. 19 illustrates a variation of design of FIGS. 18A-18F, specifically utilizing a balloon to deliver a single magnetic anastomosis device within the gallbladder, rather than delivering the pair.
Figure 21E:
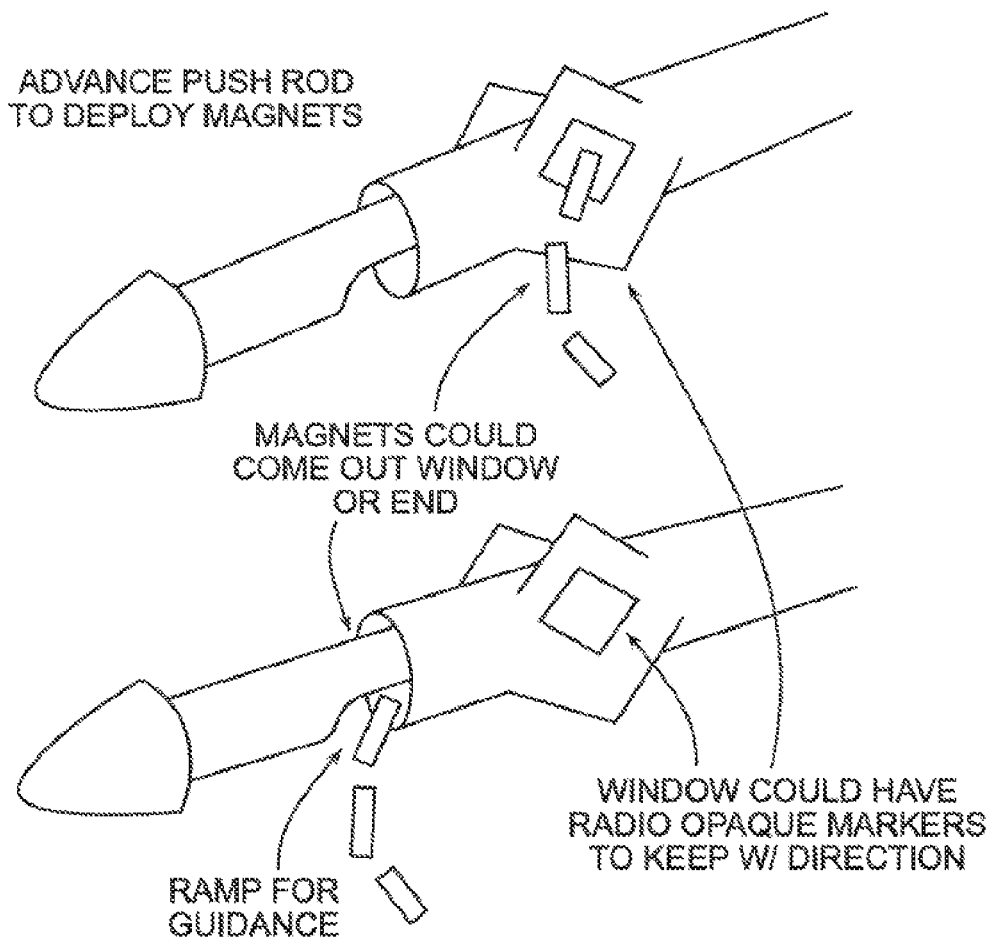

FIG. 19 illustrates a variation of design of FIGS. 18A-18F, specifically utilizing a balloon to deliver a single magnetic anastomosis device within the gallbladder, rather than delivering the pair.

FIGS. 20A-20C illustrate a method of accessing the gallbladder, via endoscopic ultrasound guided access and utilizing a hot insertion tube emitting monopolar energy, and subsequently delivering a magnetic anastomosis device within the gallbladder via the hot tube. As shown in FIG. 20B, a user need only activate monopolar energy to advance the insertion tube into the gallbladder.

FIGS. 21A-21E illustrate a method of accessing the gallbladder, via endoscopic ultrasound guided access and utilizing an access device having a conductor including a "hot" tip emitting monopolar energy, anchoring the delivery device via the use of a malecot catheter, and subsequently utilizing the malecot catheter as a conduit for delivering a magnetic anastomosis device therethrough and into the gallbladder while the malecot catheter is anchored within the formed enterotomy between the gallbladder tissue and adjacent tissue (i.e., stomach or duodenum tissue).

Figure 22C:
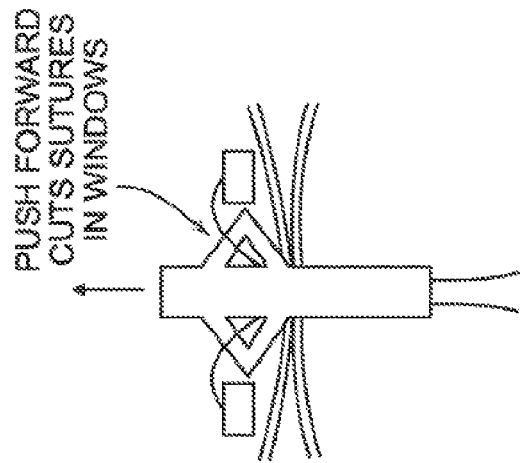
FIGS. 22A, 22B, and 22C illustrate a variation of the procedure and devices illustrated in FIGS. 21A-21E in that the magnetic anastomosis device is preloaded into a distal end of the malecot catheter of the delivery device resulting in delivery and deployment of the device upon transitioning of the malecot end into an anchored position.
Figure 22B:
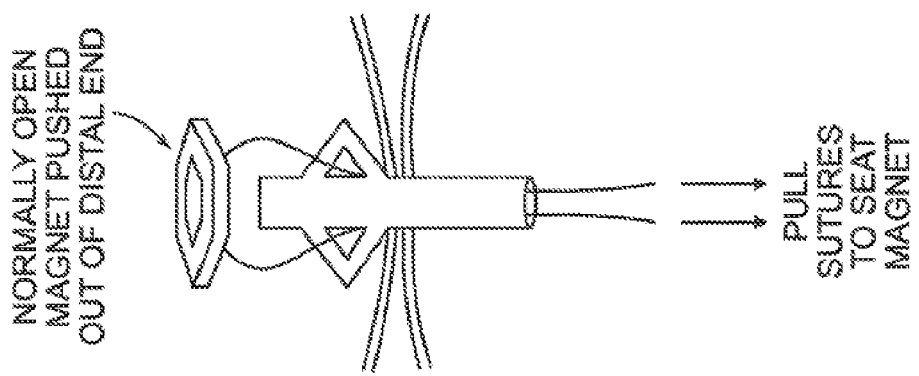
Figure 22A:
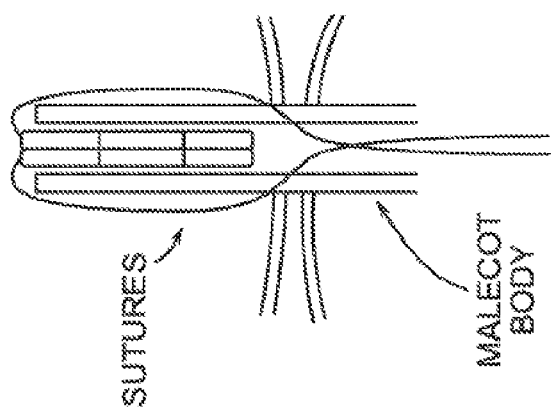

FIGS. 22A-22C illustrate a variation of the procedure and devices illustrated in FIGS. 21A-21E in that the magnetic anastomosis device is preloaded into a distal end of the malecot catheter of the delivery device resulting in delivery and deployment of the device upon transitioning of the malecot end into an anchored position.

Figure 23:
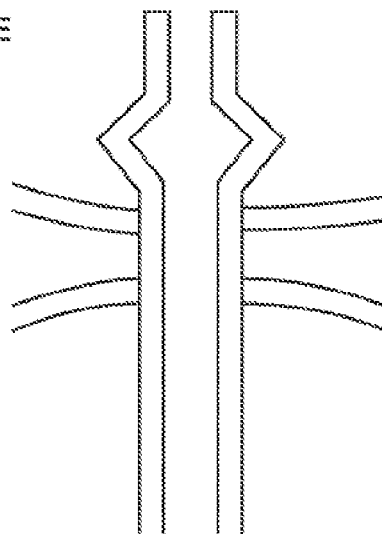
FIG. 23 illustrates a malecot catheter having a distal end that expands into the anchored position on one side of the gallbladder tissue wall.
Figure 24:
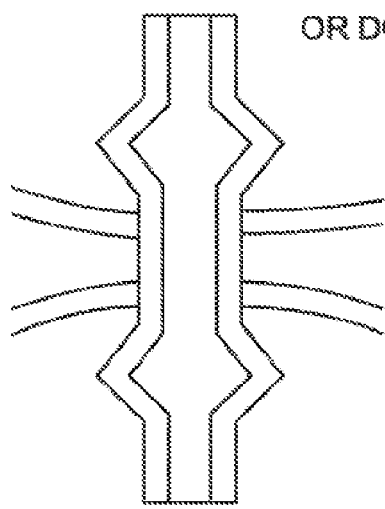
FIG. 24 illustrates a malecot catheter having a distal end that expands into the anchored position on both sides of the gallbladder tissue wall.

FIG. 23 illustrates a malecot catheter having a distal end that expands into the anchored position on one side of the gallbladder tissue wall. FIG. 24 illustrates a malecot catheter having a distal end that expands into the anchored position on both sides of the gallbladder tissue wall. In both instances, a temporary malecot may be placed inside of the gallbladder to create a temporary conduit, which allows for drainage to occur immediately and could further allow for insufflation of the gallbladder as well. It should be noted that, any of the embodiments that provide access from the GI tract into the gallbladder (malecot, hot tube, nitinol coil, balloon, etc.), specifically any of the devices that creates a channel through which the magnetic anastomosis device will pass, can also serve as a drainage channel. More specifically, after the access channel has been created, any fluid of material within the gallbladder could be evacuated (either on its own or if suction is applied) before delivery of the magnetic anastomosis device begins. The channel could also be used to push fluid into the gallbladder prior to draining out the gallbladder (potentially doing the fill/drain cycle a number of times) in order to 'clean' out the gallbladder in the event that the gallbladder has excess fluid and contents within (i.e., bile or other contents).

Figure 25E:
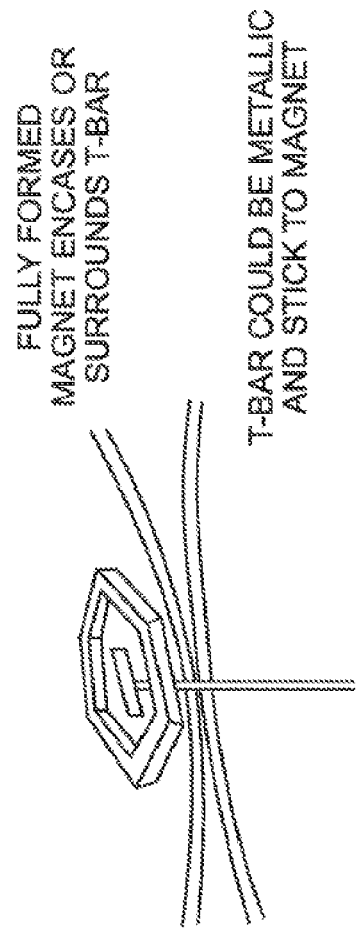
Figure 25D:
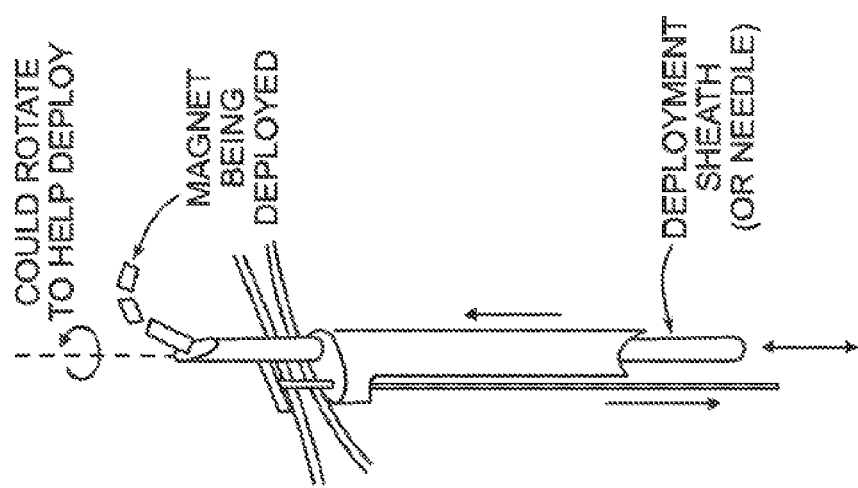

FIGS. 25A-25E illustrate a method of accessing the gallbladder, via endoscopic ultrasound guided access needle access, anchoring the delivery device via the use of a T-bar assembly and stabilizer member, and subsequently delivering a magnetic anastomosis device therethrough, via a deployment sheath, and into the gallbladder while the T-bar is anchored within the formed enterotomy between the gallbladder tissue and adjacent tissue (i.e., stomach or duodenum tissue). As shown in FIG. 25A, the T-bar is tethered to the gallbladder wall. The stabilizer member is then advanced to the wall of the duodenum or stomach for traction, as shown in FIG. 25B. The deployment sheath is then advanced into the gall bladder, at which point the magnetic anastomosis device can be delivered, as illustrated in FIG. 25C.

Figure 26C:
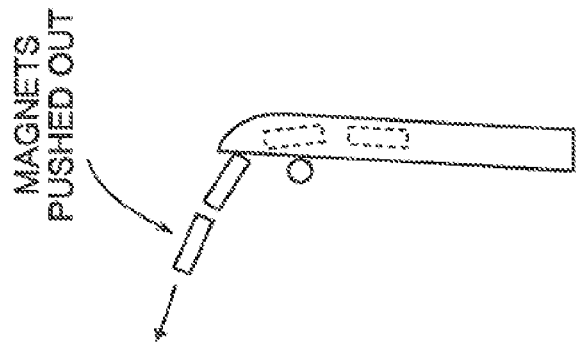
FIGS. 26A, 26B, 26C illustrate a variation of the procedure and devices illustrated in FIGS. 25A-25E in that the deployment sheath includes a notch on a distal end thereof configured to engage the T-bar upon advancement through the enterotomy, thereby pushing the T-bar to the side to allow for subsequent delivery and deployment of the magnetic anastomosis device.
Figure 26B:
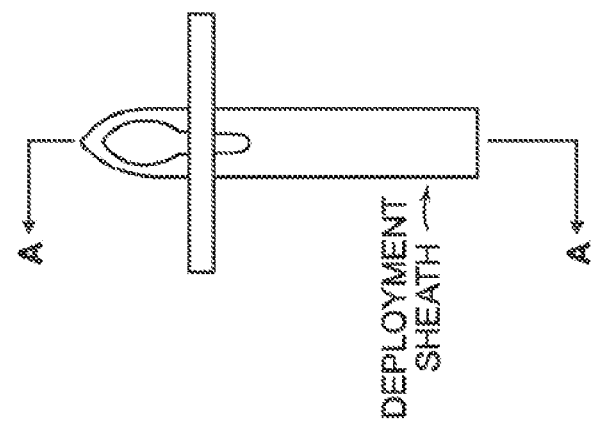
Figure 26A:
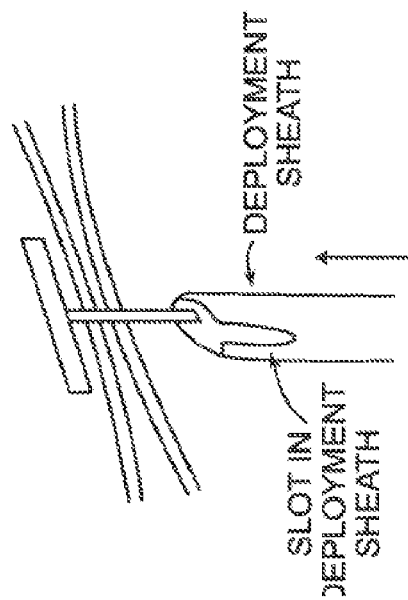

FIGS. 26A-26C illustrate a variation of the procedure and devices illustrated in FIGS. 25A-25E in that the deployment sheath includes a notch on a distal end thereof configured to engage the T-bar upon advancement through the enterotomy, thereby pushing the T-bar to the side to allow for subsequent delivery and deployment of the magnetic anastomosis device.

Figure 27C:
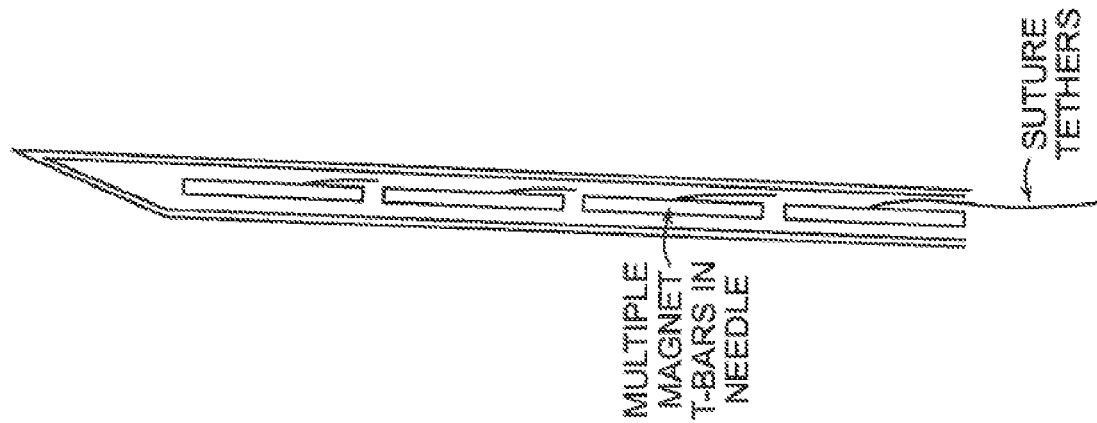
FIGS. 27A, 27B, and 27C illustrate another variation of the procedure and devices illustrated in FIGS. 25A-25E in that, rather than including a deployment sheath for delivering a self-assembling magnetic anastomosis device, as previously described herein, the assembly of FIGS. 27A-27C relies on the depositing of T-bars through an access needle, such that a grouping of T-bars are configured to self-assembly into an array and serve as the distal anastomosis device to correspondingly mate with a proximal magnetic anastomosis device positioned on the other side to subsequently compress tissue there between to form an anastomosis.
Figure 27B:
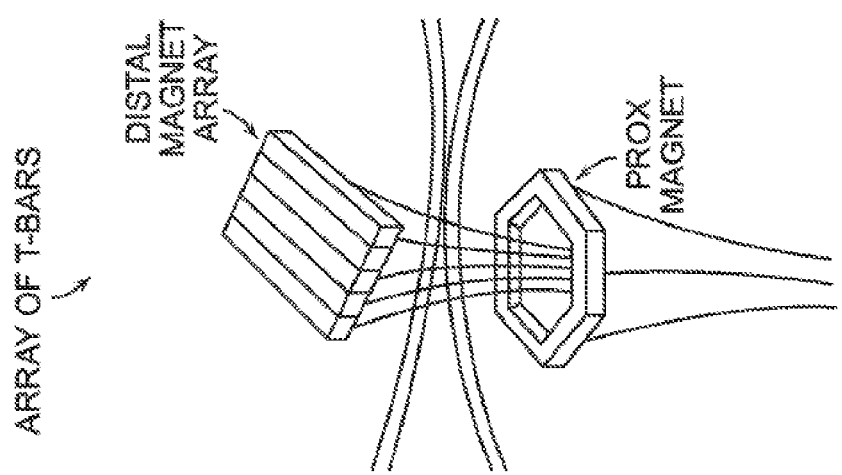
Figure 27A:
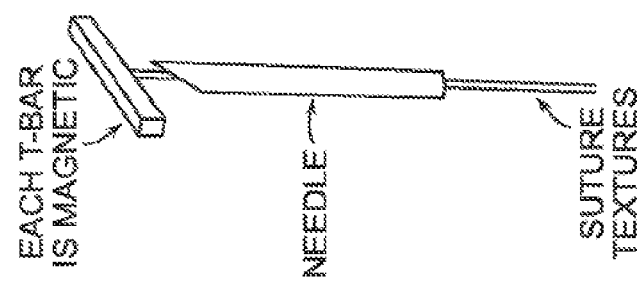

FIGS. 27A-27C illustrate another variation of the procedure and devices illustrated in FIGS. 25A-25E in that, rather than including a deployment sheath for delivering a self-assembling magnetic anastomosis device, as previously described herein, the assembly of FIGS. 27A-27C relies on the depositing of T-bars through an access needle, such that a grouping of T-bars are configured to self-assembly into an array and serve as the distal anastomosis device to correspondingly mate with a proximal magnetic anastomosis device positioned on the other side to subsequently compress tissue there between to form an anastomosis.

Figure 28A:
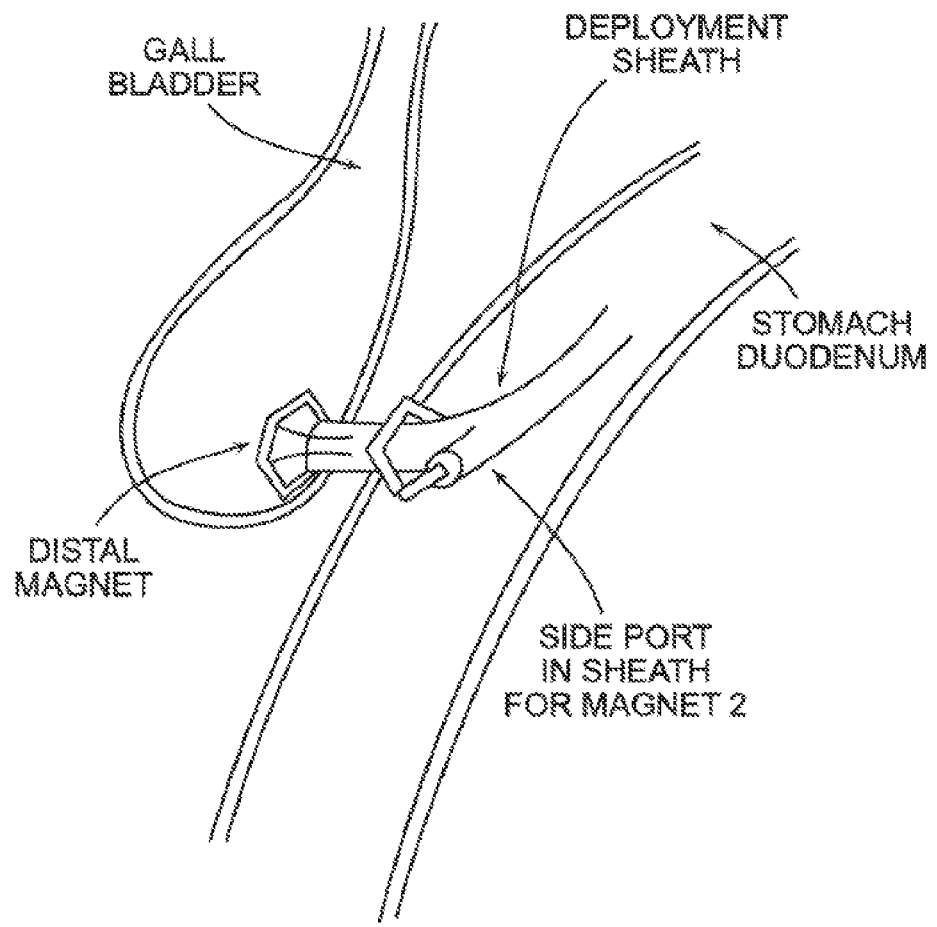
FIGS. 28A, 28B, and 28C illustrate a method of accessing the gallbladder, via endoscopic ultrasound guided access needle access, utilizing a side port deployment sheath for delivery and deployment of a pair of magnetic anastomosis devices.
Figure 28B:
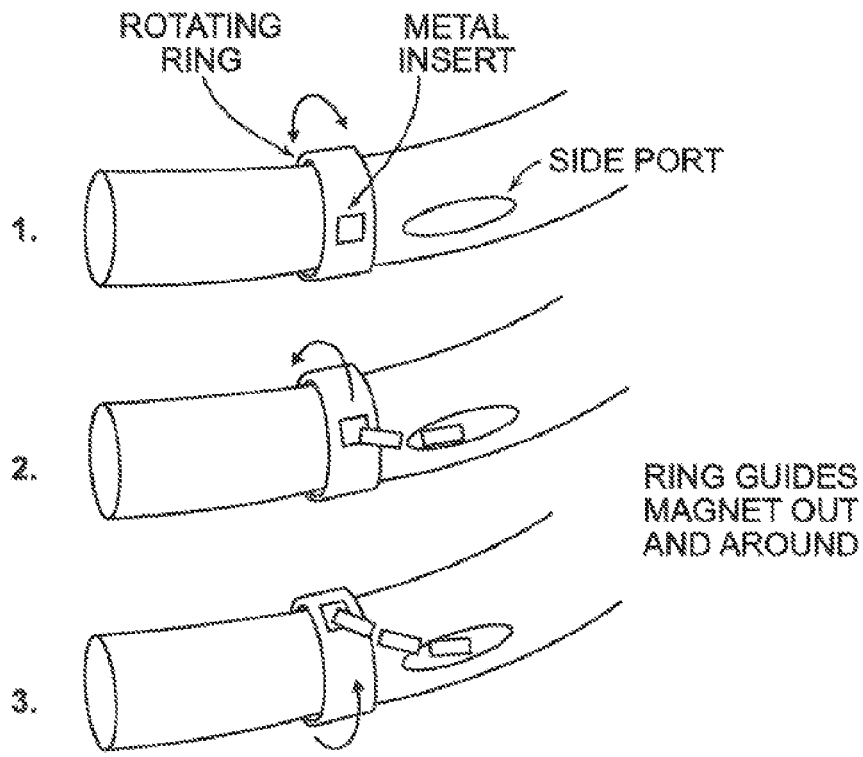
Figure 28C:
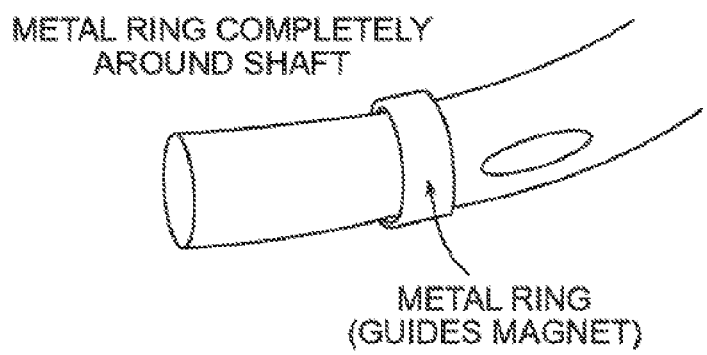

FIGS. 28A-28C illustrate a method of accessing the gallbladder, via endoscopic ultrasound guided access needle access, utilizing a side port deployment sheath for delivery and deployment of a pair of magnetic anastomosis devices.

Figure 29A:
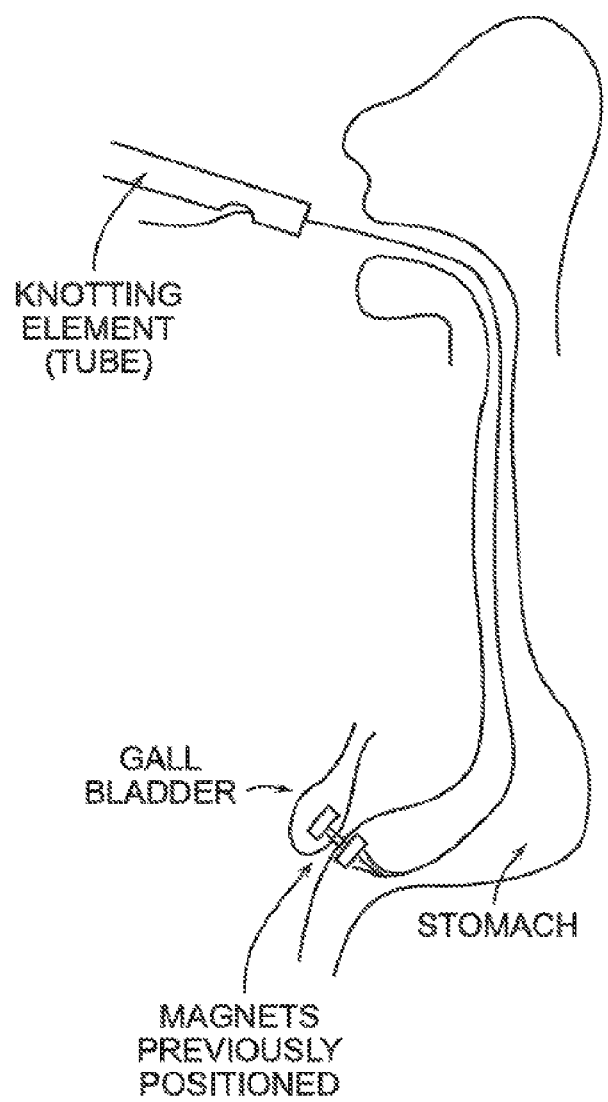
FIGS. 29A, 29B, and 29C illustrate a knotting member configured to secure already deployed and positioned magnetic anastomosis devices to the target site tissues and subsequently cut guide elements or sutures coupled thereto.
Figure 29B:
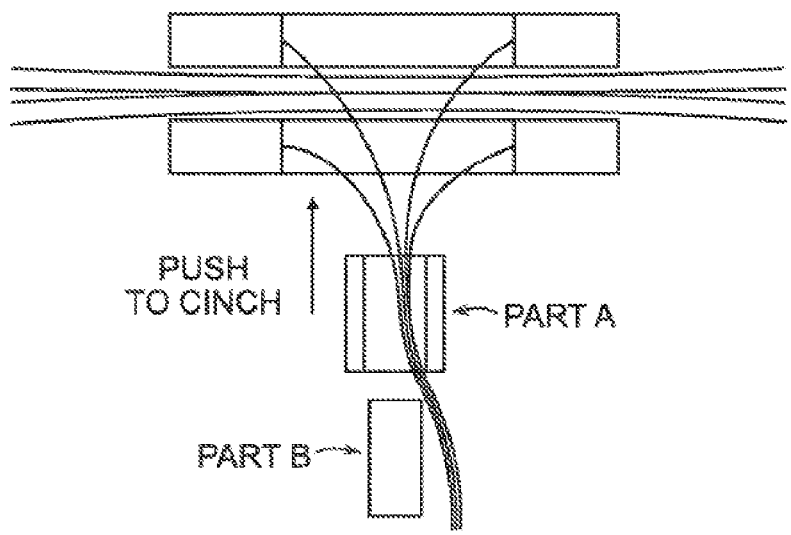
Figure 29C:
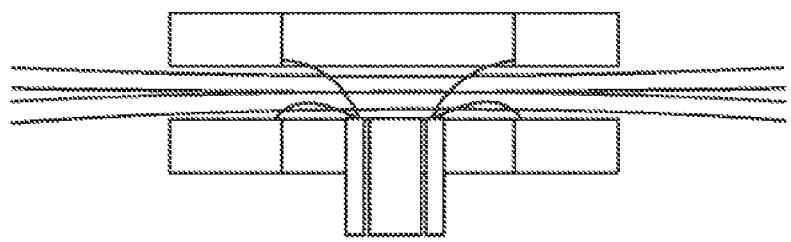
Figure 30A:
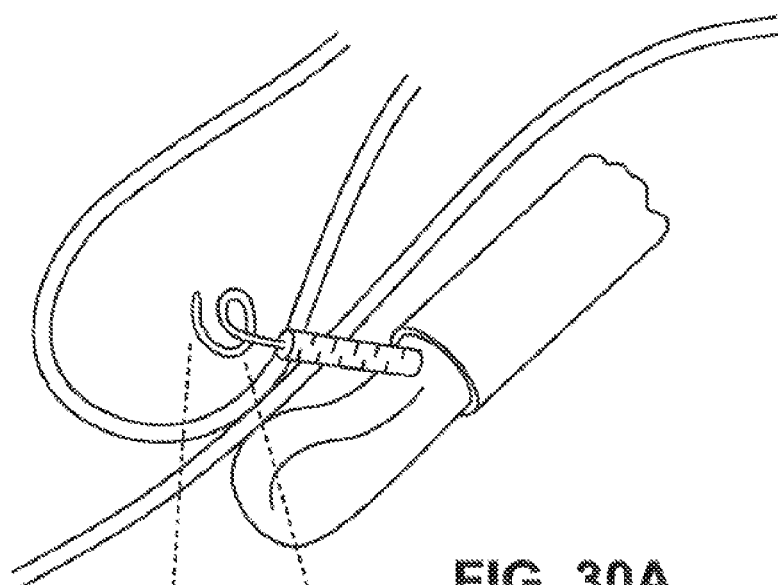
FIGS. 30A, 30B, 30C, and 30D illustrate a technique of accessing the gallbladder and delivering a pair of magnetic anastomosis devices for the formation of an anastomosis the gallbladder tissue and adjacent tissue.
Figure 30B:
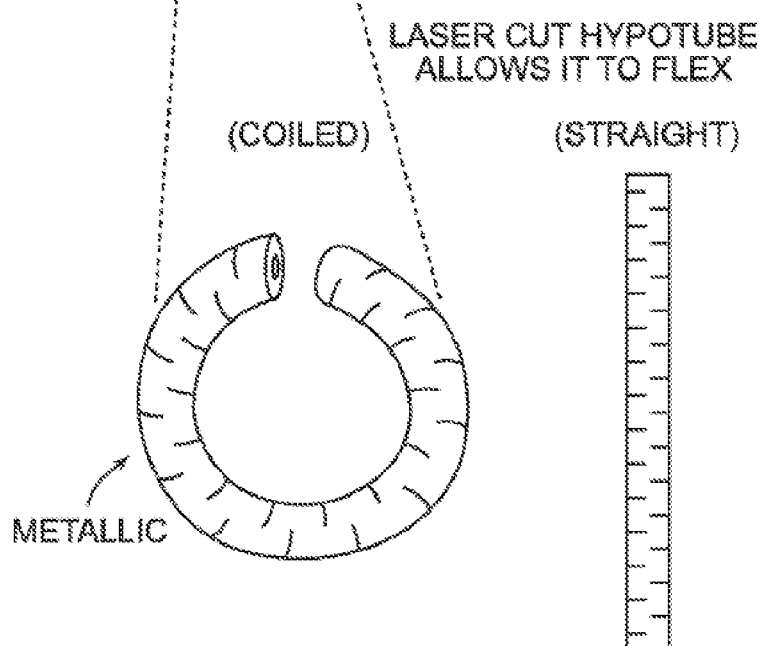
Figure 30C:
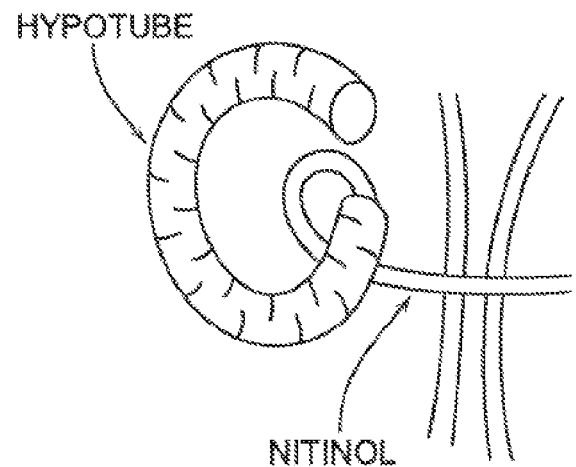
Figure 30D:
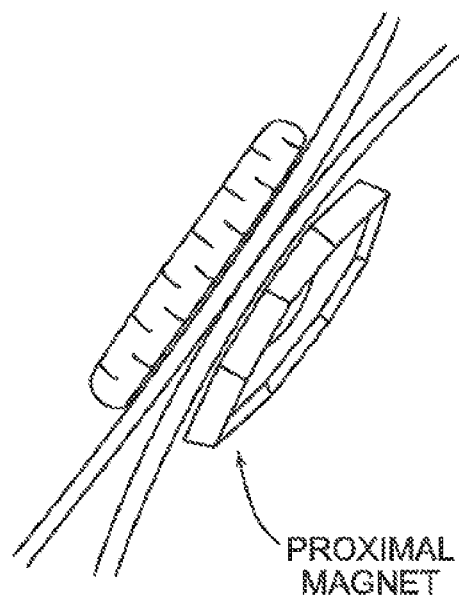

FIGS. 29A-29C illustrate a knotting member configured to secure already deployed and positioned magnetic anastomosis devices to the target site tissues and subsequently cut guide elements or sutures coupled thereto. As shown in FIG. 29A, the knotting member is advanced over guide elements within a working channel of a scope. As shown in FIG. 29B, the knotting member advances towards the magnetic anastomosis devices, wherein the knotting member generally consists of an outer tube member and an inner rod member, such that, upon reaching the devices, the inner rod member can be pressed towards a distal end of the outer tube member, thereby securing a portion of the guide elements there between and further cutting the guide elements in the process.

FIGS. 30A-30D illustrate a method of accessing the gallbladder, via endoscopic ultrasound guided access needle access, and delivering a magnetic coil or ring configured to transition from a substantially linear shape to a substantially annular shape upon delivery into the gallbladder and is configured to serve the distal anastomosis device to correspondingly mate with a proximal magnetic anastomosis device positioned on the other side to subsequently compress tissue there between to form an anastomosis.

Figure 31A:
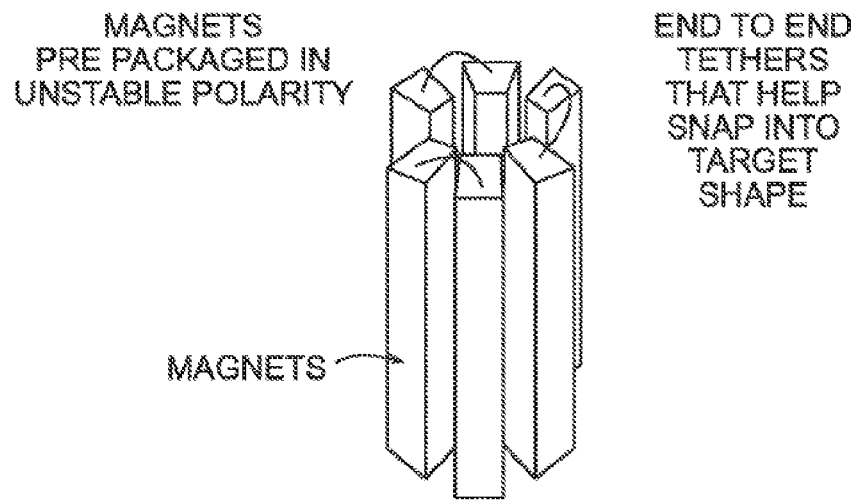
FIGS. 31A and 31B illustrate a set of magnetic segments prepackaged in an unstable polarity including a plurality of guide elements, tethers, or sutures coupling adjacent segments to one another to assist in self-assembly of the magnetic segments into a polygon deployed shape.
Figure 31B:
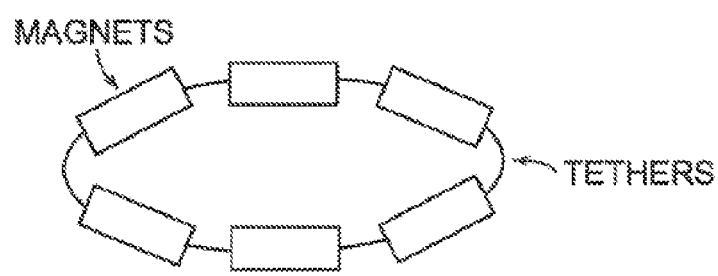
Figure 32A:
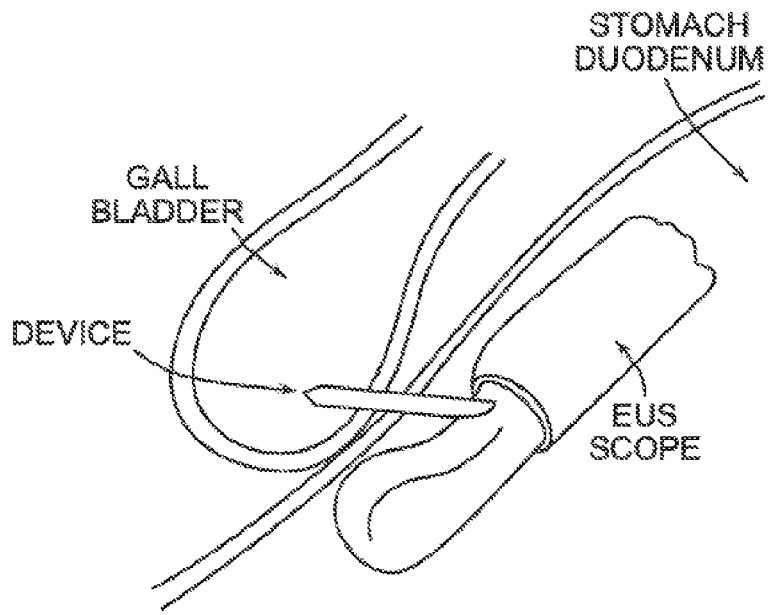
FIGS. 32A and 32B illustrate a method of accessing the gallbladder, via endoscopic ultrasound guided access and utilizing an access device having a conductor including a "hot" tip emitting monopolar energy, and subsequently delivering the prepackaged magnetic segments of FIGS. 31A and 31B into the gallbladder by way of a sheath.
Figure 32B:
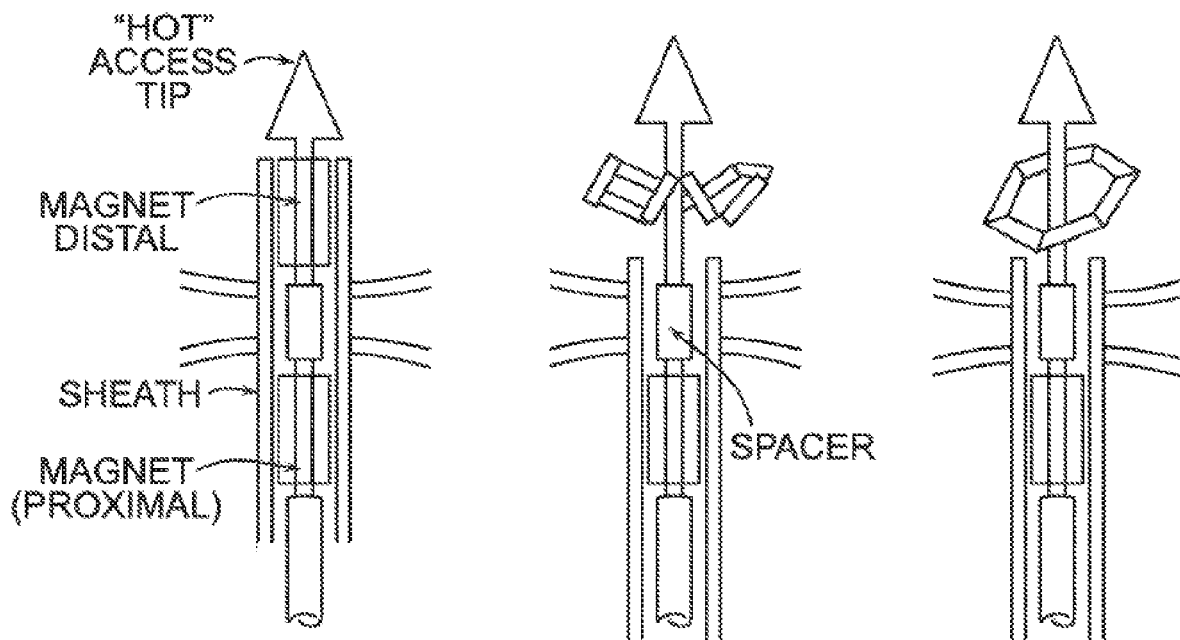

FIGS. 31A and 31B illustrate a set of magnetic segments prepackaged in an unstable polarity including a plurality of guide elements, tethers, or sutures coupling adjacent segments to one another to assist in self-assembly of the magnetic segments into a polygon deployed shape. FIGS. 32A and 32B illustrate a method of accessing the gallbladder, via endoscopic ultrasound guided access and utilizing an access device having a conductor including a "hot" tip emitting monopolar energy, and subsequently delivering the prepackaged magnetic segments of FIGS. 31A-31B into the gallbladder by way of a sheath.

Figure 33A:
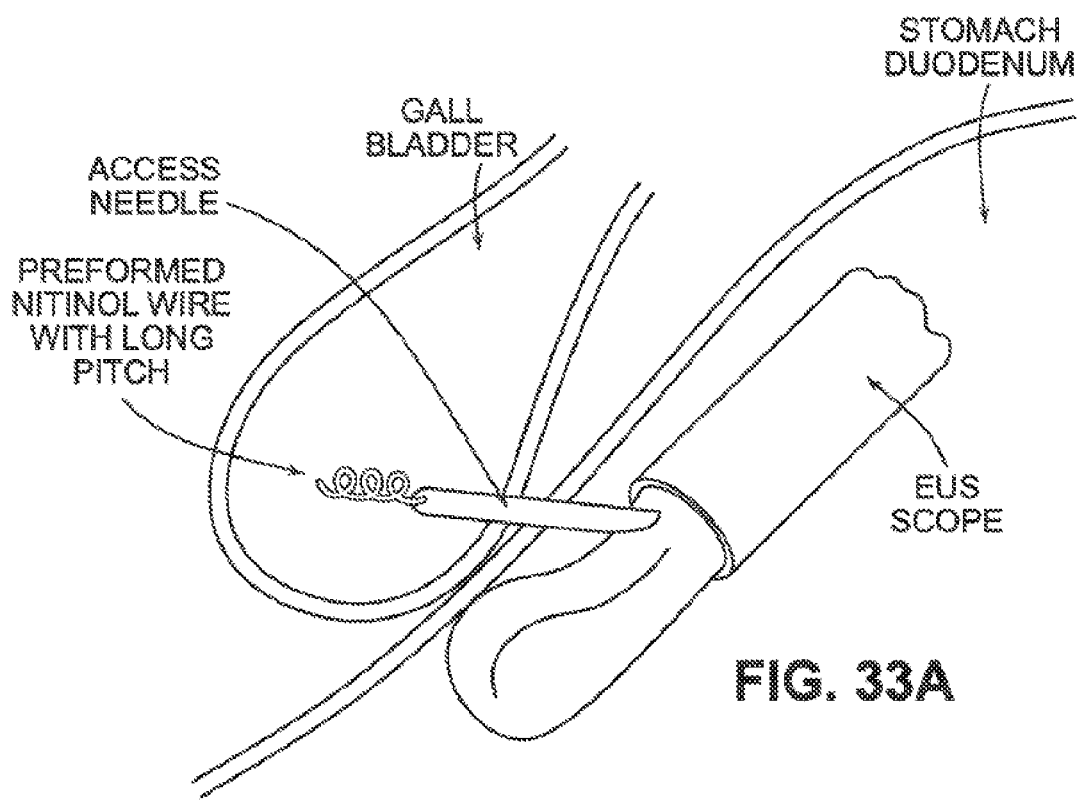
FIGS. 33A, 33B, and 33C illustrate a method of accessing the gallbladder, via endoscopic ultrasound guided access and utilizing a needle for access into the gallbladder, and subsequent delivery of a coiled stack of magnetic segments configured to serve the distal anastomosis device to correspondingly mate with a proximal magnetic anastomosis device positioned on the other side to subsequently compress tissue there between to form an anastomosis.
Figure 33B:
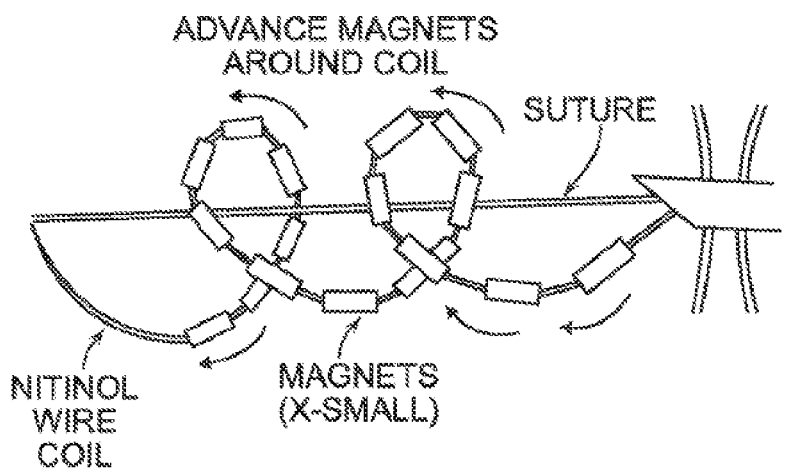
Figure 33C:
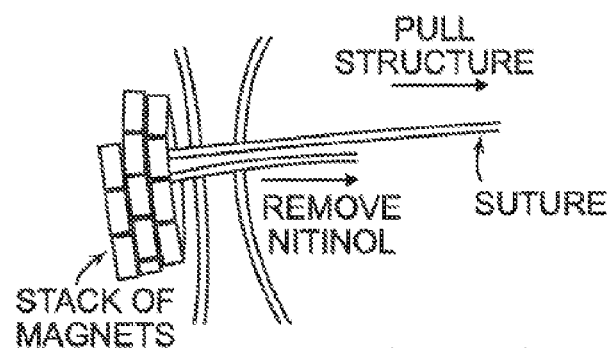

FIGS. 33A-33C illustrate a method of accessing the gallbladder, via endoscopic ultrasound guided access and utilizing a needle for access into the gallbladder, and subsequent delivery of a coiled stack of magnetic segments configured to serve the distal anastomosis device to correspondingly mate with a proximal magnetic anastomosis device positioned on the other side to subsequently compress tissue there between to form an anastomosis. As shown in FIG. 33A, the nitinol coil is advanced into the gallbladder. The magnetic segments are then advances around the extended nitinol coil, as shown in FIG. 33B. Upon pulling a suture, as shown in FIG. 33C, the magnetic segments collapse upon one another (due to magnetic attraction forces) and form a coiled stack of magnets upon removal of the nitinol coil.

Figure 34A:
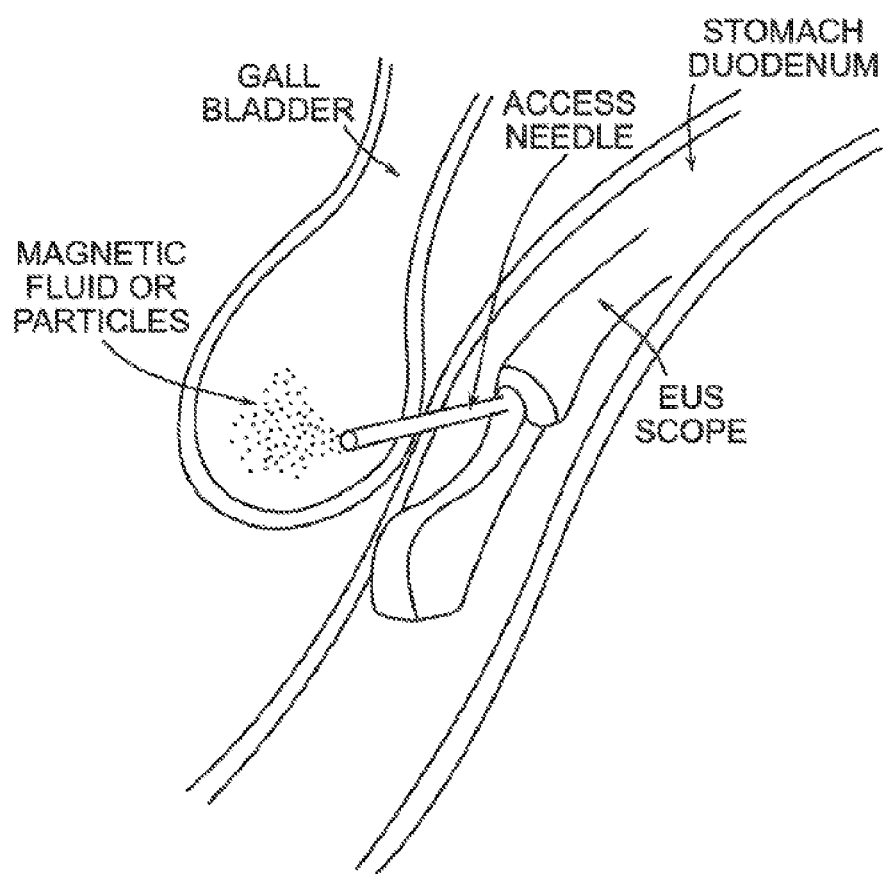
FIGS. 34A and 34B illustrate a technique of accessing the gallbladder and delivering a pair of magnetic anastomosis devices for the formation of an anastomosis the gallbladder tissue and adjacent tissue.
Figure 34B:
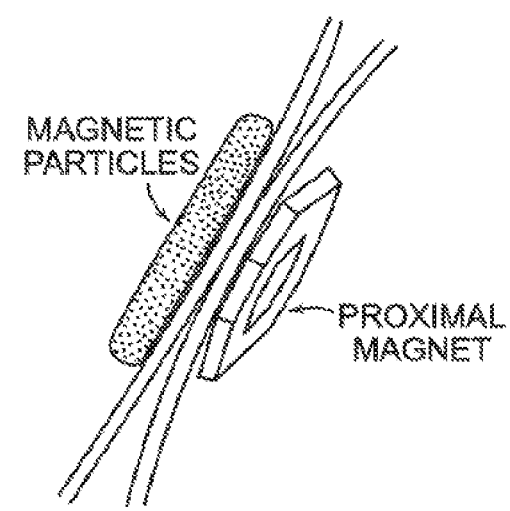

FIGS. 34A-34B illustrate a method of accessing the gallbladder, via endoscopic ultrasound guided access and utilizing a needle for access into the gallbladder, and subsequent delivery of a magnetic fluid or suspension of magnetic particles into the gallbladder configured to serve as the distal anastomosis device to correspondingly mate with a proximal magnetic anastomosis device positioned on the other side to subsequently compress tissue there between to form an anastomosis.

Figure 35:
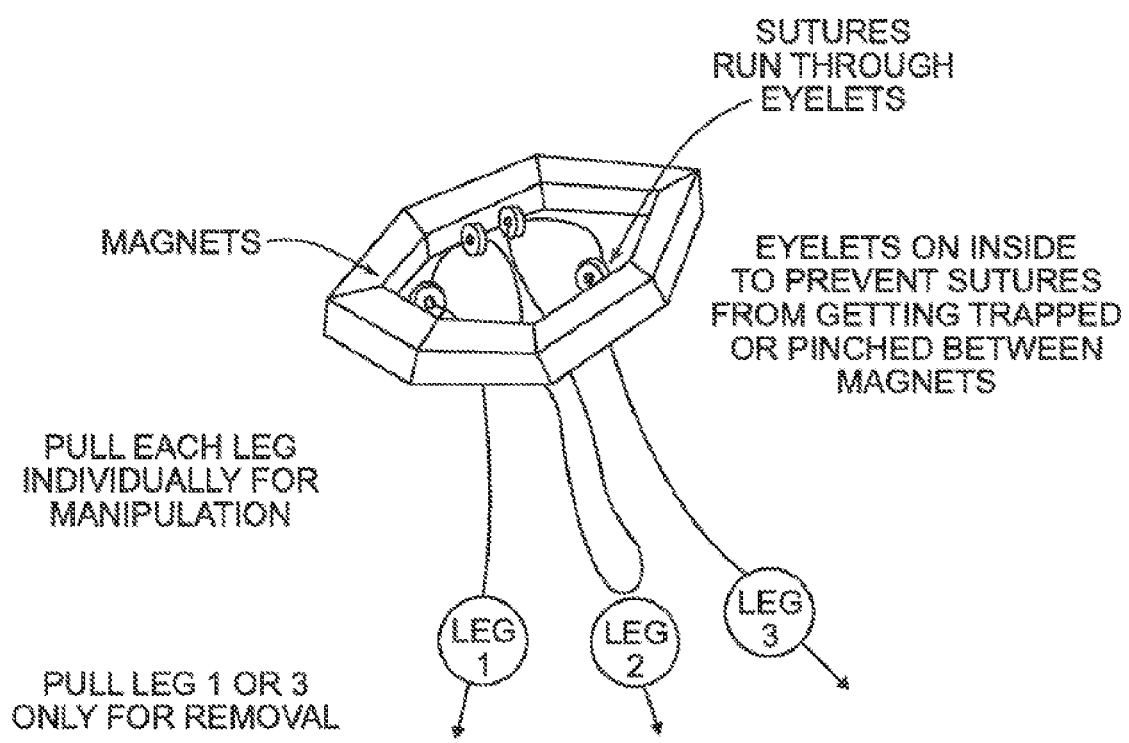
FIG. 35 illustrates a magnetic anastomosis device comprising a continuous guide element or suture that is coupled to a plurality of the magnetic segments of the device by way of eyelets positioned on each of the plurality of magnetic segments.

FIG. 35 illustrates a magnetic anastomosis device comprising a continuous guide element or suture that is coupled to a plurality of the magnetic segments of the device by way of eyelets positioned on each of the plurality of magnetic segments.

Figure 36:
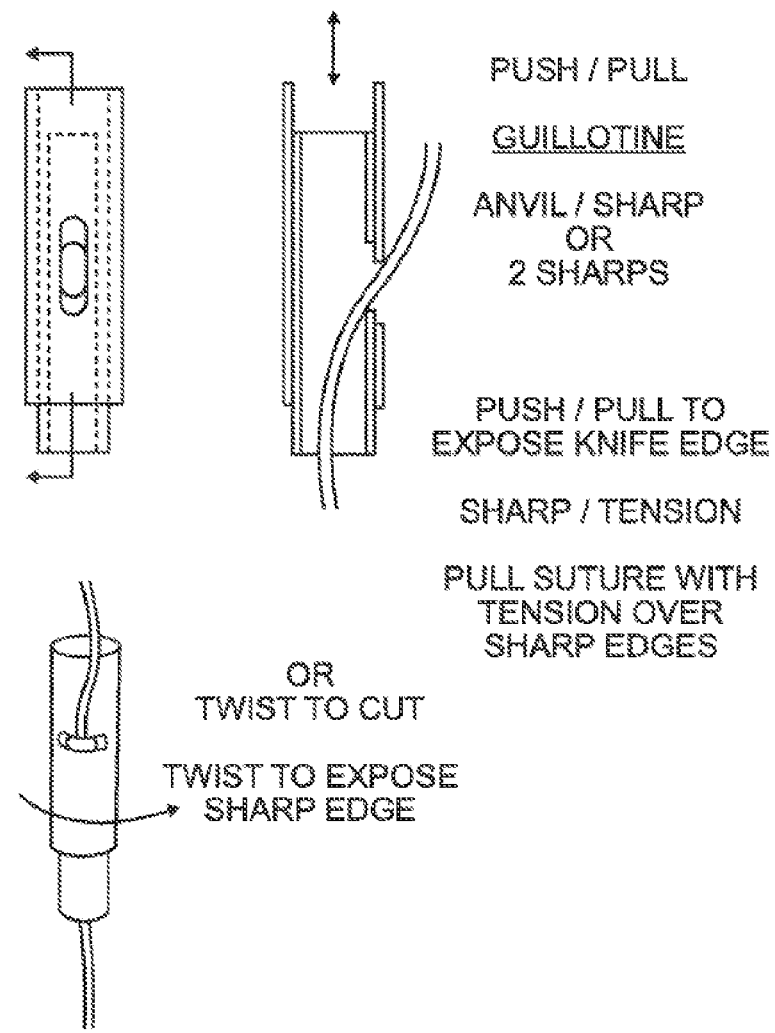
FIG. 36 illustrates one embodiment of a suture cutting arrangement within a deployment sheath of the delivery device, or a secondary device, for cutting the sutures coupled to the magnetic anastomosis devices.

FIG. 36 illustrates one embodiment of a suture cutting arrangement within a deployment sheath of the delivery device, or a secondary device, for cutting the sutures coupled to the magnetic anastomosis devices.

Figure 37A:
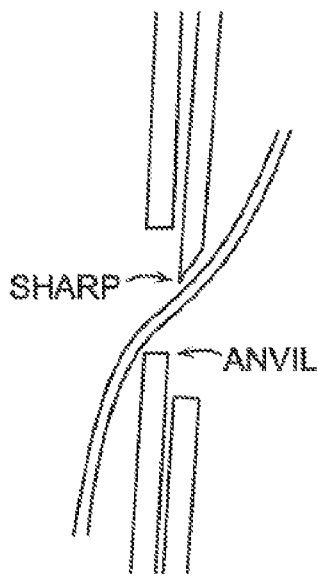
FIGS. 37A and 37B are enlarged side views illustrating an anvil/sharp arrangement and a sharp/sharp arrangement for cutting sutures.
Figure 37B:
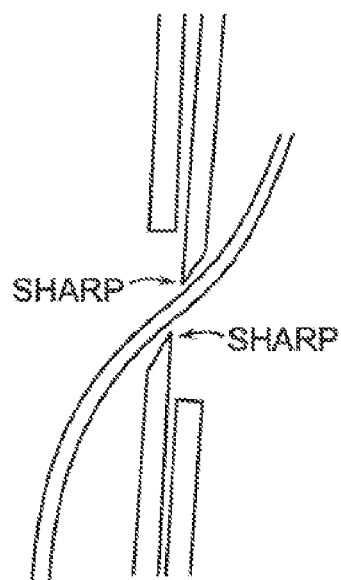
Figure 38:
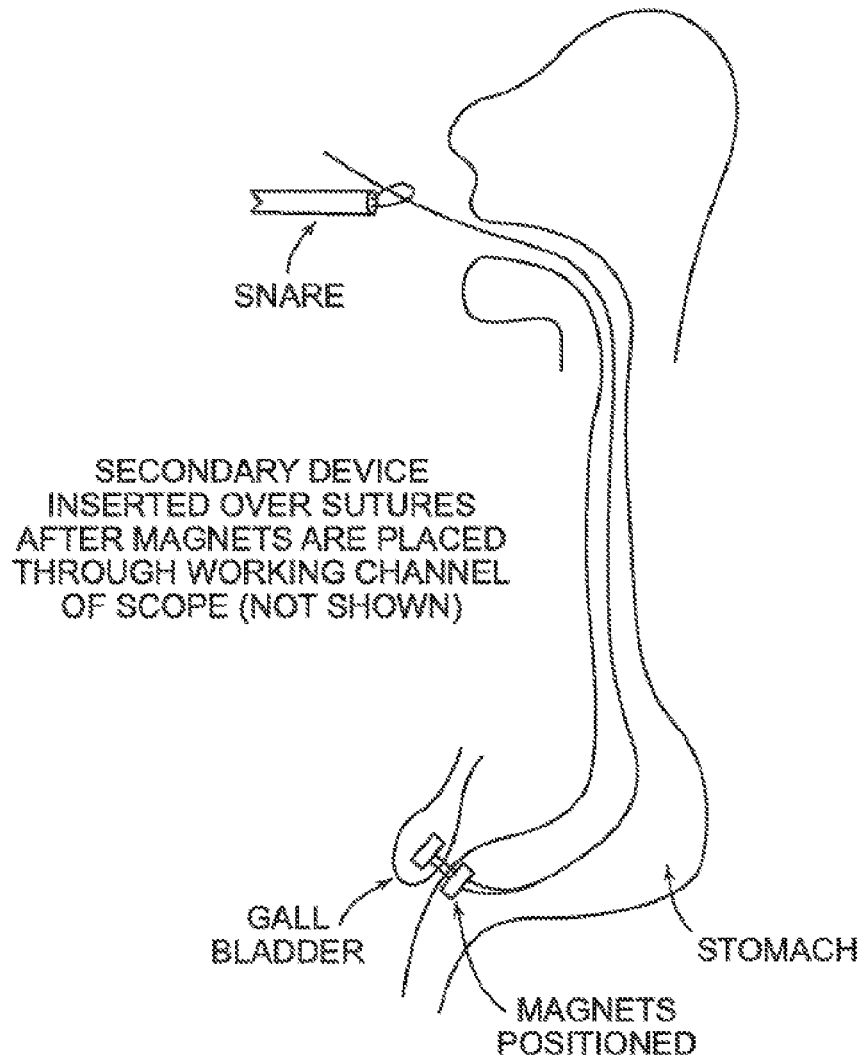
FIG. 38 illustrates a snare device (secondary device) configured to be inserted over the guide elements or sutures coupled to the magnetic anastomosis devices and configured to cut said sutures or guide elements once they have been deployed and positioned at a target site.

FIGS. 37A and 37B are enlarged side views illustrating an anvil/sharp arrangement and a sharp/sharp arrangement for cutting sutures. FIG. 38 illustrates a snare device (secondary device) configured to be inserted over the guide elements or sutures coupled to the magnetic anastomosis devices and configured to cut said sutures or guide elements once they have been deployed and positioned at a target site.

Figure 39A:
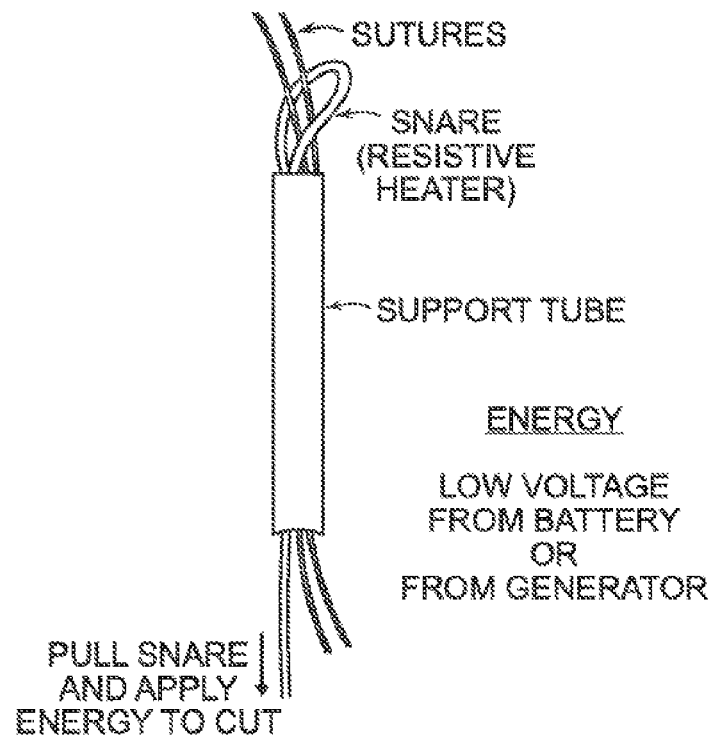
FIG. 39A illustrates a snare device comprising a resistive heating element for cutting guide elements.
Figure 39B:
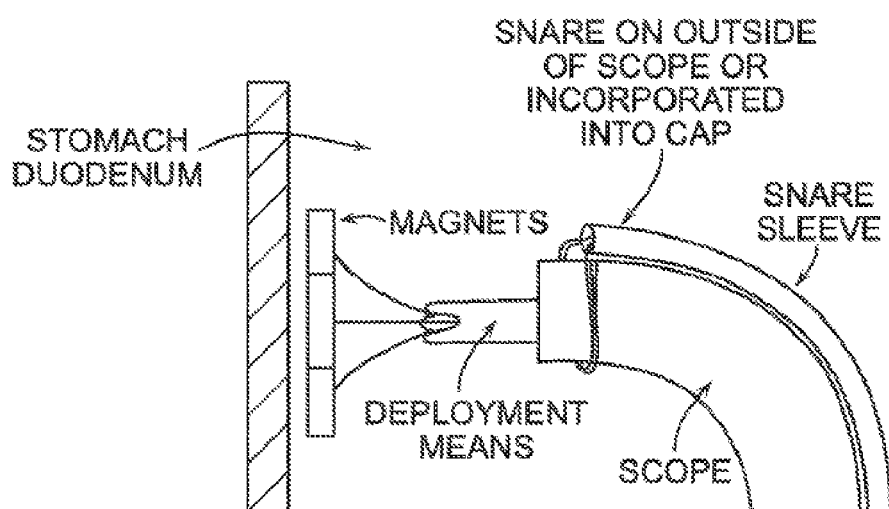
FIGS. 39B and 39C illustrate a snare device comprising a ring member having a cutting edge for cutting guide elements.
Figure 39C:
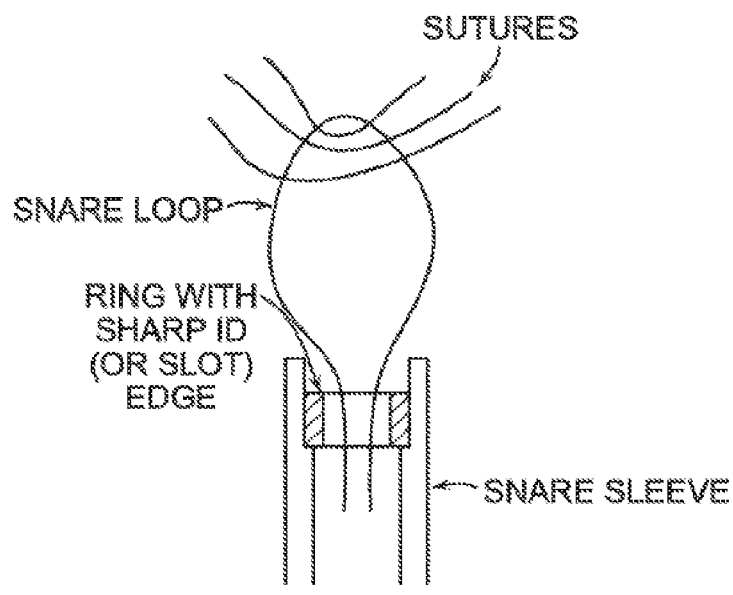
Figure 39D:
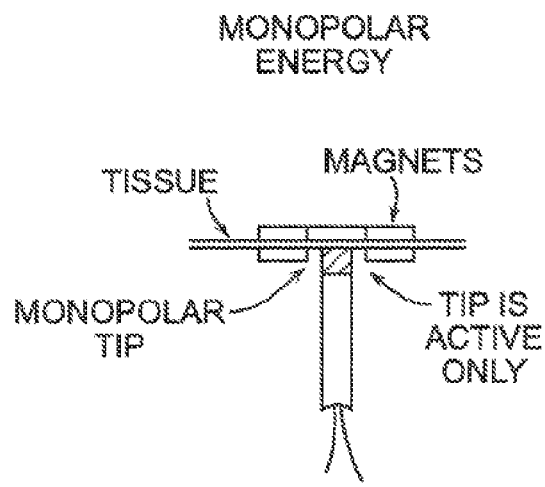
FIG. 39D illustrates a secondary device configured to provide suture or guide element cutting by way of monopolar/bipolar energy.

FIG. 39A illustrates a snare device comprising a resistive heating element for cutting guide elements. FIGS. 39B and 39C illustrate a snare device comprising a ring member having a cutting edge for cutting guide elements. FIG. 39D illustrates a secondary device configured to provide suture or guide element cutting by way of monopolar/bipolar energy.

Figure 40:
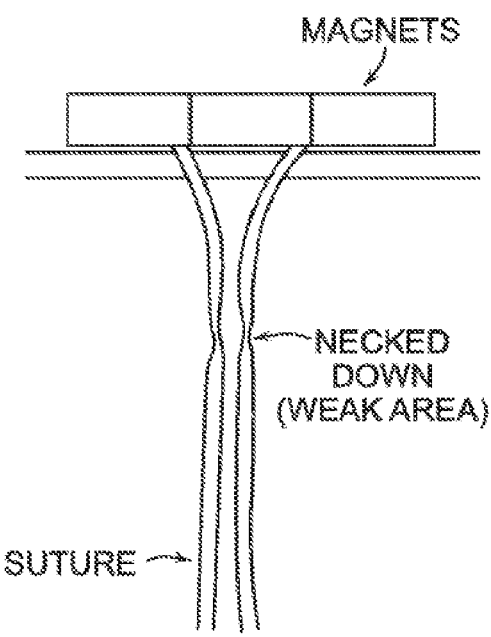
FIG. 40 illustrates breakaway guide elements or sutures.
Figure 41:
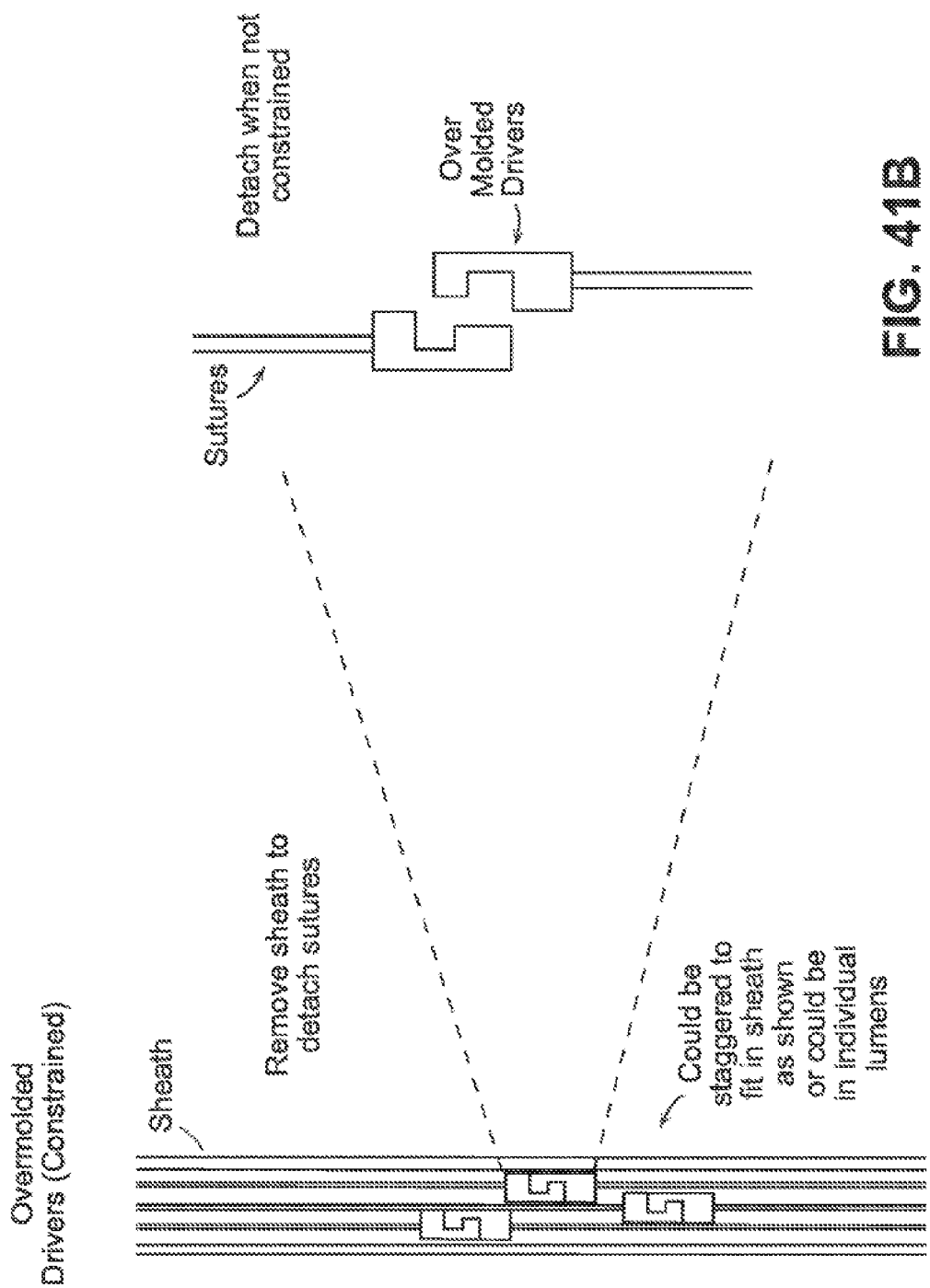
FIGS. 41A and 41B illustrate a detachable suture assembly.

FIG. 40 illustrates breakaway guide elements or sutures. FIGS. 41A and 41B illustrate a detachable suture assembly.

Accordingly, the invention provides improved devices and techniques for minimally invasive formation of anastomoses within the body, e.g., the gastrointestinal tract. Such devices and techniques facilitate faster and less-expensive treatments for chronic diseases such as obesity and diabetes. Such techniques also reduce the time and pain associated with palliative treatments for diseases such as cancers, such as stomach or colon cancer. More specifically, the invention provides various systems, devices, and methods for the delivery, deployment, and positioning of magnetic compression devices at a desired site so as to improve the accuracy of anastomoses creation between tissues, organs, or the like.

Figure 42:
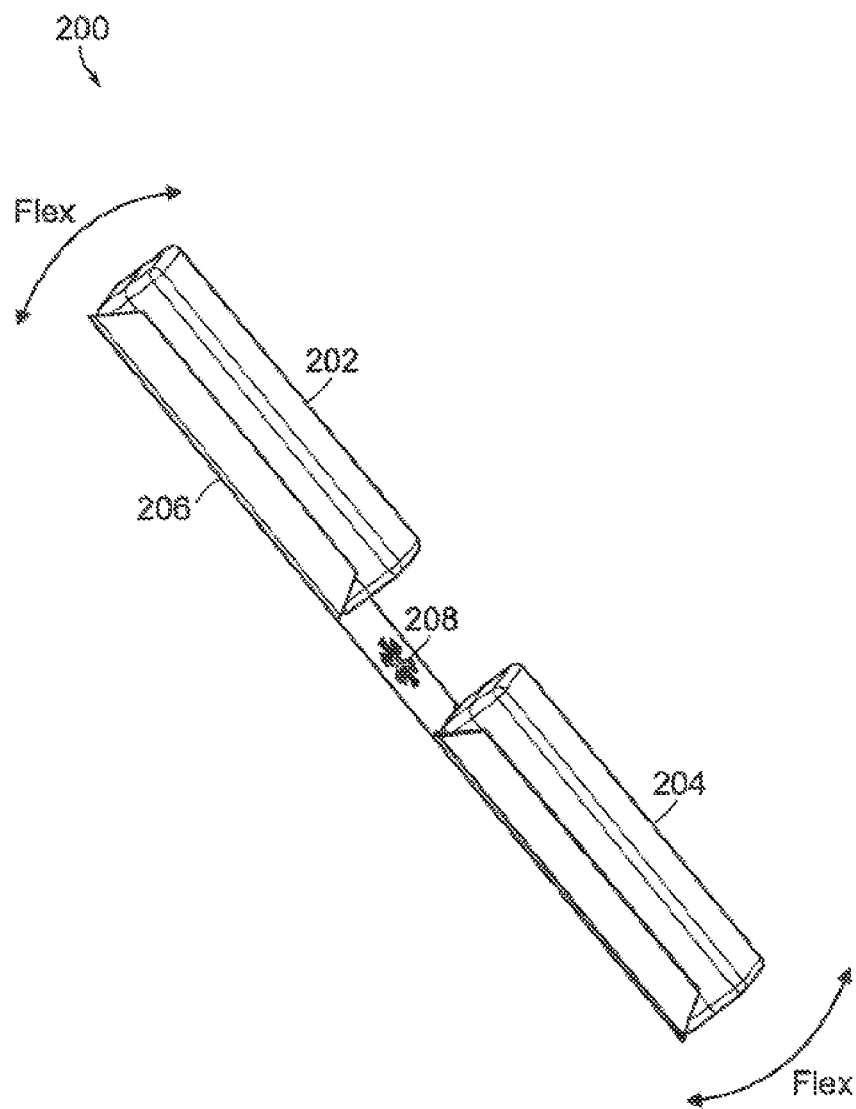
FIG. 42 illustrates a perspective view of another embodiment of a magnetic assembly consistent with the present disclosure.

FIG. 42 illustrates a perspective view of another embodiment of a magnetic assembly 200 consistent with the present disclosure. The magnetic assembly 200 comprises a pair of magnetic segments 202, 204 generally arranged in a linear alignment with one another (e.g., aligned in an end-to-end fashion) and coupled together via a flexible exoskeleton element 206. The segments 202, 204 are spaced apart via a central portion 108 of the exoskeleton 206. The central portion 208 may include a connection member for receiving a corresponding connection member of a placement device to assist in delivery of the magnetic assembly 200, as will be described in greater detail herein. The exoskeleton may be made from a resilient material that will retain its shape after deformation, such as a polymer or metal alloy. In some embodiments, the metal alloy will comprise nickel, such as nitinol. Exemplary exoskeleton embodiments are described in U.S. Pat. Nos. 8,870,898, 8,870,899, 9,763,664, the contents of each of which are incorporated by reference herein in their entirety.

The magnetic assembly 200 is configured to be delivered and deployed at a target site via a delivery device 100. As previously described, the present invention provides improved devices and techniques for minimally-invasive formation of anastomoses within the body, e.g., the gastrointestinal tract. Such devices and techniques facilitate faster and less-expensive treatments for chronic diseases such as obesity and diabetes. Such techniques also reduce the time and pain associated with palliative treatments for diseases such as cancers, such as stomach or colon cancer. More specifically, the invention provides a system including a delivery device 100 for introducing and delivering, via a minimally-invasive technique, a pair of magnetic assemblies between adjacent organs to bridge walls of tissue of each organ together to thereby form a passage therebetween (i.e., an anastomosis). The delivery device 100 is particularly useful in delivering the pair of magnetic assemblies to a target site within the gastrointestinal tract to thereby form anastomosis between gastric and gall bladder walls to provide adequate drainage from the gallbladder when blockage is occurring (due to disease or other health-related issues).

FIGS. 43A-43I illustrate various steps in deploying a pair of magnetic assemblies 200a, 200b to a target site for subsequent formation of anastomosis. In the embodiments described herein, the system generally includes a single scope, such as an endoscope, laparoscope, catheter, trocar, or other access device, through which a delivery device is advanced to a target site for delivering and positioning a pair of magnetic assemblies 200a, 200b for subsequent formation of anastomosis at the target site. In particular, the delivery device 100 comprises an elongate hollow body 102, such as a catheter, shaped and/or sized to fit within the scope. The delivery device includes a working channel in which a pair of magnetic assemblies 200a, 200b is loaded. The delivery device further includes a distal end 104 configured to pierce, or otherwise penetrate, through tissue.

Figure 43A:
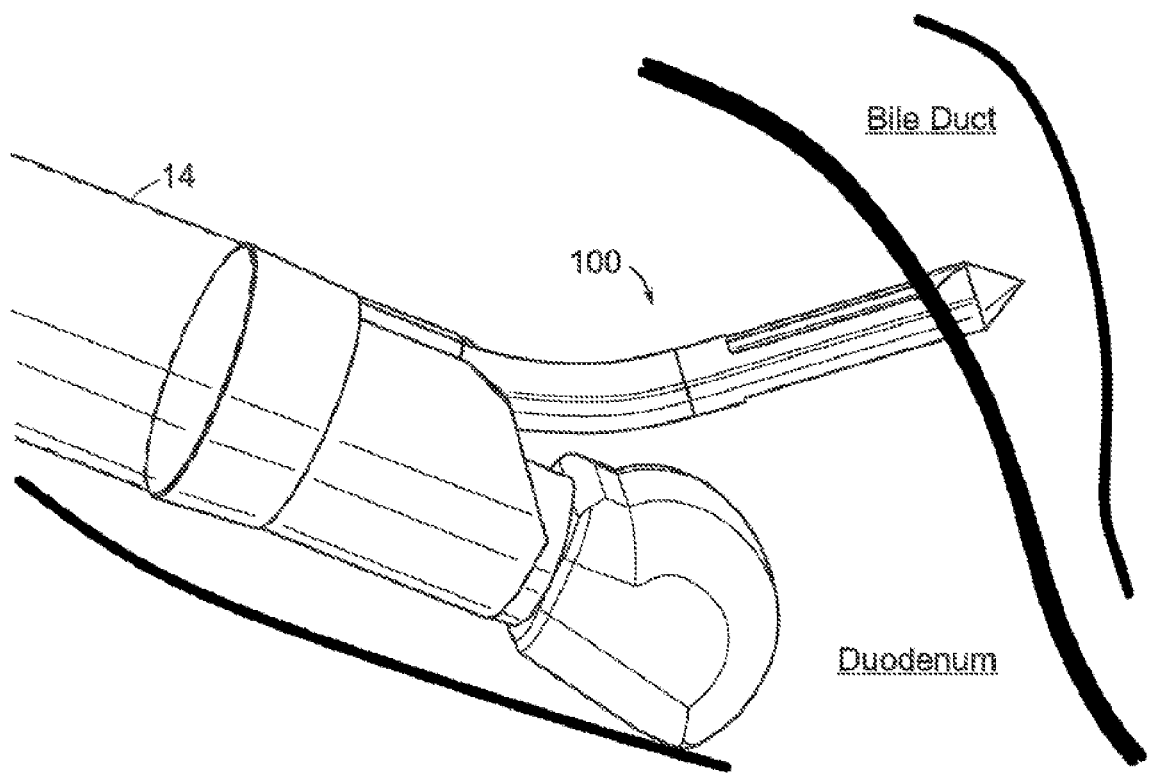
FIG. 43A illustrates advancement of a distal tip of a delivery device through respective tissue walls of adjacent organs at a target site for subsequent formation of an anastomosis therebetween.
Figure 43B:
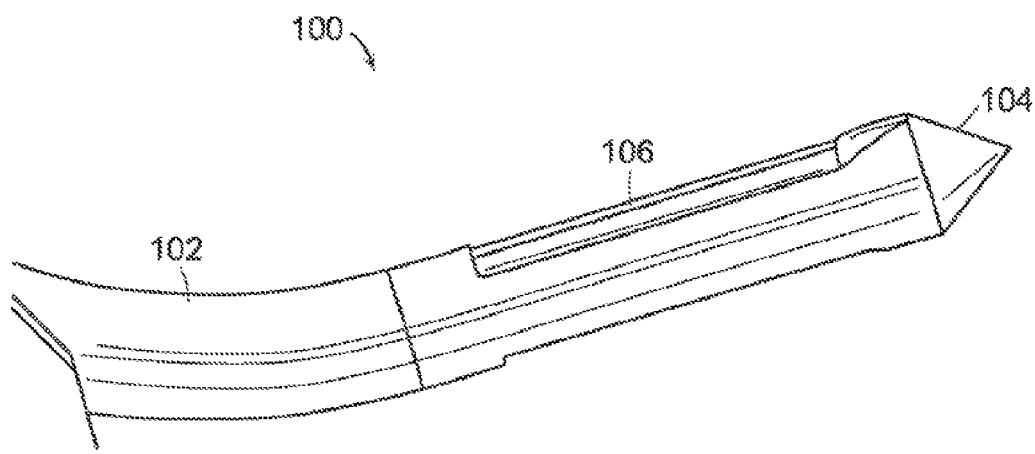
FIG. 43B is an enlarged view of a distal end of the delivery device illustrating the slot extending entirely through a side of the body of the delivery device.

For example, FIG. 43A illustrates advancement of a distal tip of a delivery device 100 through respective tissue walls of adjacent organs at a target site for subsequent formation of an anastomosis therebetween. For example, the distal end 104 may have a sharp tip for piercing tissue and/or may utilize energy to penetrate through tissue (i.e., a hot tip). The body 102 of the delivery device 100 further includes a slot or opening 106 adjacent to the distal end 104, as shown in FIG. 43B. As shown, the slot extends entirely through a side of the body 102 of the delivery device 100. The slot 106 is shaped and/or sized to receive the magnetic assemblies 200a, 200b therethrough, such that the magnetic assemblies 200a, 200b pass through the working channel and exit the delivery device 100 via the slot 106. The delivery device 100 further includes a placement member 108, generally in the form of a wire or the like, that is releasably coupled to one or both of the magnetic assemblies 200a, 200b and provides a means of deploying the magnetic assemblies 200a, 200b from the distal end of the delivery device 100 via the slot 106.

Figure 43C:
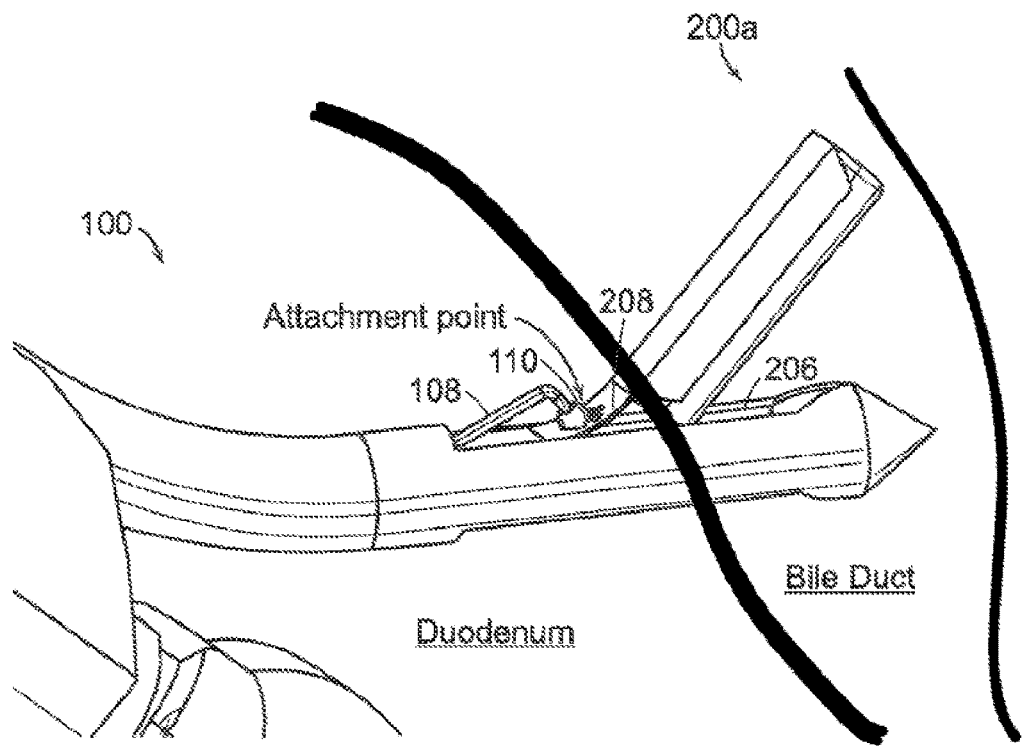
FIG. 43C illustrates delivery of a first magnetic assembly into a first organ.
Figure 43D:
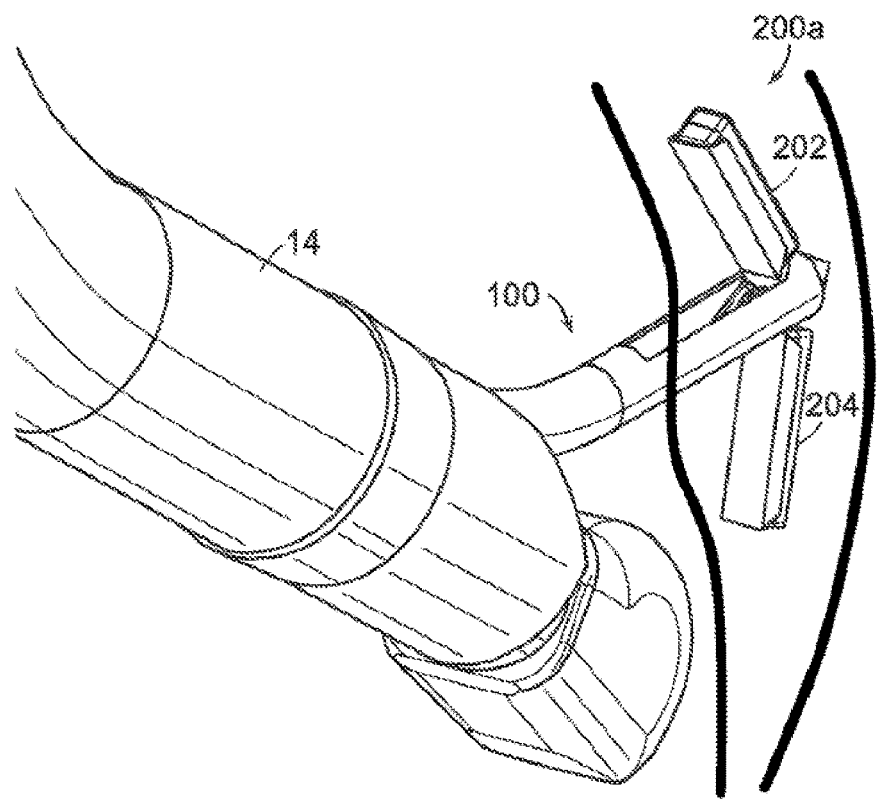
FIG. 43D illustrates deployment of the first magnetic assembly into the first organ while remaining retained within the slot of the delivery device.

During a procedure, a surgeon or other trained medical professional may advance a scope (e.g., endoscope) within a hollow body of the patient and position the scope at a desired anatomical location for formation of the anastomosis based on either a visual depiction of the location of the target site as provided by an imaging modality providing a medical imaging procedure (e.g., ultrasound (US), wavelength detection, X-ray-based imaging, illumination, computed tomography (CT), radiography, and fluoroscopy, or a combination thereof). The surgeon may advance the distal tip 104 of the delivery device 100 through adjacent walls of a pair of organs (i.e., through a wall of the duodenum and a wall of the common bile duct), in any manner previously described herein. Upon advancing distal end 104, including the slot 106, into the first organ (i.e., common bile duct), the surgeon may utilize the placement member 108 to manually deliver and deploy a first magnetic assembly 200a into the first organ via the slot. For example, FIG. 43C illustrates delivery of a first magnetic assembly 200a into the common bile duct. As shown, the placement member 108 include a connection member 110 at a distal end of the placement member 108, which is configured to be releasably coupled to a corresponding connection member of the central portion 208 of the exoskeleton 206 (indicated by attachment point arrow). Upon advancing and extending the placement member 108 towards the distal end 104 of the delivery device 100, the first magnetic assembly passes from the working channel of the delivery device 100 and through the slot 106 to transition into a deployed state, as illustrated in FIG. 43D. As shown, deployment of the first magnetic assembly 200a results in the pair of magnetic segments 202, 204 to exit the slot 106 on opposite respective sides of the body 102 of the delivery device 100 while the central portion 208 of the exoskeleton 206 remains within the slot 106. In other words, the slot 106 extends entirely through the body 102 of the delivery device 100, from one side to the other. Accordingly, when in a deployed state, the first magnetic assembly 200a is positioned into the first organ while remaining retained within the slot 106 of the delivery device 100.

Figure 43E:
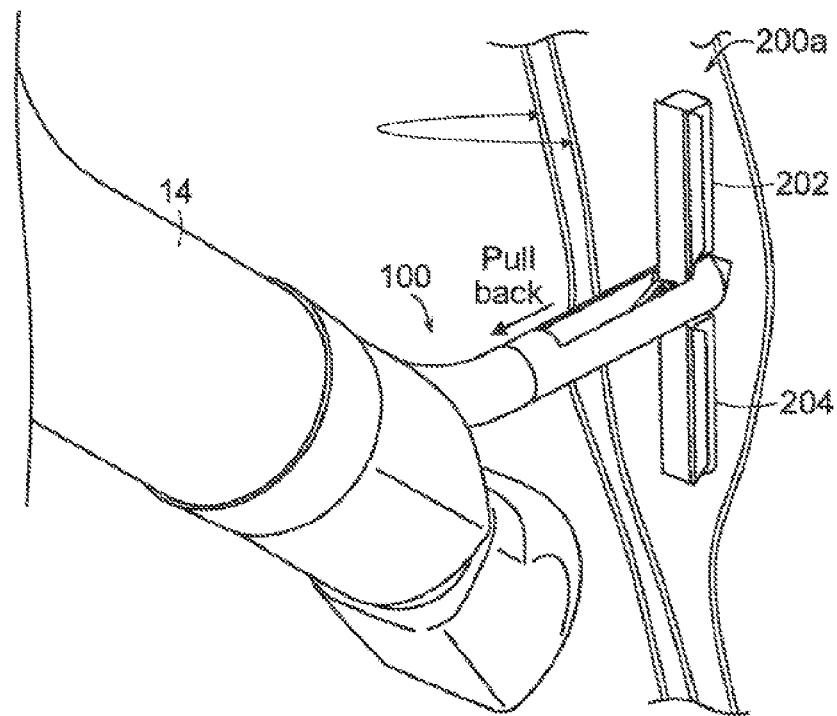
FIG. 43E illustrates a fully deployed first magnetic assembly within the first organ and pulling back of the delivery device to thereby draw the first magnetic assembly against a wall of the first organ in preparation for delivery and deployment of the second magnetic assembly in the second organ.

At this point, the surgeon need only pull back upon the delivery device 100 until the first magnetic assembly 200a engages the tissue of the first organ and the majority of the slot 106 is positioned within the second organ. The surgeon is able to then deliver and deploy the second magnetic assembly 200b into the second organ (i.e., the duodenum). FIG. 43E illustrates a fully deployed first magnetic assembly 200a within the first organ and pulling back of the delivery device 100 to thereby draw the first magnetic assembly 200a against a wall of the common bile duct in preparation for delivery and deployment of the second magnetic assembly 200b in the duodenum.

Figure 43F:
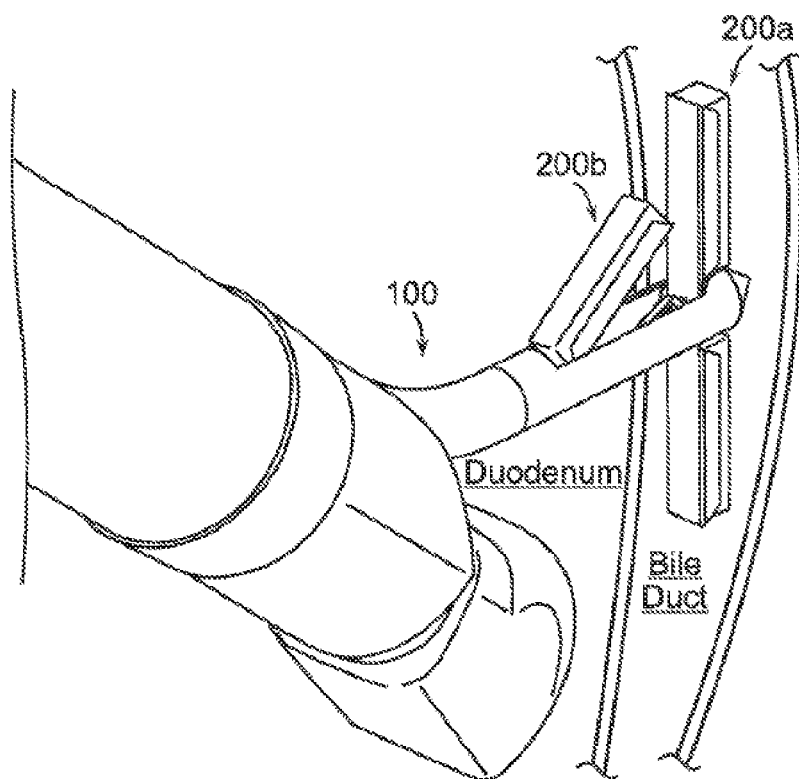
FIG. 43F illustrates delivery of the second magnetic assembly into the second organ.
Figure 43G:
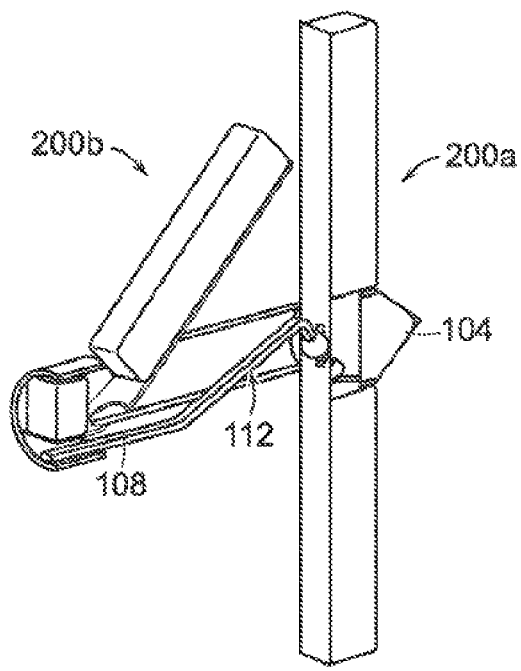
FIG. 43G is an enlarged view, partly in section, of the second magnetic assembly advancing to a deployed state.
Figure 43H:
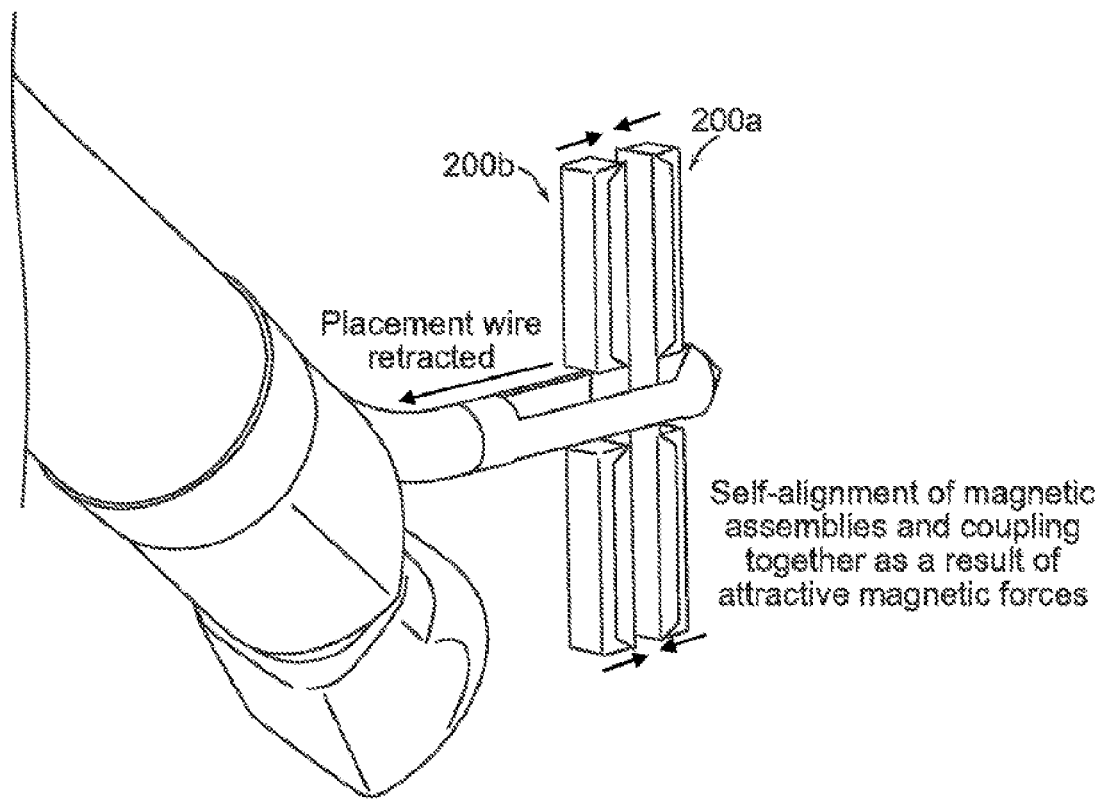
FIG. 43H illustrates the first and second magnetic assemblies in fully deployed states and coupled to one another as a result of attractive magnetic forces therebetween.

The second magnetic assembly 200b deploys in a similar fashion as the first magnetic assembly 200a, in that magnetic segments 202, 204 of the second magnetic assembly 200b exit the slot 106 on opposite respective sides of the body 102 of the delivery device 100 while a central portion 208 of an exoskeleton 206 remains retained within the slot 106. FIG. 43F illustrates delivery of the second magnetic assembly 200b into the duodenum. FIG. 43G is an enlarged view, partly in section, of the second magnetic assembly 200b advancing to a deployed state. As shown, as the second magnetic assembly 200b is advanced through the working channel and towards the slot 106, the assembly 200b is configured to engage a ramped section 112 of the placement member which assisted in directing at least one of the segments of the assembly 200b into place, as shown. FIG. 43H illustrates the first and second magnetic assemblies 200a, 200b in fully deployed states. The first and second magnetic assemblies 200a, 200b are substantially aligned with one another and, due to attractive magnetic forces, the first and second magnetic assemblies 200a, 200b will couple to one another.

Figure 43I:
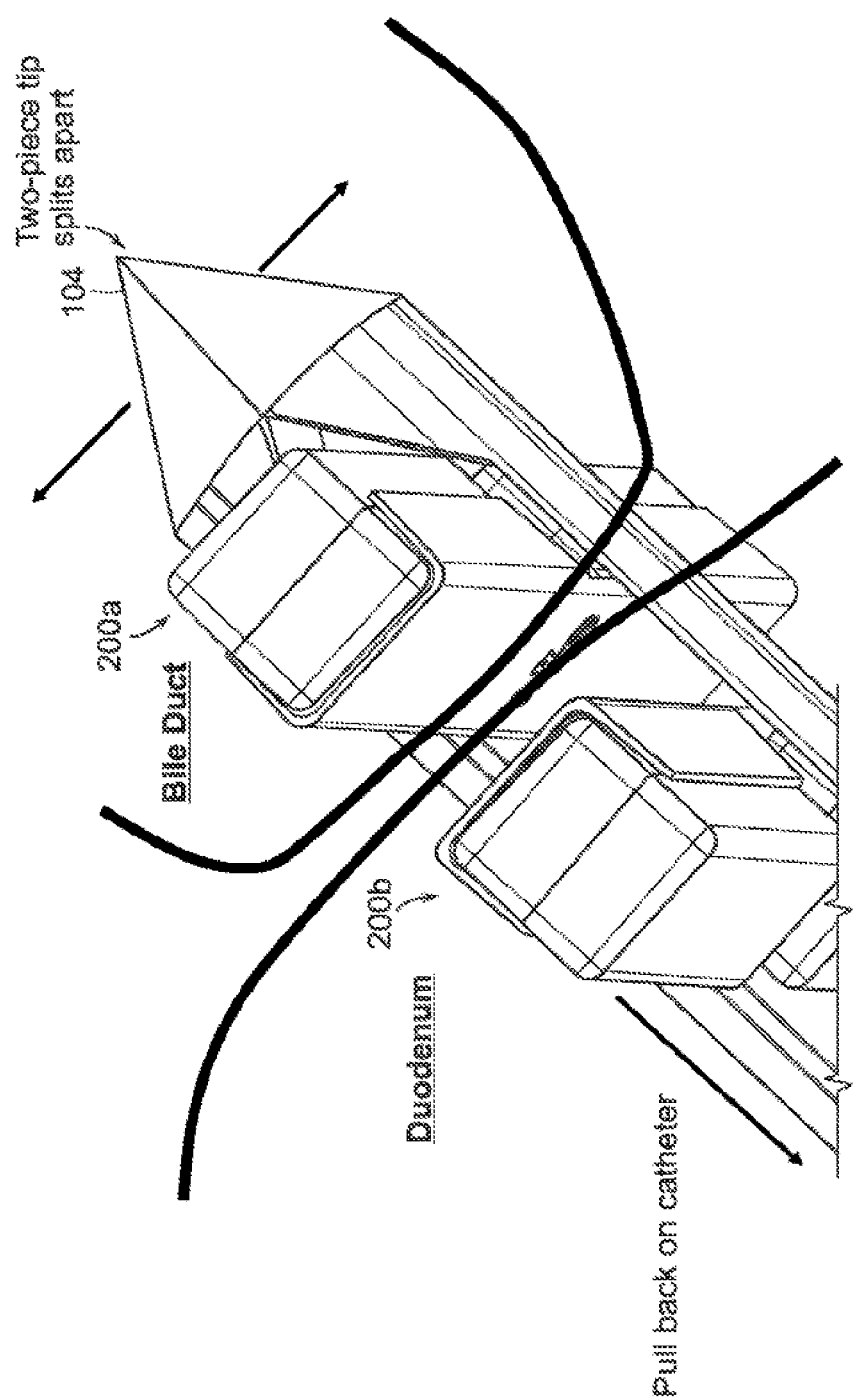
FIG. 43I illustrates the distal end of the delivery device constructed from two halves and configured to split apart to allow the delivery device to be removed from the target site while the pair of magnetic assemblies remain coupled to one another to form anastomosis at the target site.
Figure 44A:
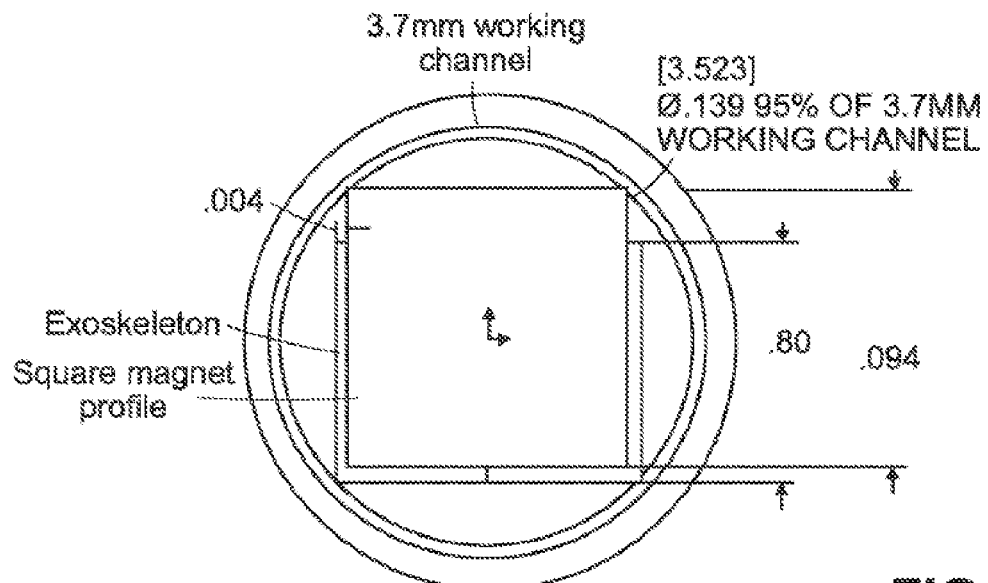
FIGS. 44A, 44B, 44C, and 44D are cross-sectional views of various profiles of magnet segments of magnetic assemblies within a working channel of a standard scope.
Figure 44B:
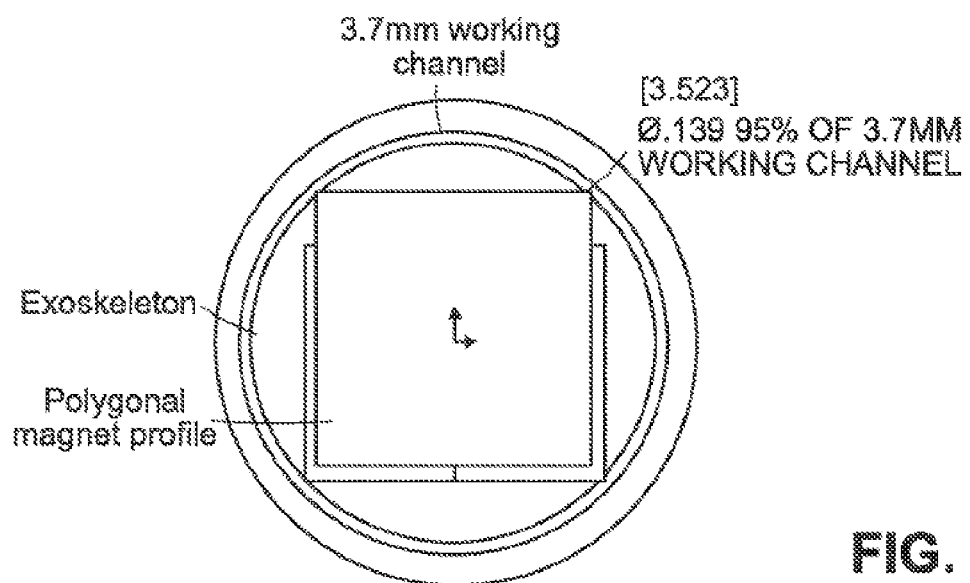
Figure 44C:
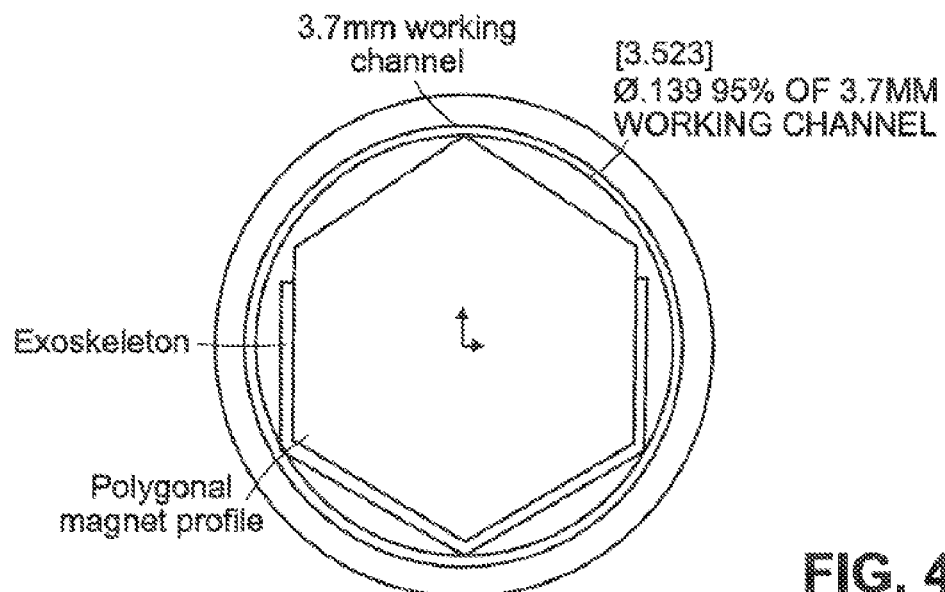
Figure 44D:
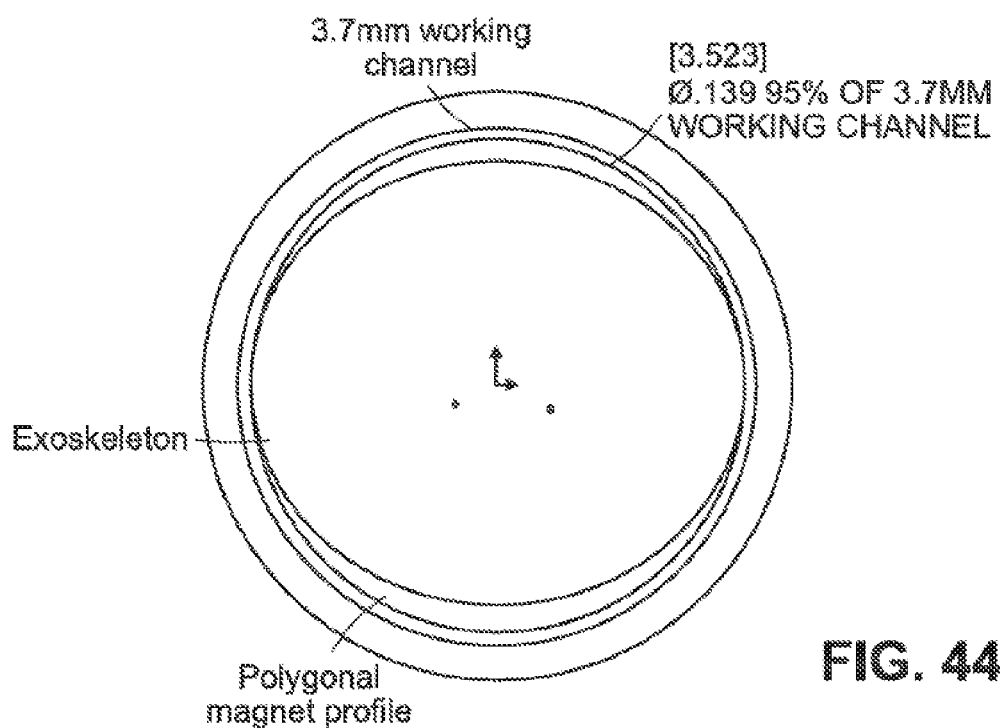

As shown in FIG. 43I, the distal end 104 of the delivery device 100 is comprised of two halves that, when in a default state, form a relatively uniform tip shape. However, the distal end comprises a deformable material (i.e., shape memory material), such that, upon application of sufficient force, the two halves will split apart. As such, once both the first and second magnetic assemblies 200a, 200b have been delivered and are effectively coupled to one another (but are still retained within the slot 106), the surgeon need only pull back on the delivery device 100 which then causes the magnetic assemblies 200a, 200b to make contact with the distal end 104 and force the two halves of the distal end 104 to split apart, allowing the distal end of the delivery device to be withdrawn from the target site while the pair of magnetic assemblies 200a, 200b remain in place. The pair of magnetic assemblies 200a, 200b compress the walls of each respective organ therebetween, subsequently forming an anastomosis between the organs (i.e., anastomosis between the duodenum and the common bile duct).

Upon deployment, each magnetic assembly has a width and a length generally corresponding to a width of a respective segment and a length that is approximately twice the length of each segment. As a result, the pair of magnetic assemblies, when coupled to one another, generally form a substantially linear package and the resulting anastomosis formed may generally be rectangular in shape, but may naturally form a round or oval shape. The resulting anastomosis may have a 1:1 aspect ratio relative to the dimensions of the magnetic assemblies. However, the present invention allows for larger aspect ratios (i.e., a larger anastomosis to form relative to the dimensions of the magnetic assemblies). In particular, prior art systems and methods that include the use of magnets for creating anastomosis are generally limited based on the dimensions of the working channel of the scope or catheter used for delivering such magnets, which, in turn, limits the resulting size of the anastomosis. The magnetic assembly design of the present invention overcomes such limitations.

For example, the design of the magnetic assembly of the present invention, notably the coupling of multiple magnetic segments to one another via an exoskeleton, allow for any number of segments to be included in a single assembly, and thus the resulting anastomosis has a greater size relative to the dimensions of the working channel of the scope. For example, in some embodiments, the resulting anastomosis may include an aspect ratio in the range of 2:1 to 10:1 or greater.

FIGS. 44A-44D are cross-sectional views of various profiles of magnet segments of magnetic assemblies within a working channel of a standard scope. The cross sectional areas of magnets are illustrated, showing polygons as well as ellipses and circles taking between 10 and percent of the annular space of the working channel. With the guidelines for the magnetic profile being in place, the next constraint for the device is the axial ratio of a minimum of 6:1 and a maximum of 50:1. This segmented length once assembled in the body can have either a regular or irregular shape.

FIG. 45 provides a listing of working channel sizes that are currently available and would be considered usable/feasible to deploy a magnetic array with a cage to produce an anastomosis. These are the current sizes but it does not limit our future capabilities as scope channel sizes increase/decrease with market and device changes. The summary of sizing can be summarized into: 1.0 mm-6.0 mm (including a bleed scope called the "clot buster") with our current sized device designed around the 3.7 mm.

Accordingly, the delivery device of the present disclosure produces a low-profile linear anastomosis that would allow certain complications, particularly those associated with blockage of the common bile duct, to be mitigated. In particular, patients experiencing a blockage of the common bile duct often undergo some sort of procedure to either remove the blockage or allow procedure is a sphincterotomy, or some sort of draining stent placement procedure. There are procedures which present decompression of the bile duct in a traditional way, but are not possible in a minimally noninvasive manner. Such procedures include, for example, a sphincterotomy, which is not possible due to inability to cannulate the common bile duct, inability to account for anatomical alterations, particularly when during heavily diseased states. Utilizing the magnetic closure force profile of the present invention would allow minimal bleeding and create a semi-permanent slit profile. This slit profile would help to resist "sump syndrome" and help to create a drainage point which would remain effectively infection free.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein

What is claimed is:

1. A magnetic compression system, comprising: a delivery device having an elongate hollow body and two elongate openings on opposite sides of the delivery device, a magnetic compression device, the magnetic compression device comprising:
   a pair of magnetic segments affixed to and coupled together via a flexible exoskeleton that partially encapsulates the magnetic segments, wherein the magnetic compression device comprises a delivery configuration in which the pair of segments are arranged in a linear alignment with one another and spaced apart via a central portion of the exoskeleton longitudinally within the elongate hollow body and a deployed configuration in which the pair of magnetic segments sequentially exit laterally through the elongate openings on opposite sides of the delivery device while the central portion remains with the elongate hollow body.

2. The device of claim 1, wherein the flexible exoskeleton element is formed of a shape memory material, and wherein the shape memory material is biased to the deployed configuration.

3. The device of claim 1, wherein the shape memory material includes a polymer.

4. The device of claim 1, wherein the shape memory material includes a metal alloy.

5. The device of claim 1, wherein the central portion is configured to be releasably coupled to a connection member of the delivery device.

6. The device of claim 5, further comprising a placement member including the connection member at a distal end of the placement member, the connection member being releasably coupled to the central portion.

7. The device of claim 6, wherein the placement member is a wire.

8. The device of claim 6, wherein the placement member comprises a ramped section to assist in directing at least one of the magnetic segments.

9. The device of claim 1, wherein the magnetic compression device is configured to fit within a working channel of the delivery device when in the delivery configuration.

10. The device of claim 9, wherein the delivery device is an endoscope.

11. The device of claim 9, wherein the delivery device is a laparoscope.

12. The device of claim 1, wherein the magnetic segments are affixed to the flexible exoskeleton by pinching or grasping of the flexible exoskeleton.

13. The device of claim 1, wherein the magnetic segments are affixed to the flexible exoskeleton with glue.

14. The device of claim 1, wherein the magnetic segments are affixed to the flexible exoskeleton with wire.

15. The device of claim 1, wherein the magnetic segments are affixed to the flexible exoskeleton with a suture.

16. The device of claim 1, wherein the magnetic segments are affixed to the flexible exoskeleton with a physical coupling.

17. A system comprising:
a delivery device having an elongate hollow body and two elongate openings on opposite sides of the delivery device; and
a magnetic compression device comprising a pair of magnetic segments affixed to and coupled together via a flexible exoskeleton that partially encapsulates the magnetic segments, wherein the magnetic compression device is disposed within the elongate hollow body of the delivery device in a delivery configuration in which the pair of segments are arranged in a linear alignment with one another and spaced apart via a central portion of the exoskeleton longitudinally within the elongate hollow body, and wherein the magnetic compression device is configured for the magnetic segments to sequentially exit the elongate hollow body laterally through the elongate openings on opposite sides of the delivery device into a deployed configuration while the central portion remains with the elongate hollow body.

18. The system of claim 17, wherein the flexible exoskeleton includes a shape memory material, and wherein the shape memory material is biased to the deployed configuration.

19. The system of claim 17, further comprising:
a placement member including a connection member at a distal end of the placement member, the connection member being releasably coupled to the central portion.

20. The system of claim 17, wherein the delivery device includes a tip that opens to allow the central portion of the exoskeleton to exit the elongate hollow body.

* * * * *